United States Patent
Finkelstein et al.

(10) Patent No.: US 12,128,593 B2
(45) Date of Patent: Oct. 29, 2024

(54) MANUFACTURING PROCESS FOR HOLLOW PLUNGER ROD

(71) Applicant: AMGEN INC., Thousand Oaks, CA (US)

(72) Inventors: Emil Finkelstein, Frederiksberg (DK); Jan Jensen, Copenhagen (DK)

(73) Assignee: AMGEN INC., Thousand Oaks, CA (US)

( * ) Notice: Subject to any disclaimer, the term of this patent is extended or adjusted under 35 U.S.C. 154(b) by 312 days.

(21) Appl. No.: 17/687,725

(22) Filed: Mar. 7, 2022

(65) Prior Publication Data

US 2022/0281146 A1 Sep. 8, 2022

Related U.S. Application Data

(60) Provisional application No. 63/158,165, filed on Mar. 8, 2021.

(51) Int. Cl.
| | |
|---|---|
| *B29C 45/14* | (2006.01) |
| *A61M 5/315* | (2006.01) |
| *B29K 705/00* | (2006.01) |
| *B29L 31/00* | (2006.01) |

(52) U.S. Cl.
CPC ... *B29C 45/14598* (2013.01); *A61M 5/31511* (2013.01); *B29C 45/14065* (2013.01); *B29C 45/14221* (2013.01); *A61M 2207/00* (2013.01); *B29C 2045/14155* (2013.01); *B29K 2705/00* (2013.01); *B29L 2031/7544* (2013.01)

(58) Field of Classification Search
CPC ....................................................... B29C 45/14
See application file for complete search history.

(56) References Cited

U.S. PATENT DOCUMENTS

| | | | |
|---|---|---|---|
| 2006/0089602 A1* | 4/2006 | Boucherie | B29C 45/1657 264/328.8 |
| 2015/0174331 A1* | 6/2015 | Young | A61M 5/288 72/330 |
| 2016/0354555 A1 | 12/2016 | Gibson et al. | |

FOREIGN PATENT DOCUMENTS

| | | |
|---|---|---|
| CN | 110369587 A | 10/2019 |
| DE | 102010005816 A1 | 7/2011 |
| WO | WO-2004/035289 A1 | 4/2004 |
| WO | WO-2015187797 A1 | 12/2015 |

OTHER PUBLICATIONS

International Application No. PCT/US2022/019069, International Search Report and Written Opinion, mailed Jun. 28, 2022.

* cited by examiner

*Primary Examiner* — Edmund H Lee

(57) ABSTRACT

A method of manufacturing a plunger of a drug delivery device includes forming a plunger body. The method includes loading the plunger body into a cavity of a first molding tool of a molding system. The cavity is at least partially defined by a first molding portion and a second molding portion. The method includes coupling a second molding tool to the first molding tool to form a plurality of channels defined by grooves in the first and second molding tools, and injecting molten plastic into the plurality of channels to form an overmolded plunger body. The overmolded plunger body includes a head coupled to the first end of the plunger body and a foot coupled to the second end of the plunger body. The foot is at least partially coupled to the inner wall and the head is coupled to the outer wall of the plunger body.

20 Claims, 33 Drawing Sheets

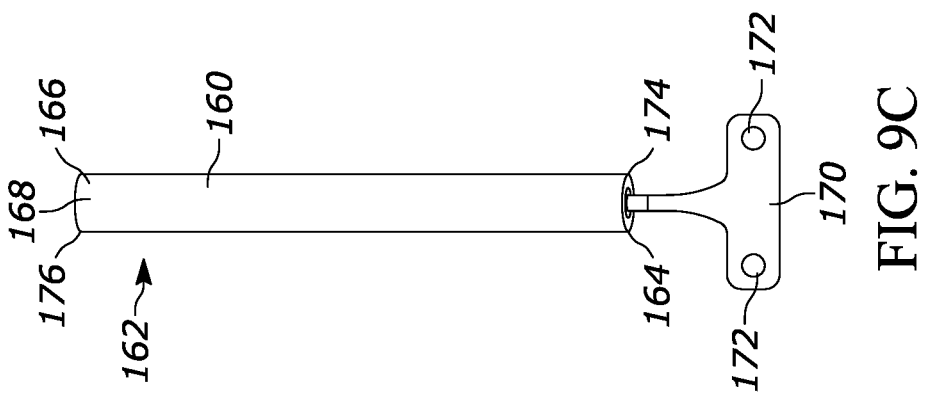
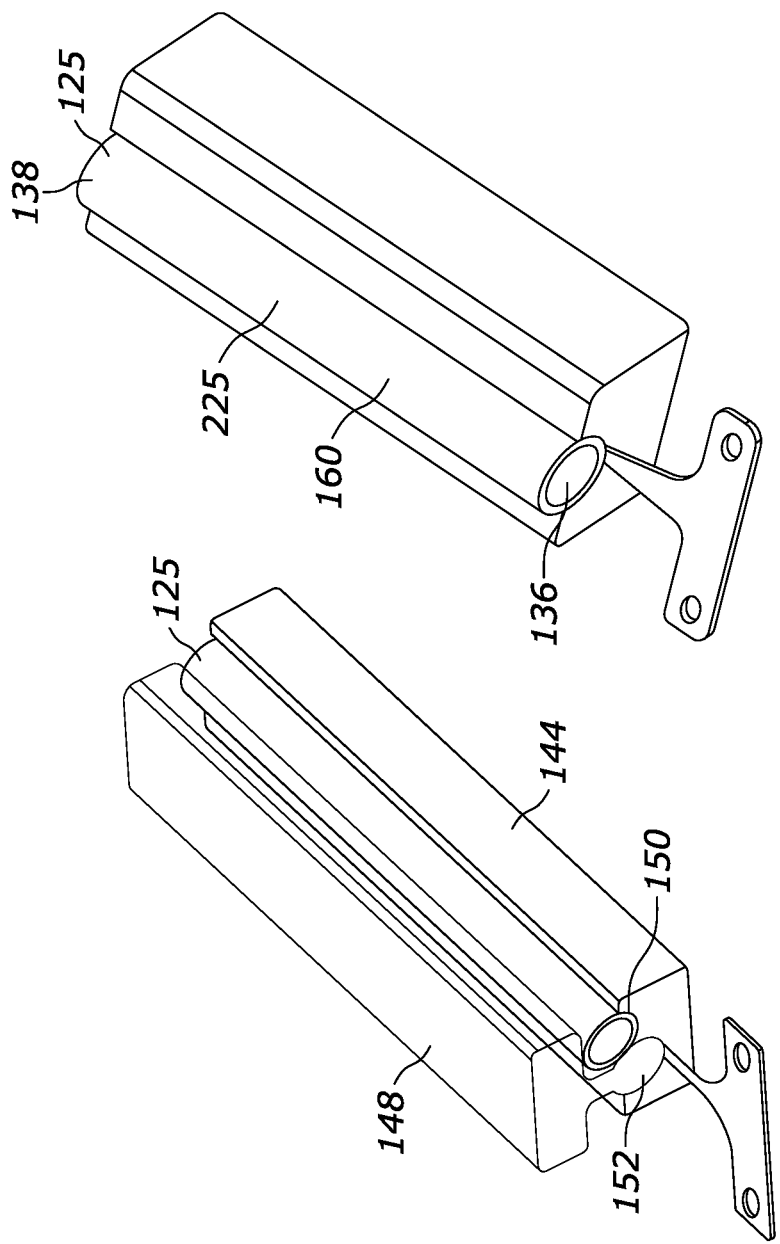
FIG. 9C
FIG. 9B
FIG. 9A

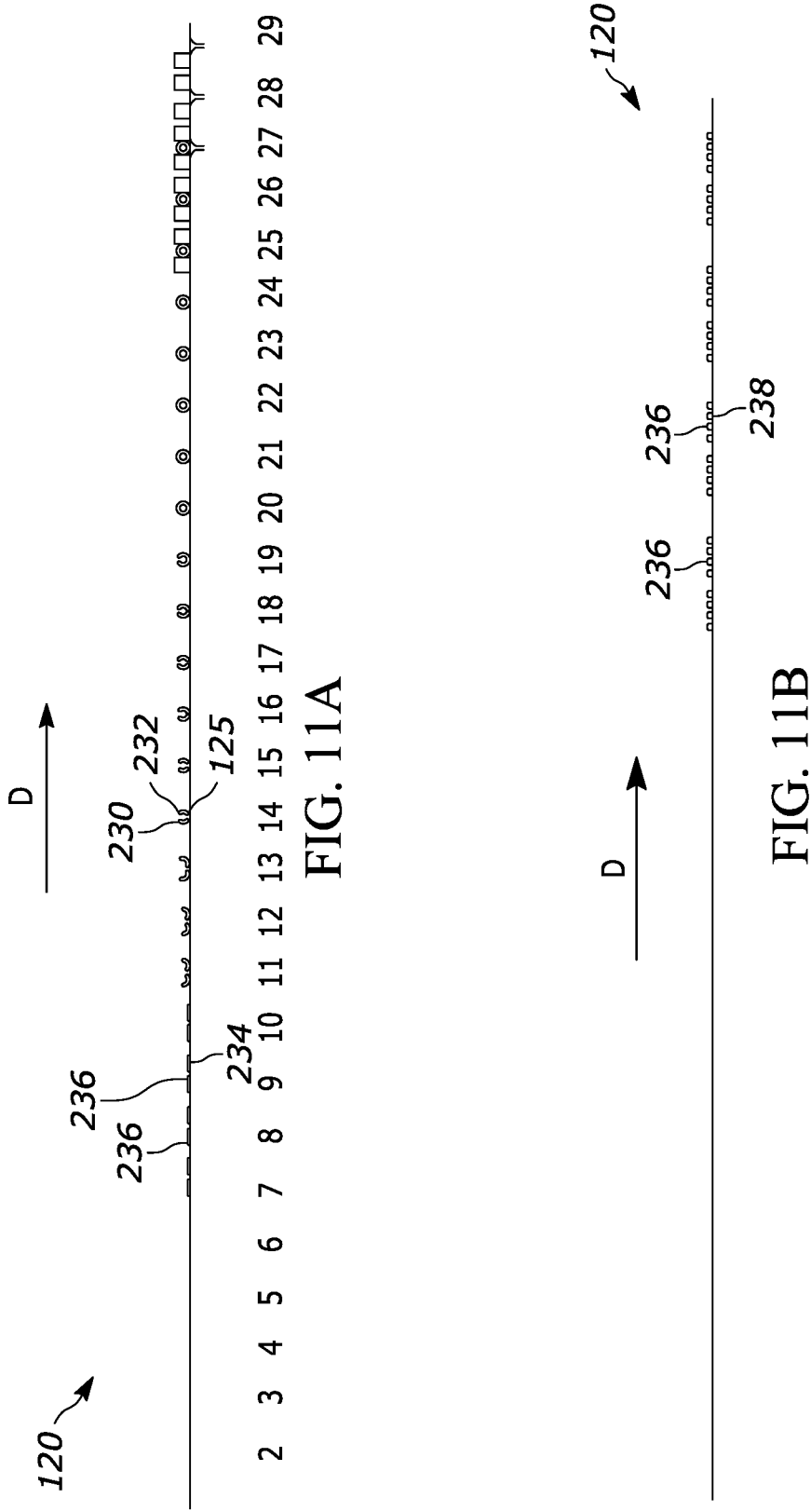

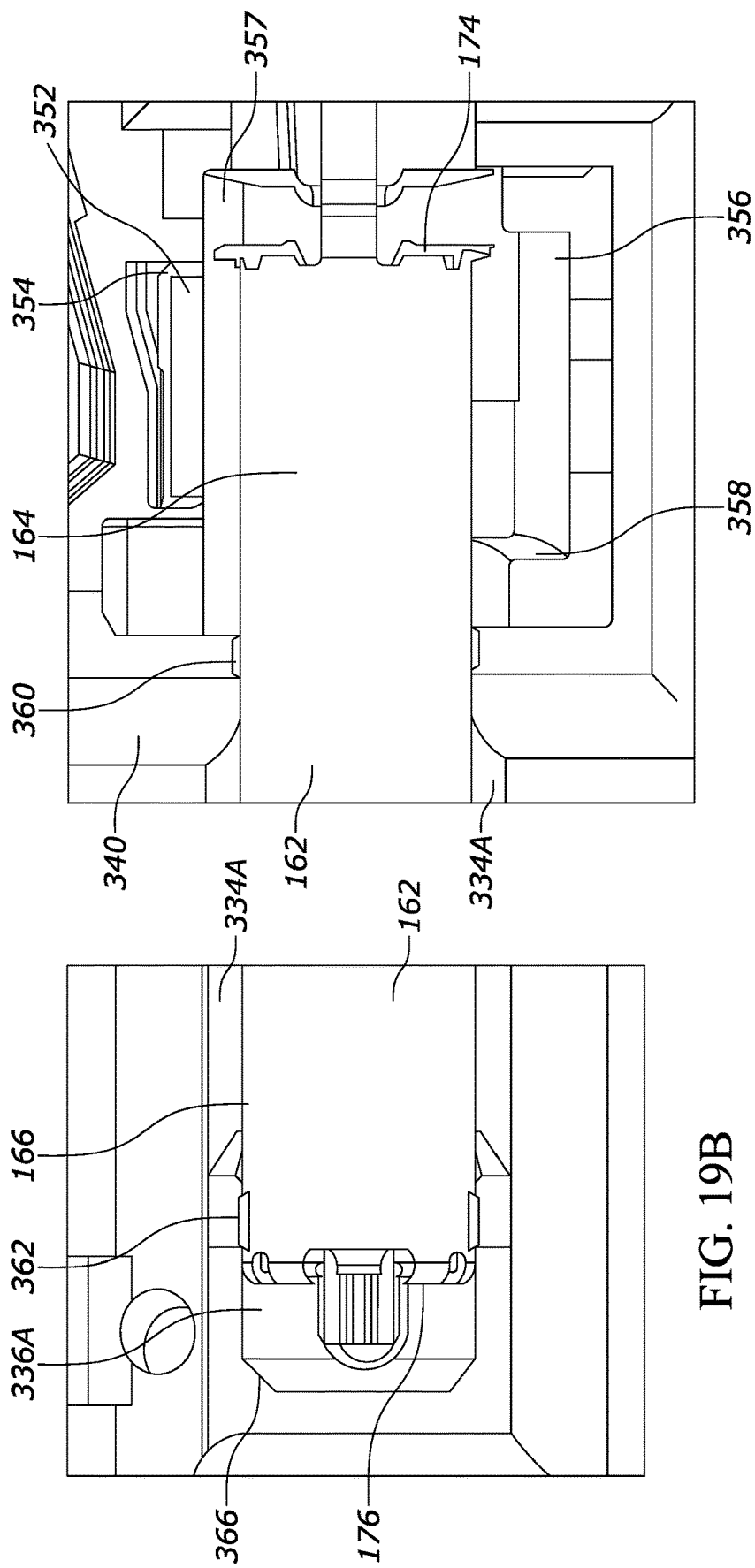

MANUFACTURING PROCESS FOR HOLLOW PLUNGER ROD

CROSS-REFERENCE TO RELATED APPLICATION

Priority is claimed to U.S. Provisional Patent Application No. 63/158,165, filed Mar. 8, 2021, the entire contents of which are hereby expressly incorporated by reference herein.

FIELD OF DISCLOSURE

The present disclosure relates to drug delivery devices, and, more particularly, methods of manufacturing drug delivery devices.

BACKGROUND

A general aversion to exposed needles, as well as health and safety issues, have led to the development of drug delivery devices which conceal a needle or other insertion member prior to use and which automate various aspects of an injection process. Such devices offer a variety of benefits as compared with traditional forms of drug delivery including, for example, delivery via a conventional syringe.

Many injector systems use coil and other spring structures to provide actuation energy for functions such as needle insertion and/or fluid delivery. The use of springs can offer benefits of simplicity and low cost, but it may have certain limitations. For example, there is a linear relationship between force and displacement in spring actuators. To provide sufficient energy for drug delivery at the end of plunger stroke, an excessive amount of energy may be input to the system as drug delivery commences. As another example, as higher viscosity drugs are delivered via auto-injectors, the requisite spring forces will likely increase. Springs with higher spring constants may transmit more force to the drug product and primary container. Various physical characteristics of a spring may affect the spring rate, and thus the spring force, such as wire diameter of the spring, mean diameter of the spring, the number of spring coils, and the spring material. Therefore, it may be desirable and/or advantageous to include device components that permit flexibility in spring design and/or that facilitate the use of springs with different physical characteristics with the remaining device components.

The present disclosure sets forth drug delivery devices embodying advantageous alternatives to existing drug delivery devices, and that may address one or more of the challenges or needs mentioned herein.

SUMMARY

In accordance with a first exemplary aspect, a method of manufacturing a plunger of a drug delivery device may include inserting a blank of sheet metal in an inlet of a stamping machine, the stamping machine including the inlet, an outlet, and a travel path extending between the inlet and the outlet. The method may include activating the stamping machine to advance the blank of sheet metal along the travel path of the stamping machine. The travel path may include a plurality of stages configured to process the blank of sheet metal into a plurality of plunger bodies. Each of the plunger bodies may include an inner wall defining an axial chamber, an outer wall, a first end, and a second end opposite the first end. The method may include forming the plurality of plunger bodies from the blank of sheet metal as the blank of sheet metal passes through the travel path and exits the outlet. The method may include separating each of the plurality of plunger bodies from the blank of sheet metal and loading at least one of the plurality of plunger bodies into a cavity of a molding tool of a molding system. Finally, the method may include injecting molten plastic into a plurality of channels of the molding tool to form an overmolded plunger body. The overmolded plunger body may have at least one overmolded portion.

In accordance with a second exemplary aspect, a method of manufacturing a plunger of a drug delivery device may include forming a plunger body having an inner wall defining an axial chamber and an outer wall, the plunger body including a first end and a second end opposite the first end. The method may include loading the plunger body into a cavity of a first molding tool of a molding system, and coupling a second molding tool to the first molding tool to form a plurality of channels defined by grooves in the first and second molding tools. The second molding tool may include a cavity sized to receive a portion of the plunger body when the plunger body is disposed in the cavity of the first molding tool. Finally, the method may include injecting molten plastic into the plurality of channels to form an overmolded plunger body. The overmolded plunger body may include at least one overmolded portion.

In accordance with a third exemplary aspect, a method of manufacturing a plunger body of a drug delivery device may include inserting a blank of sheet metal in an inlet of a stamping machine. The stamping machine may include the inlet, an outlet, and a travel path extending between the inlet and the outlet. The method may include activating the stamping machine to advance the blank of sheet metal along the travel path of the stamping machine. The travel path may include a plurality of stages configured to process the blank of sheet metal into a plurality of plunger bodies. Each of the plurality of plunger bodies may include an inner wall defining an axial chamber, an outer wall, a first end, and a second end opposite the first end. The method may include forming the plurality of plunger bodies from the blank of sheet metal as the blank of sheet metal passes along the travel path and exits the outlet. Finally, the method may include separating each of the plurality of plunger bodies from the blank of sheet metal.

In accordance with a fourth exemplary aspect, a method of manufacturing a plunger body of a drug delivery device may include inserting a blank of sheet metal in an inlet of a stamping machine, the stamping machine including the inlet, an outlet, and a travel path extending between the inlet and the outlet. The method may include activating the stamping machine to advance the blank of sheet metal along the travel path of the stamping machine. The travel path may include a plurality of stages configured to process a portion of the blank of sheet metal into a plurality of plunger bodies. Each of the plurality of plunger bodies may include an inner wall defining an axial chamber, an outer wall, a first end, and a second end opposite the first end. The method may include forming the plurality of plunger bodies from the blank of sheet metal as the blank of sheet metal advances along the travel path and exits the outlet, and separating each of the plurality of plunger bodies from the blank of sheet metal.

In accordance with a fifth exemplary aspect, a method of molding a plunger of a drug delivery device may include loading a plunger body into a cavity of a first molding tool of a molding system. The plunger body may include an inner wall defining an axial chamber, an outer wall, a first end, a second end opposite the first end. The cavity may at least partially define a first molding portion, a middle portion, and a second molding portion. The method may include coupling a second molding tool to the first molding tool to form a plurality of channels defined by grooves in the first and second molding tools. The method may include injecting molten plastic into the plurality of channels of the first and second molding tools and into the first molding portion and the second molding portion to form an overmolded plunger body. The overmolded plunger body may include a head coupled to the outer wall and at least partially surrounding the first end of the plunger body and a foot coupled to the second end of the plunger body.

In accordance with a sixth exemplary aspect, a molding system for forming a portion of a plunger of a drug delivery device may include a first molding tool having a cavity at least partially defined by a first molding portion, a middle portion, and a second molding portion. A second molding tool may have a cavity corresponding to the cavity of the first molding tool and including a first molding portion, a middle portion, and a second molding portion. A plurality of grooves may be formed in the first molding tool and the second molding tool. The plurality of grooves may be arranged to form a plurality of channels when the first molding tool is coupled to the second molding tool. When the first and second molding tools are coupled, the first molding portions of the first molding tool and the second molding tool may define a head mold for a plunger and the second molding portions of the first molding tool and the second molding tool may define a foot mold for the plunger.

In accordance with a seventh exemplary aspect, a stamping machine for forming a plunger body of a drug delivery device component may include a housing defining an inlet, and an outlet, and a travel path extending between the inlet and the outlet. A gripper may be disposed within the housing and arranged to engage and advance a blank of sheet metal along the travel path of the housing. A plurality of movable dies may be disposed along the travel path and arranged to impact the blank of sheet metal to form a cylindrical plunger body. At least one of the plurality of dies may be disposed above the travel path and at least one of the plurality of dies may be disposed below the travel path.

In accordance with any one or more of the foregoing first through seventh exemplary aspects, a method of manufacturing and molding a plunger and plunger body of a drug delivery device, a molding system, and a stamping machine may further include any one or more of the following preferred forms.

In a preferred form, injecting molten plastic may include injecting molten plastic to form a head portion coupled to the outer wall and at least partially surrounding the first end of the plunger body and a foot portion coupled to the second end of the plunger body.

In a preferred form, loading the at least one of the plurality of plunger bodies may include loading a plurality of plunger bodies into a plurality of cavities formed in the molding tool.

In a preferred form, the method may include coupling a first molding tool to a second molding tool before injecting the plurality of channels of molten plastic.

In a preferred form, the first molding tool may include the cavity sized to receive the plunger body.

In a preferred form, the first and second molding tools may form the plurality of channels when coupled.

In a preferred form, injecting molten plastic into the plurality of channels may include injecting molten plastic into the second molding tool to distribute the molten plastic into a first molding portion and a second molding portion of the cavity.

In a preferred form, loading the at least one of the plurality of plunger bodies includes coupling a hanger attached to the first end of each plunger body to a pin of the molding tool, where the stamping machine forms the hanger in the blank of sheet metal for each of the plurality of plunger bodies In a preferred form, forming the plurality of plunger bodies may include cutting a portion of the blank of sheet metal to create a rectangular cut-out.

In a preferred form, the rectangular cut-out may include a first end, a second end opposite the first end, a first side and a second side extending between the first and second ends, a first surface, and a second surface opposite the first surface.

In a preferred form, the first end may be attached to a first parallel edge of the blank of sheet metal.

In a preferred form, the second end may be attached to a parallel second edge of the blank of sheet metal.

In a preferred form, forming the plurality of plunger bodies may include shaping the rectangular cut-out attached to the blank of sheet metal to form a cylindrical shape by stamping at least one of the first surface and the second surface of the rectangular cut-out with a contoured die.

In a preferred form, forming the plurality of plunger bodies may include gradually bending first and second sides of the rectangular cut-out inward, such that as the blank of sheet metal moves in a direction toward the outlet of the stamping machine, the first surface of the rectangular cut-out defines the inner wall of each of the plurality of plunger bodies.

In a preferred form, cutting the portion the blank of sheet metal to create the rectangular cut-out may include cutting a corrugated edge to form the first end of the rectangular cut-out.

In a preferred form, the method may include bending the corrugated edge of the first end of the rectangular cut-out such that the corrugated edge is substantially perpendicular relative to the first surface of the rectangular cut-out.

In a preferred form, cutting the portion the blank of sheet metal to create the rectangular cut-out may include cutting a corrugated edge to form the second end of the rectangular cut-out.

In a preferred form, the method may include bending the corrugated edge of the second end of the rectangular cut-out such that the corrugated edge is substantially perpendicular relative to the first surface of the rectangular cut-out.

In a preferred form, bending the corrugated edge of the second end may include bending the corrugated edge of the second end towards the first surface of the rectangular cut-out In a preferred form, separating each of the plurality of plunger bodies may include cutting a portion of a parallel edge of the blank of sheet metal to remove the plunger body.

In a preferred form, the portion of the parallel edge may define the hanger connected to the first end of the plunger body.

In a preferred form, inserting the blank of sheet metal may include inserting a flat sheet of stainless steel having a thickness in a range of approximately 0.0001 inches to approximately 0.0003 inches.

In a preferred form, the method may include cooling the overmolded plunger body to form a cured plunger.

In a preferred form, the method may include moving the first molding tool from a first position to a second position before coupling the second molding tool to the first molding tool.

In a preferred form, moving the first molding tool may include rotating a movable table, the first molding tool attached to a surface of the movable table.

In a preferred form, injecting the plurality of channels may include injecting the second molding tool with molten plastic when the first molding tool is in the second position.

In a preferred form, the method may include inserting a rod into the axial chamber of the plunger body before coupling the first molding tool to the second molding tool.

In a preferred form, injecting the plurality of channels may include injecting a curved channel formed in the second molding tool.

In a preferred from, the curved channel may include a diameter in a range of approximately 0.1 mm to approximately 0.2 mm and may be coupled to a second molding portion of the cavity.

In a preferred form, the cavity may be at least partially defined by a first molding portion, a middle portion, and the second molding portion.

In a preferred form, the method may include removing the cured plunger from the first molding tool by activating an ejector pin in the first molding tool.

In a preferred form, the ejector pins may push the cured plunger away from the cavity formed in the first molding tool.

In a preferred form, removing the cured plunger may include automatically severing a plurality of plastic tubes formed in the plurality of channels that are connected to the head and the foot of the cured plunger, thereby providing a plunger.

In a preferred form, loading the plunger body may include loading the first end into a first molding portion of the cavity and loading the second end into a second molding portion of the cavity.

In a preferred form, injecting the plurality of channels may include injecting molten plastic into the first and second molding tools, In a preferred form, the plurality of channels may extend between a first molding portion and a second molding portion of the cavity of the first molding tool and between a first molding portion and a second molding portion of the second molding tool.

In a preferred form, injecting molten plastic into the first and second molding tools may include forming the head having at least one flange extending radially outwardly from the first end of the plunger body and forming a cam follower on at least one flange.

In a preferred form, loading the plunger body into the cavity may include placing the plunger body over a vacuum slot formed in a wall of the first molding tool.

In a preferred form, the vacuum may be configured to adhere the plunger body to the molding tool.

In a preferred form, the method may include triggering an alarm when the plunger body is not loaded into the cavity.

In a preferred form, the vacuum may include a sensor communicatively coupled to the alarm and configured to signal the alarm when the sensor detects a condition of the plunger body and the cavity.

In a preferred form, forming the plunger body may include stamping a plurality of plunger bodies from blank of sheet metal.

In a preferred form, stamping the plurality of plunger bodies from the blank of sheet metal may include advancing the blank of sheet metal in a stamping machine.

In a preferred form, the blank of metal sheet may move between a plurality of stations in which the axial chamber of the plunger body is formed.

In a preferred form, forming the plunger body may include shaping a blank of sheet metal into a cylindrical shape with a body thickness of less than 0.6 millimeters.

In a preferred form, forming the plunger body may include cutting a corrugated edge into a blank of sheet metal and bending the corrugated edge such that the first end of the plunger body includes the corrugated edge bent outwardly relative to the axial chamber.

In a preferred form, forming the plunger body may include cutting a corrugated edge into a blank of sheet metal and bending the corrugated edge such that the second end of the plunger body includes the corrugated edge bent inwardly relative to the axial chamber.

In a preferred form, injecting molten plastic into the plurality of channels may include forming the head adjacent to the outer wall of the plunger body and coupling the head to the corrugated edge of the first end of the plunger body.

In a preferred form, injecting molten plastic into the plurality of channels may include forming the foot at least partially adjacent to the inner wall of the plunger body and coupling the foot to the corrugated edge of the second end of the plunger body.

In a preferred form, moving the first molding tool may include rotating a movable table at least 180 degrees, the first molding tool attached to a surface of the movable table.

In a preferred form, injecting molten plastic into the plurality of channels may include injecting molten plastic into the first and second molding tools.

In a preferred form, the plurality of channels may extend between the first molding portion and the second molding portion of the first molding tool and between a first molding portion and a second molding portion of the second molding tool.

In a preferred form, a vacuum component may be disposed in the middle portion of the cavity of the first molding tool.

In a preferred form, a sensor may be coupled to the vacuum component.

In a preferred form, the sensor may detect an absence of an object covering a slot of the vacuum component and to signal to a processor to activate an alarm.

In a preferred form, a curved channel may be formed in the second molding tool and may be in fluid connection with the second molding portion.

In a preferred form, the curved channel may have a diameter in a range of approximately 0.1 mm to approximately 0.3 mm.

In a preferred form, the first molding portion and the second molding portion of the first molding tool may be fluidly coupled by at least one of the plurality of channels.

In a preferred form, the first molding tool may be movable relative to the second molding tool between a first station and a second station.

In a preferred form, the second molding tool may be disposed at the second station.

In a preferred form, the first molding tool may rotate relative to the second molding tool.

In a preferred form, the second molding tool may move axially relative to the first molding tool such that the second molding tool moves towards the first molding tool when the first molding tool is disposed at the second station.

In a preferred form, the system may include a rotatable table where the first molding tool is coupled to the rotatable table.

In a preferred form, a third molding tool may be coupled to the rotatable table and spaced away from the first molding tool.

In a preferred form, the third molding tool may be substantially identical to the first molding tool.

In a preferred form, a slidable plate may be coupled to the first molding tool.

In a preferred form, the first molding tool may include a plurality of cavities and the second molding tool may include a plurality of cavities corresponding to the plurality of cavities of the first molding tool.

In a preferred form, the first molding portion of the first molding tool may be removably coupled to the first molding tool.

In a preferred from, the first molding portion of the second molding tool may be removably coupled to the second molding tool.

One aspect of the present disclosure provides a drug delivery device including a housing defining a longitudinal axis and having an opening and a drug storage container including a delivery member having an insertion end configured to extend at least partially through the opening during a delivery state. The device may further include a plunger moveable toward the distal end of the drug storage container to expel a drug from the drug storage container through the delivery member, the plunger including a plunger body having an inner wall defining an axial chamber and an outer wall cooperating with the inner wall to define a body thickness. The device may also include a plunger biasing member disposed at least partially within the axial chamber, the plunger biasing member configured to urge the plunger toward the distal end of the drug storage container.

The plunger body may have a hollow tubular shape. The plunger body may be made of metal or non-metal.

The plunger may be configured to selectively rotate from an initial rotational position to a second rotational position under a biasing force exerted by the plunger biasing member and to translate linearly toward the distal end of the drug storage container under the biasing force exerted by the plunger biasing member after rotating from the initial rotational position to the second rotational position.

The device may further include a plunger guide fixed relative to the housing, the plunger being disposed at least partially within the plunger guide. One of the plunger and the plunger guide may include a cam and the other one of the plunger and the plunger guide may comprises a cam follower.

The plunger may include the cam follower and the plunger guide includes the cam, and the cam follower may be formed by at least one flange extending radially outwardly from the plunger.

The plunger body thickness may be less than 0.6 millimeters, less than 0.4 millimeters, less than 0.3 millimeters, less than 0.2 millimeters, less than 0.1 millimeters, or less than 0.05 millimeters.

Another aspect of the present disclosure provides a drug delivery device including a housing defining a longitudinal axis and having an opening and a drug storage container including a delivery member having an insertion end configured to extend at least partially through the opening during a delivery state. The device may further include a plunger moveable toward the distal end of the drug storage container to expel a drug from the drug storage container through the delivery member, the plunger including a body portion having an inner wall defining an axial chamber and an outer wall cooperating with the inner wall to define a body thickness less than 0.6 millimeters. The device may also include a plunger biasing member coupled with the plunger and configured to urge the plunger toward the distal end of the drug storage container.

BRIEF DESCRIPTION OF THE DRAWINGS

FIG. 9A is a perspective view of an exemplary processing stage of the stamping system of FIG. 6;

FIG. 9B is a perspective view of a different exemplary processing stage of the stamping system of FIG. 6;

FIG. 9C is a top view of a completed plunger rod straw and hanger assembled using the stamping system of FIG. 6;

FIG. 11A is a side view of a blank metal sheet being processed in the stamping system of the present disclosure, showing stages 1-29 of the plunger rod straw during the stamping process;

FIG. 11B is a magnified side view of the processed metal sheet of FIG. 11A, showing stages 1-10 of the stamping process;

FIG. 19B is a top magnified view of a second end of the plunger rod straw disposed in a second molding portion of the first molding tool of FIG. 19A;

FIG. 19C is a top magnified view of a first end of the plunger rod straw disposed in the first molding portion of the first molding tool of FIG. 19A;

DETAILED DESCRIPTION

Figure 1:
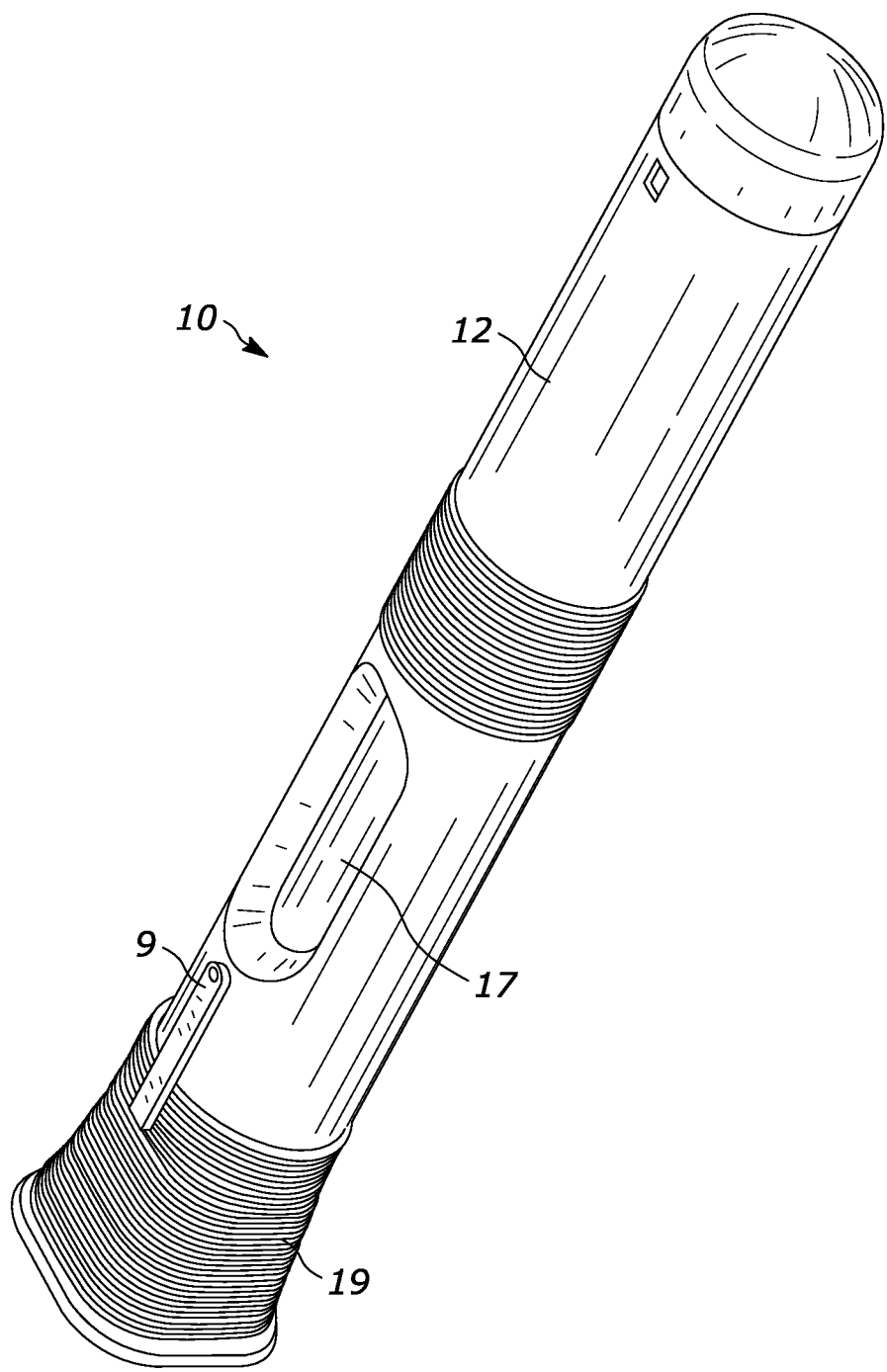
FIG. 1 is a perspective view of an exemplary drug delivery device in accordance with various embodiments.
Figure 2:
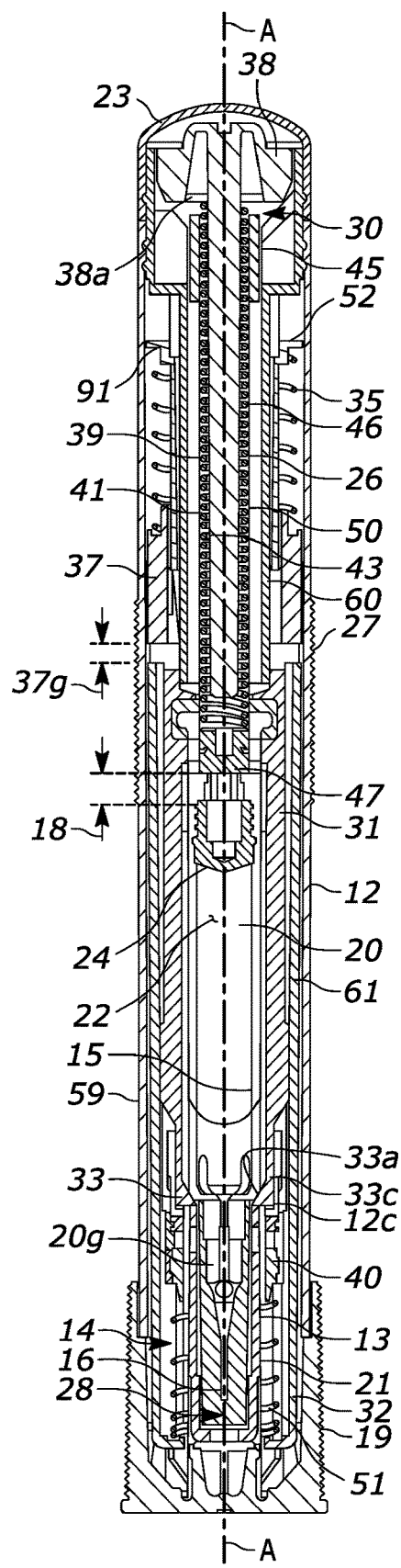
FIG. 2 is cross-sectional view of the drug delivery device in FIG. 1.

FIGS. 1-3 illustrate several views of an embodiment of a drug delivery device 10 for delivering a drug, which may also be referred to herein as a medicament or drug product. The drug may be, but is not limited to, various biologicals such as peptides, peptibodies, or antibodies. The drug may be in a fluid or liquid form, although the disclosure is not limited to a particular state.

Various implementations and configurations of the drug delivery device 10 are possible. The present embodiment of the drug delivery device 10 is configured as a single-use, disposable injector. In other embodiments, the drug delivery device 10 may be configured as multiple-use reusable injector. The drug delivery device 10 is operable for self-administration by a patient or for administration by a caregiver or a formally trained healthcare provider (e.g., a doctor or nurse). The exemplary the drug delivery devices shown in the figures may take the form of an autoinjector or pen-type injector, and, as such, may be held in the hand of the user over the duration of drug delivery, but may also or alternatively be suitable for other drug delivery devices and/or configurations.

As shown in FIG. 1, the drug delivery device 10 includes an outer casing or housing 12. The housing 12 may be pre-loaded with the drug storage container 20, e.g., by a manufacturer, or alternatively, loaded with the drug storage container 20 by a user prior to use of the drug delivery device 10. The drug storage container 20 may include a rigid wall defining an internal bore or reservoir. The wall may be made of glass or plastic. A stopper 24 may be moveably disposed in the drug storage container 20 such that it can move in a distal direction along the longitudinal axis A between a proximal end and a distal end of the drug storage container 20. The stopper 24 may be constructed of rubber or any other suitable material. The stopper 24 may slidably and sealingly contact an interior surface 15 of the wall of the drug storage container 20 such that a drug 22 is prevented or inhibited from leaking past the stopper 24 when the stopper 24 is in motion. Distal movement of the stopper 24 expels the drug 22 from the reservoir of the drug storage container 20 into the delivery member 16. The proximal end of the drug storage container 20 may be open to allow a plunger 26 to extend into the drug storage container 20 and push the stopper 24 in the distal direction. In the present embodiment, the plunger 26 and the stopper 24 are initially spaced from each other by a gap 18 (FIG. 2). Upon activation of a drive mechanism 30, the plunger 26 moves in the distal direction to close the gap and comes into contact with the stopper 24. Subsequent distal movement of the plunger 26 drives the stopper 24 in the distal direction to expel the drug 22 from the drug storage container 20. In alternative embodiments, the stopper 24 and the plunger 26 may initially be in contact with one another or coupled to one another, e.g., via a threaded coupling, such that they move together jointly from the start of movement of the plunger 26. Once the stopper 24 is in motion, it may continue to move in the distal direction until it contacts a proximally-facing portion of the interior surface 15 of the wall of the drug storage container 20. This position of the stopper 24 may be referred to as the end-of-dose or end-of-delivery position, and may correspond to when delivery of the drug 22 to the patient is complete or substantially complete.

In some embodiments, the housing 12 may be sized and dimensioned to enable a person to grasp the injector 10 in a single hand. The housing 12 may have a generally elongate shape, such as a cylindrical shape, and extends along a longitudinal axis A between a proximal end and a distal end. An opening 14 (FIG. 3B) may be formed in the distal end to permit an insertion end 28 of the delivery member 16 (FIG. 2) to extend outside of the housing 12. A transparent or semi-transparent inspection window 17 (FIG. 1A) may be positioned in a wall of the housing 12 to permit a user to view component(s) inside the drug delivery device 10, including a drug storage container 20. A removable cap 19 may cover the opening 14 prior to use of the drug delivery device 10, and, in some embodiments, may including a gripper 13 (FIG. 2) configured to assist with removing a sterile barrier 21 (e.g., a rigid needle shield (RNS), a non-rigid needle shield (nRNS), etc.) mounted on the insertion end 28 of the delivery member 16.

Figure 3A:
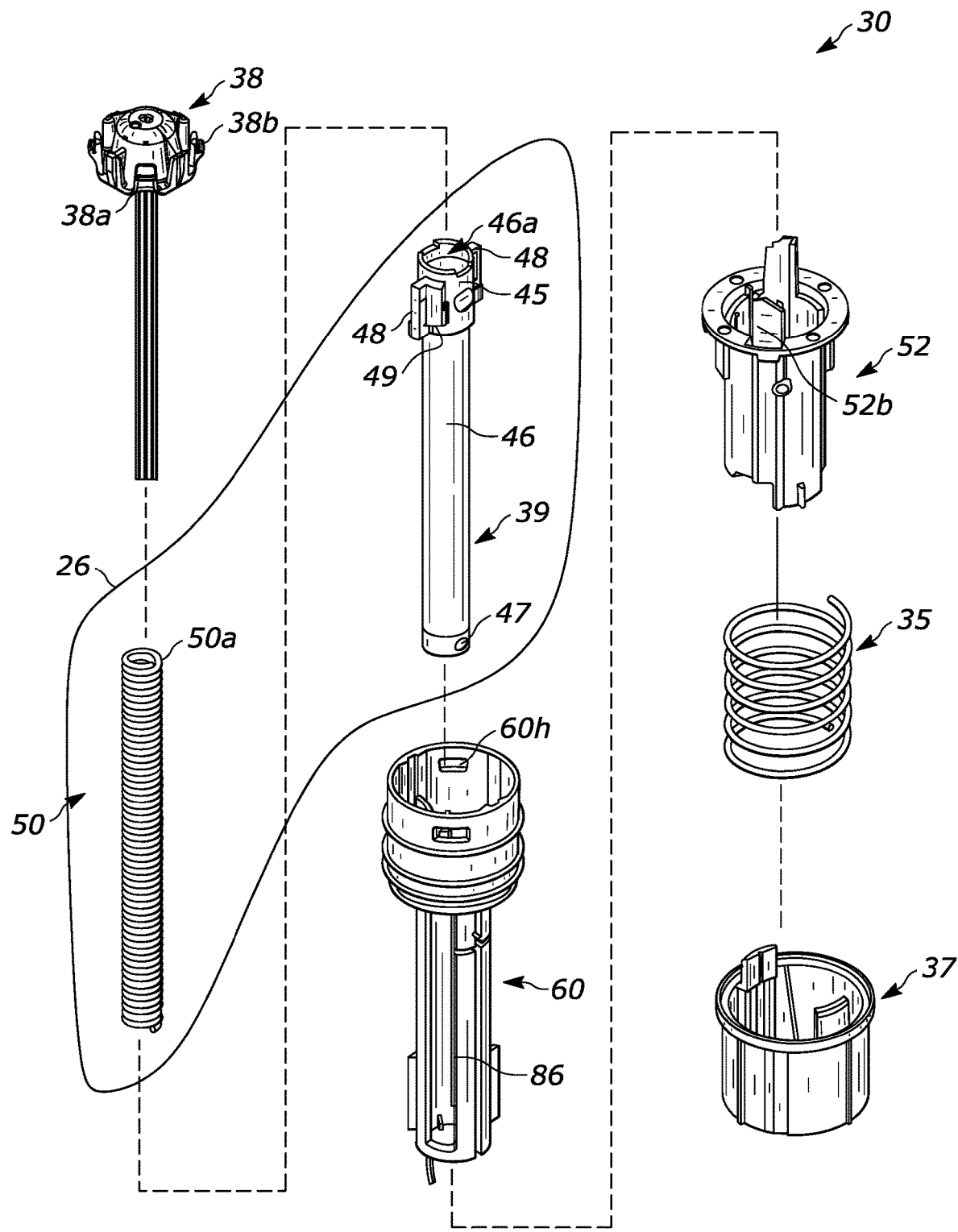
FIG. 3A is an exploded assembly view of a portion, namely the drive mechanism, of the drug delivery device in FIG. 2.

As shown in FIG. 2, the drive mechanism 30 may be disposed partially or entirely within the housing 12. Generally, the drive mechanism 30 may be configured to store energy and, upon or in response to activation of the drive mechanism 30 by the user, release or output that energy to drive the plunger 26 to expel the drug 22 from a drug storage container 20 through the delivery member 16 into the patient. In the present embodiment, the drive mechanism 30 is configured to store mechanical potential energy; however, alternative embodiments of the drive mechanism 30 may be configured differently, for example, with the drive mechanism 30 storing electrical or chemical potential energy. Generally, upon activation of the drive mechanism 30, the drive mechanism 30 may convert the potential energy into kinetic energy for moving the plunger 26. As best illustrated in FIG. 3A, in one embodiment, the drive mechanism 30 includes a plunger biasing member 50, a hollow rod 46 for supporting the plunger biasing member 50, a plunger biasing member seat 38, a releaser member 52, a plunger guide 60, an extender biasing member 35, and a guard extension 37. The plunger biasing member 50 may include a compression spring (e.g., a helical compression spring) which is initially retained in an energized state within a bore of the plunger 26. In the energized state, the plunger biasing member 50 may be compressed such that its axial length is shorter than it would be in a natural or de-energized state. When released, the plunger biasing member 50 may try to expand to its natural axial length, and as a consequence, exert a biasing force pushing the plunger 26 in the distal direction.

Figure 3B:
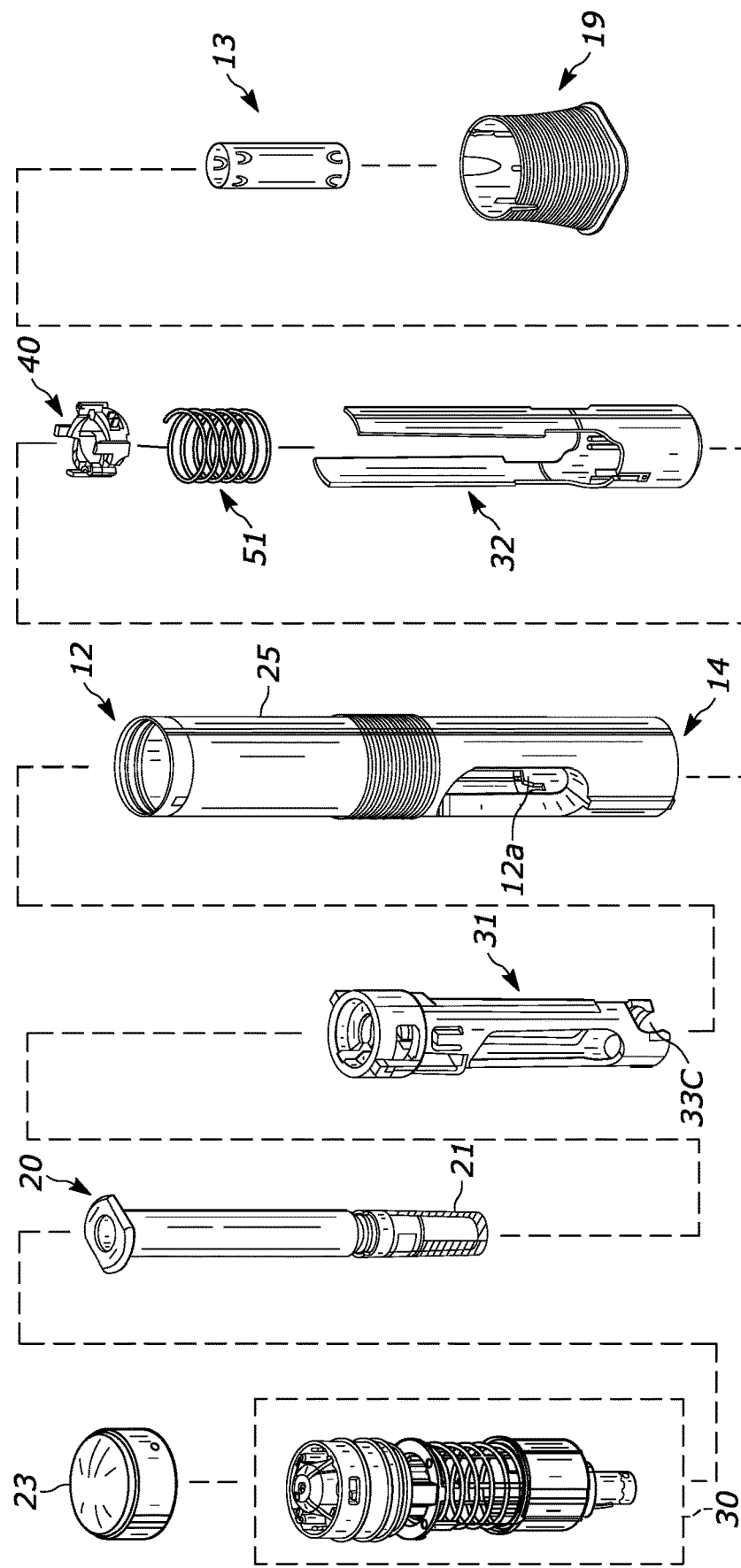
FIG. 3B is an exploded assembly view of the drug delivery device in FIG. 2.

As best shown in FIGS. 2 and 3B, the housing 12 may include two separate and interconnected structures: a rear end cap 23 (e.g., a rear cover) at the proximal end of the drug delivery device 10; and a tubular housing 25 extending substantially completely along the length of the drug delivery device 10 and defining the opening 14. Additionally or alternatively, the housing 12 may include fewer or more components, such as a two-piece tubular housing having front and rear portions. The tubular housing 25 may have a hollow and generally cylindrical or tubular shape, and the rear end cap 23 may have a generally hemispherical shape or a hollow cylindrical shape with an open end and a closed off end. In some embodiments, the rear end cap 23 and the tubular housing 25, and any components to be positioned therein, may be assembled together to define different sub-assemblies, such as the drive mechanism 30 (FIG. 3A). In some embodiments, the different sub-assemblies are assembled independently of each other and then later combined with one another, as well as with the drug storage container 20, to form the fully-assembled drug delivery device 10. In certain such embodiments, some or all of the foregoing phases of assembly may occur in different manufacturing facilities or environments. In alternative embodiments, the housing 12 may be constructed in one piece, such that the housing 12 is defined by a single, monolithic structure that integrates a rear cap and tubular housing in a single component.

In one embodiment, a container holder 31 secures and/or fixes the position of the drug storage container 20 within the housing 12. For example, the container holder 31 may be configured to support the drug storage container 20, with respect to the housing 12, proximal to at least a portion of the distal end of the body portion of the drug storage container 20 (including, for example, proximal to an entirety of the distal end of the body portion of the drug storage container 20) such that a resultant force acting on the drug storage container 20 from the plunger biasing member 50 is at least substantially completely borne by the distal end of the body portion of the drug storage container 20. The container holder 31 may have a hollow and generally cylindrical or tubular shape centered about the longitudinal axis A, and the drug storage container 20 may be disposed partially or entirely within the container holder 31. A distal end of the container holder 31 may include an inwardly protruding flange 33 abutting against a shoulder portion 20a of the drug storage container 20, thereby preventing distal movement of the drug storage container 20 during actuation of the plunger 26.

The term "resultant force" refers to force the urging the drug storage container 20 along the axis A upon and due to actuation of the plunger biasing member 50 during and after the injection state. For example, when the plunger 26 is actuated and driven in the distal direction along axis A, it urges the stopper 24 in the distal direction. As a result of this direct contact between the plunger 26 and the stopper 24, as well as frictional forces between the stopper 24 and the drug storage container 20 and the forces required to urge the drug 22 through the relatively small-diameter delivery member 16, the drug storage container 20 is urged in a distal direction even though the plunger 26 may not directly touch, abut, or engage the body portion of the drug storage container 20. As a result, the drug storage container 20 may experience a relatively high resultant force during the injection process, more specifically during the actuation of the plunger 26.

Figure 4A:
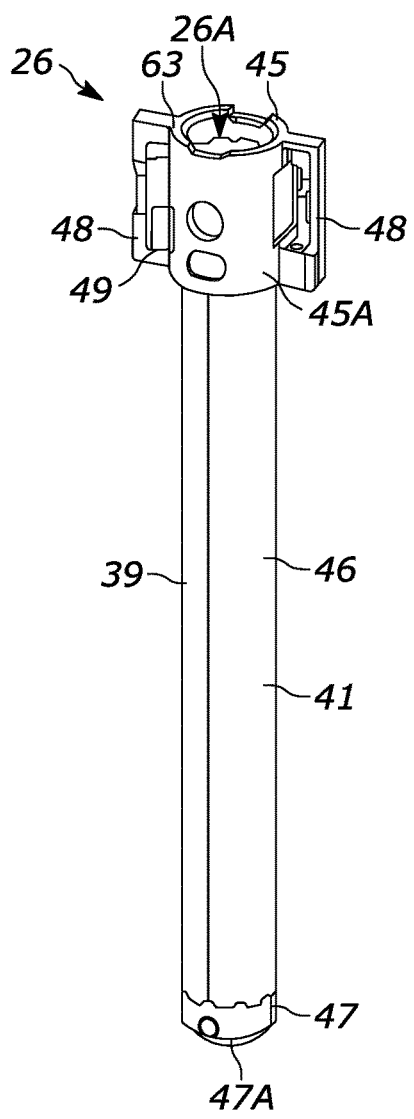
FIG. 4A is a perspective view of a plunger rod manufactured in accordance with the systems and methods disclosed herein.
Figure 4B:
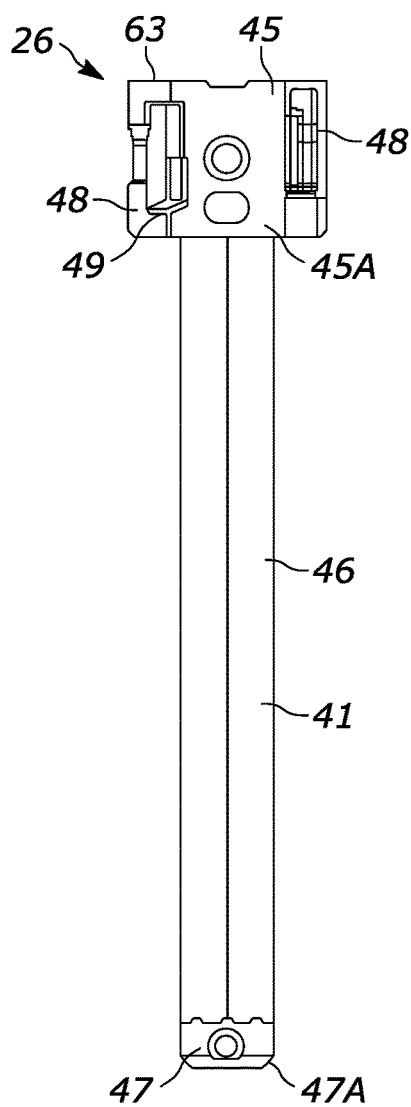
FIG. 4B is a front view of the plunger rod of FIG. 4A.
Figure 4C:
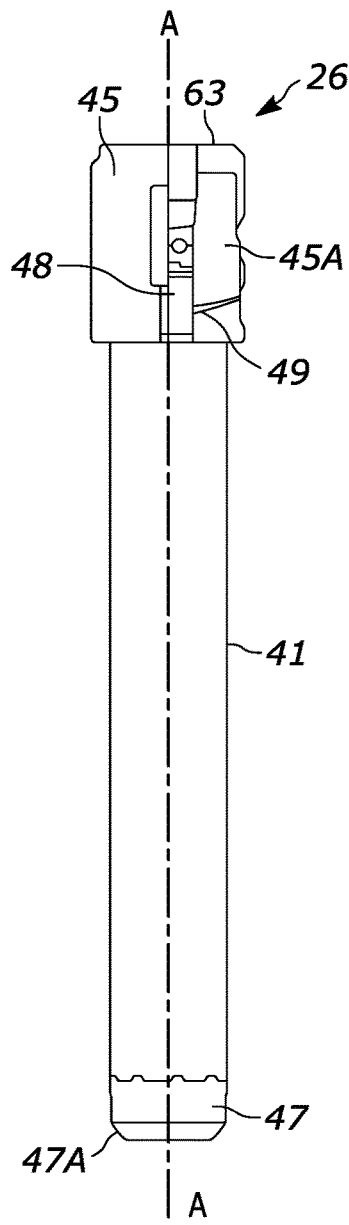
FIG. 4C is a side view of the plunger rod of FIG. 4A.
Figure 4D:
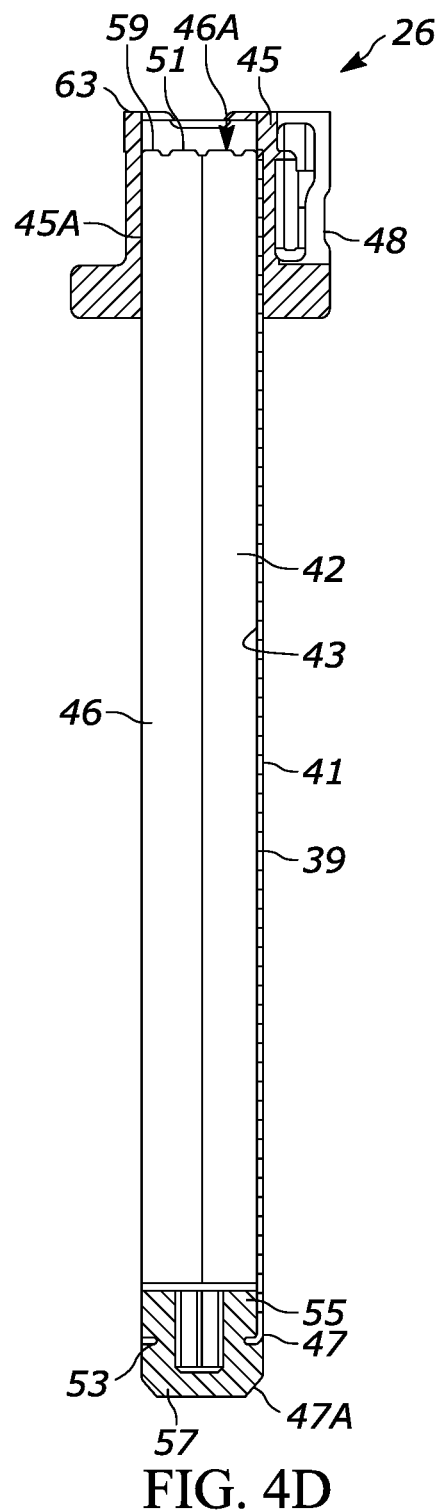
FIG. 4D is a cross-sectional view of the plunger rod of FIG. 4C taken through line D-D.
Figure 4E:
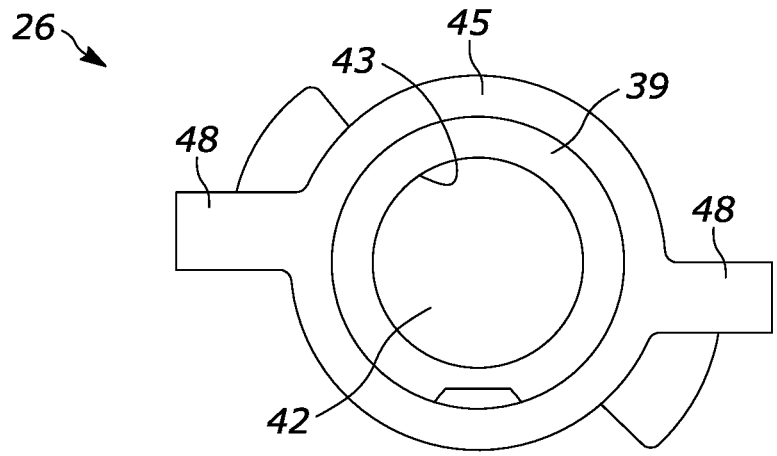
FIG. 4E is a top view of the plunger rod of FIG. 4A.

As best illustrated in FIGS. 4A-4E, the plunger 26 may have a hollow and generally cylindrical or tubular shape. The plunger 26 may include an annular wall 39 with an outer surface 41 and an inner surface 43. The inner surface 43 may define an interior space 42 (as shown in FIG. 4E, and also referred herein as an "axial chamber") sized to receive a plunger biasing member 50 therein. It is generally desirable to minimize a thickness of the annular wall 39, to the extent possible and without compromising the integrity of the plunger 26, so as to maximize an inner diameter of the plunger 26. This allows a larger diameter plunger biasing member 50 to fit within the interior space of the plunger 26, which, in turn, allows for a more powerful plunger biasing member 50. As a more specific example, the thickness of the annular wall 39 may be less than 2 mm. As another more specific example, the thickness of the annular wall may be less than 1 mm. As another more specific example, the thickness of the annular wall may be less than 0.6 mm. As another more specific example, the thickness of the annular wall may be less than 0.3 mm. As another more specific example, the thickness of the annular wall may be less than 0.2 mm. As another more specific example, the thickness of the annular wall may be less than 0.1 mm. As another more specific example, the thickness of the annular wall may be less than 0.05 mm. The annular wall 39 may be made of any suitable material, such as metal or plastic. It may be advantageous for the annular wall 39 to be made of metal, such as steel or aluminum, for the purposes of minimizing the thickness of the annular wall 39. For example, a metal annular wall 39 may have sufficient axial strength and/or buckle resistance for use in the device if the annular wall 39 thickness is greater than 0.05 mm. Conversely, a plastic annular wall 39 may have sufficient axial strength and/or buckle resistance for use in the device if the annular wall 39 thickness is greater than 1 mm.

The hollow rod 46 may additionally or alternatively facilitate and/or provide more flexibility in spring design. For example, it may be desirable or advantageous to use the device with different springs depending on the characteristics of the drug and/or the desired drug delivery profile. For example, a higher viscosity drug may require a spring with a higher spring rate and/or spring force and it thus may be desirable or advantageous to have flexibility in physical characteristics of the spring. As a more specific example, various physical characteristics of a spring may affect the spring rate, and thus the spring force, such as wire diameter of the spring (typically increasing the wire diameter increases the spring rate), mean diameter of the spring (typically increasing the mean diameter decreases the spring rate), the number of spring coils (typically increasing the number of coils increases the spring rate), and the spring material. These physical characteristics may be adjusted to deliver different spring rates, while also potentially adjusting the thickness of the hollow rod 46, to maintain a constant or relatively constant outer diameter of the overall plunger 26 so as to keep constant the remaining parts of the device, such as the plunger guide 60 and the stopper 24. The hollow rod 46 may additionally or alternatively facilitate and/or provide more longitudinal stability for the plunger biasing member 50, such as by preventing or reducing buckling or other transverse movement.

The plunger biasing member 50 (as shown in FIGS. 2 and 3A) may include the following dimensions: 0.65 mm wire diameter, 5.40 mm outer diameter of the spring, and 80 to 86 number of coils (depending on pitch), but other suitable spring characteristics may be utilized. The plunger biasing member 50 shown in the figures may be formed of stainless steel strength 2300 n/mm, but other suitable materials may be utilized. The hollow rod 46 shown in the figures may include the following dimensions and materials: 63 mm length, 6 mm outer diameter, 0.20 mm wall thickness, and stainless steel strength 600 to 750 n/mm material, but other suitable dimensions and materials may be utilized.

As described below in more detail, the plunger 26 may be configured to selectively rotate relative to the housing 12 and translate linearly relative to the housing 12 during operation of the drug delivery device 10.

Turning again to FIGS. 4A-4E, the plunger 26 may be constructed of multiple, interconnected pieces, or alternatively, have a one-piece construction. In the present embodiment, the plunger 26 is constructed of three separate and interconnected structures: a top ring 45 (also referred herein as a "head" or "head portion") defining a proximal end of the plunger 26; a base 47 (also referred herein as a "foot" or "foot portion") defining a distal end of the plunger 26; and a hollow rod 46 (also referred herein as a "plunger body") positioned between and rigidly connecting the top ring 45 and the base 47. The positions of the top ring 45, the hollow rod 46, and the base 47 may be fixed relative to each other such that these components are immoveable relative to each other. The top ring 45, the hollow rod 46, and the base 47 may each have an annular construction and be centered about the longitudinal axis A. The top ring 45 and the hollow rod 46 may each have a respective central opening 46a extending from end to end of the component to define an axial chamber 42; whereas, the base 47 may have a central opening extending through the proximal end of the base 47 but which is closed off at the distal end of the base 47. The closed off end of the base 47 may define seat or abutment surface for the plunger biasing member 50. In alternative embodiments, the central opening may extend through the base 47 from end to end. In such alternative embodiments, an inner diameter of the central opening of the base 47 may be smaller than an outer diameter of the plunger biasing member 50 such that the base 47 retains a distal end of the plunger biasing member 50 within the plunger 26. When the drive mechanism 30 is activated, the base 47 may be the portion of the plunger 46 that comes into contact with the stopper 24 to push the stopper 24 in the distal direction.

The top ring 45 at least partially surrounds a proximal or first end 59 of the plunger body 46. The top ring 45 is formed around an outwardly bent corrugated edge 51. As shown in FIG. 4D, a proximal end 63 of the top ring 45 extends above and around the corrugated edge 51 of the proximal end 63 of the plunger body 46. As such, the top ring 45 is secured in place relative to the plunger body 46. The top ring 45 may include one or more flanges or projections 48 which extend radially outwardly from a central portion or collar 45A of the top ring 45. Each of the projections 48 may include a distally facing camming surface 49. As described below in more detail, the distally facing camming surface 49 may interact with a counterpart camming surface on a plunger guide 60 in order to release the plunger biasing member 50. The camming surfaces permit a smoother insertion of the plunger 26 during assembly of the device 10. In some embodiments, the distally facing camming surface 49 may be arranged at an angle relative to, or is otherwise non-parallel to, an imaginary plane perpendicular to the longitudinal axis A.

The base 47 extends from a distal or second end 61 of the plunger body 46 and is partially disposed in the axial chamber 42 of the plunger body 46. As shown in FIGS. 4C and 4D, the base 47 is formed around an inwardly bent corrugated edge 53 of the plunger body 46. The base 47 has a first portion 55 that is disposed within the axial chamber 42 of the plunger body 46 and a second portion 57 that extends away from the distal end of the plunger body 46. A diameter of the first portion 55 may be slightly less than a diameter of the second portion 57. However, because the base 47 is formed around the corrugated edge 53 of the distal end of the plunger body 46, the base 47 is secured in place relative to the plunger body 46. The second portion 57 has a distal chamfered portion 47A, which acts as a barrier between the metal plunger body 46 and the glass of the syringe. As such, the plunger 26 does not contact the glass of the syringe as the plunger 26 moves through the medical device 10.

As will be described in more detail below, the top ring 45 and/or the base 47 may be constructed of a different material than the hollow rod 46. In some embodiments, the top ring 45 and/or the base 47 made be constructed of plastic whereas the hollow rod 46 may be constructed of metal. So configured, the plastic material used for the top ring 45 may facilitate the camming action described below by providing a relatively low coefficient of friction, the plastic material used for the base 47 may help absorb or attenuate any shock or vibrations associated with base 47 striking the stopper 24. The metal material used for the hollow rod 46 may provide sufficient rigidity to avoid buckling under the biasing force exerted by the plunger biasing member 50. In alternative embodiments, the top ring 45, hollow rod 46, and/or base 47 may be made of the same material, including, for example, metal or plastic. In certain such embodiments, the top ring 45, hollow rod 46, and base 47 may be integrally formed in one piece so as to define single, monolithic structure.

As discussed above, the plunger biasing member 50 may be disposed at least partially within the plunger 26, and may have a distal end abutting against a proximally facing inner surface of the plunger 26 and/or may be fixedly attached to an inner surface of the plunger 26. So that the plunger biasing member 50 may be received within the plunger 26, an outer diameter or other dimension of the plunger biasing member 50 may be equal to or less than an inner diameter of the top ring 45 and/or equal to or less than an inner diameter of the hollow rod 46. In some embodiments, the distal end of the plunger biasing member 50 may abut against a proximally facing inner surface of the base 47 of the plunger 26. Furthermore, as best illustrated in FIGS. 2 and 3A, a proximal end 50a of the plunger biasing member 50 may abut against a distally facing surface 38a of the plunger biasing member seat 38. The plunger biasing member seat 38 may be fixedly attached to the rear housing 27 such that the plunger biasing member seat 38 provides a stationary surface for the plunger biasing member 50 to push off of. For example, as shown in FIG. 3A, the plunger seat 38 may include flanges 38b that are received within openings 60h formed in a proximal portion of the plunger guide, thereby fixedly coupling the plunger seat to the plunger guide 60. So configured, the plunger biasing member 50, when released from the energized state, may expand in length with distal end of the plunger biasing member 50 moving in the distal direction away from the stationary proximal end of the plunger biasing member 50. This motion may push the plunger 26 is the distal direction, which, in turn, may push the stopper 24 in the distal direction to expel the drug 22 from the drug storage container 20 into the delivery member 16 and thereafter into the patient. However, in the embodiment shown in the figures, neither the release of the plunger biasing member 50 nor any other biasing members cause the delivery member 16 to drive downward with respect to the housing 12. On the contrary, the drug product container 20, and as a result the delivery member 16, is substantially or completely fixedly coupled with respect to the housing 12. Rather, the delivery member 16 is driven into the patient's skin 5 by inertial force generated by a downward force by the patient (or a health care provider or other person administering the dose).

As illustrated in FIG. 2, the releaser member 52 may be radially positioned between the plunger guide 60 and the guard extension 37. The releaser member 52 is also radially positioned between the guard extension 37 and the plunger guide 60. Furthermore, the extender biasing member 35 may be axially positioned between the releaser member 52 and the guard extension 37 and may be radially arranged around the releaser member 52. Generally, the releaser member 52 is configured to: (1) operably couple the guard member 32 and the plunger 26 in an activation sequence and (2) generate an audible signal indicating the end of drug delivery. So configured, the releaser member 52 is exploited to perform two separate functions, and thus reduces the number of moving parts required by the drug delivery device 10.

As shown in FIG. 3A, the releaser member 52 includes a channel surface 52b that extends proximally past the proximal-most (e.g., top) surface of the tubular body of the releaser member 52. For example, the releaser member 52 includes a proximally facing contact surface and the channel surfaces 52b each extend past the contact surface so as to provide a continuous path with respect for the top ring 45 while also permitting a sufficient gap between the proximally facing contact surface and the corresponding surface involved in end-of-dose notification. The channel surfaces 52b of the releaser member 52 are each configured to receive the projections 48 of the top ring 45 and permit axial movement of the plunger 26 with respect to the releaser member 52 but to resist or prevent rotational movement between the plunger 26 and the releaser member 52. As shown in FIG. 3A, although the channel surface 52b extends adjacent to the inner surface of the releaser member 52, the channel surface 52b does not have an arcuate shape and instead has a generally squared-off shape.

Several of the device components include various features, surfaces, and openings for interacting with and controlling the release movement of the plunger 26 (e.g. the injection sequence). Generally, the injection sequence begins with retraction/axial movement of the guard member 32 in the proximal direction (upward in FIG. 2), which causes axial movement of the guard extension 37, which unlocks the releaser member 52. Once the releaser member 52 is unlocked (e.g. first stage of travel), the plunger 26 and the plunger biasing member 50 urge the releaser member 52 to rotate clockwise and permit axial movement of the plunger 26 (in the distal direction, downward in FIG. 2). The plunger then urges the stopper 24 in the distal direction, thereby urging the drug 22 from the drug product container 20 and out of the delivery member 16. Once the plunger has reached a certain point along the axial length of the device, movement of the releaser member 52 is further unlocked (e.g. second stage of travel) and the releaser travels in the proximal direction (upward in FIG. 2) and into contact with the plunger guide 60, thereby generating an end-of-dose indication (such as an audible click). The injection sequence will now be described in more detail.

As described below in more detail, the plunger 26 may be configured to selectively rotate relative to the housing 12 and translate linearly relative to the housing 12 during operation of the drug delivery device 10.

In the pre-delivery state prior to retraction of the needle guard 32, the plunger 26 and the releaser member 52 each may be arranged in a respective initial rotational position. The plunger biasing member 50 may be in an energized state. As a consequence, the plunger biasing member 50 may exert a distally directed biasing force on the plunger 26 which urges the distally facing camming surface 49 against a proximally facing camming surface of the plunger guide 60. A resulting camming action may urge the plunger 26 to rotate in the clockwise direction. Despite these biasing force(s), neither the releaser member 52 nor the plunger 26 rotates in the pre-delivery state. This is because the releaser member 52 and the plunger are rotationally fixed in the pre-injection state. Accordingly, the releaser member 52, plunger guide 60, the guard extension 37, and the housing 12 work in conjunction with one another to retain the plunger biasing member 50 in the energized state prior to retraction of the guard member 32, as is now described in more detail.

As best shown in FIG. 2, as the guard member 32 travels in the proximal direction (upward in FIG. 2), the proximal end of the guard member 32 contacts a distally-facing surface of the guard extension 37 and urges the guard extension in the proximal direction. When the device is in the pre-injection stage, as shown in FIGS. 2, a locking flange of the guard extension 37 engages a locking flange of the releaser member 52, thereby rotationally locking the releaser member 52. At this point in the sequence, the distally facing camming surface 49 of top ring 45 of the plunger 26 is abutting against a proximally facing camming surface of the plunger guide 60 such that the plunger 26 is restrained from axial travel due to this interaction. The distally facing camming surface 49 and/or the proximally facing camming surface includes a sloped surface to promote relative movement of the plunger 26 top ring 45 in a clockwise direction. For example, the distally facing camming surface 49 has a slope of approximately 10 degrees but may have any suitable slope such as 9 to 11 degrees, 8 to 12 degrees, 7 to 13 degrees, 6 to 14 degrees, 5 to 15 degrees, 4 to 16 degrees, or any other suitable slope. Additionally or alternatively, the distally facing camming surface 49 of top ring 45 may have a slope 49a of approximately 10 degrees but may have any suitable slope such as 9 to 11 degrees, 8 to 12 degrees, 7 to 13 degrees, 6 to 14 degrees, 5 to 15 degrees, 4 to 16 degrees, or any other suitable slope. The slope(s) on one or more of the respective surfaces 49 causes the axial force from the plunger biasing member 50 to generate a force in the transverse direction, thereby urging the plunger 26 top ring 45 in the clockwise direction. However, as discussed above, the releaser member 52 resists or prevents rotational movement between the releaser member 52 and the plunger while the top ring 45 is positioned within and/or contacting the channel surface 52b. As a result, as long as the guard extension 37 is rotationally locking the releaser member 52 (as shown in FIG. 2), then the top ring 45 will remain rotationally locked by the channel surface 52b and axially locked by the proximally facing camming surface of the plunger guide 60.

The unlocking stage of the injection sequence is when the guard extension 37 translates in the proximal direction until the guard extension 37 locking flange no longer engages the locking flange of the releaser member 52 and the releaser is no longer rotationally locked. At this stage, two things happen simultaneously or near simultaneously: (1) the guard biasing member 35 urges the releaser member 52 in the clockwise direction and upward due to a camming surface on one or both of the inner surface of the releaser member 52 or the outer surface of the plunger guide 60 that translates the axial force from the guard biasing member 35 into a transverse (clockwise) force and causes the releaser member 52 to rotate clockwise and move upward (proximally) and (2) the plunger biasing member 50 urges the top ring 45 in the clockwise direction and downward (distally) due to the camming action between surfaces of the plunger 26 and the plunger guide 60 thereby causing the plunger 26 to move clockwise and slightly downward along ramped surface of the plunger guide 60. In other words, the releaser member 52 and the plunger 26 top ring 45 are both rotating clockwise at the same time or substantially the same time, due to forces from respective biasing members 35, 50. This sliding motion between surfaces of the plunger 26 and the plunger guide 60 results in rotation, as well as linear translation (not unlike a spiral pathway). Accordingly, the plunger guide 60 may function as a cam and the plunger rod 26 the cam follower.

In a downward stroke stage, the top ring 45 is still visible near the proximal portion of the plunger guide 60, but it will quickly travel along a longitudinal slot 86 (FIG. 3A) formed in the plunger guide 60 and the channel surface 52*b* of the releaser member 52. During this stage, the plunger 26 top ring 45 is traveling along both the channel surface 52*b* of the releaser member 52 and the longitudinal slot 86 of the plunger guide 60, thereby preventing rotation between any of the three components (26, 52, 60). As a more specific example, because the plunger guide 60 is rotationally fixed with respect to the housing 12, while the top ring 45 is positioned within both the channel surface 52*b* and the longitudinal slot 86, the releaser member 52 is unable to rotate. Also during this stage, as the plunger 26 travels distally, the gap 18 (FIG. 2) between the base 47 of the plunger 26 and the stopper 24 shrinks and the base 47 contacts the stopper 24. The device 10 is designed such that plunger 26 is traveling with a force sufficient to drive the stopper 24 in the distal direction and urge the drug 22 from the delivery member 16. At the same time, the device 10 is also designed such as to reduce or eliminate the likelihood of glass breakage, undesirable forces acting on the patient, and/or undesirable impact vibration or sound due to interaction between the base 47 and the stopper 24. For example, the plunger biasing member 50 design parameters may be designed to meet these two sets of design goals. As another example, a damping component may be positioned between the base 47 and the stopper 24 or in another location in the device 10 to dampen the forces between the base 47 and the stopper 24. For example, the base 47 may include an elastomeric component, section, or other damping feature. Additionally or alternatively, the stopper 24 may be formed of an elastomeric material that includes inherent damping properties. Additionally or alternatively, the stopper 24 may include an additional elastomeric component, section, or other damping feature.

In some embodiments, the camming action between the distally facing camming surface 49 on the projection 48 and the proximally facing camming surface of the plunger guide 60 may provide a damping effect. More particularly, a sliding friction between these two surfaces may be selected to slow initial expansion of the plunger biasing member 50. As a consequence, the velocity of the plunger 26 may be reduced during the initial expansion of the plunger biasing member 50, as compared to free uninhibited expansion of the plunger biasing member 50. The reduced velocity of the plunger 26 may cause the plunger 26 to strike the stopper 24 with less force, which reduces the chances of structural damage to the drug storage container 20 and/or facilitates a more comfortable injection for the user.

As discussed above, during the downward stroke stage, while the top ring 45 is positioned within the channel surface 52*b* and the longitudinal slot 86, the releaser member 52 is unable to rotate with respect to the plunger guide 60. However, in the end-of-dose initiation stage, the top ring 45 in some embodiments may clear the distal end of the releaser member 52 and no longer restricts or prevents rotation of the releaser member 52. As a more specific example, as the top ring 45 exits the channel surface 52*b* and/or a distal surface of the releaser member 52, the releaser member 52 is no longer rotationally constrained by the top ring 45 and the releaser member 52 is urged upward by the guard biasing member 35. As a result of the upward force of the guard biasing member 35 and camming surfaces, the releaser member 52 rotates clockwise while it moves upward in a spiral like path and a proximal facing surface of the releaser member 52 contacts a distal facing surface of the plunger guide 60, thereby making an audible click sound. The length of the channel surface 52*b* and plunger 26 may be designed so that the top ring 45 exits the channel surface 52*b* as the stopper 24 reaches a desired point of travel within the drug storage container 20, such as its end of travel near the distal end of the drug storage container 20.

Figure 5:
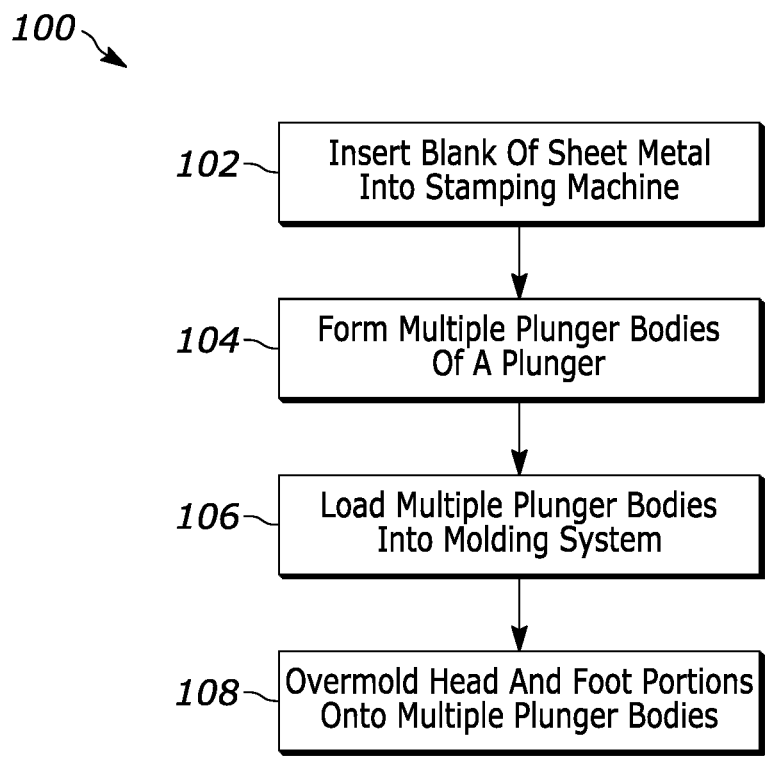
FIG. 5 is a schematic diagram of an exemplary method of manufacturing the plunger rod of FIG. 4A in accordance with the systems and methods disclosed herein.

A method 100 of manufacturing the plunger 26 of the device 10 in FIGS. 1-4E is shown in FIG. 5 and described in accordance with the teachings of the present disclosure. The method 100 of manufacturing the plunger may be described in two main phases: a stamping phase (steps 102, 104) where a stamping machine forms and shapes the plunger body (FIGS. 6-13) from a blank of sheet metal, and a molding phase (steps 106, 108) where an injection molding system molds the head and foot 45, 47 onto the plunger body 46 (FIGS. 14-24B) of the plunger 26. The plunger 26 of FIGS. 4A-4E is manufactured according to the two phases described below. However, the plunger 26 may be manufactured using a different method that incorporates one or both phases.

Generally, the first phase of the method 100 of manufacturing the plunger 26 of FIGS. 4A-4E includes forming a plunger body from a blank of sheet metal. Initially, a first step 102 includes inserting a blank of sheet metal into a stamping machine, and a subsequent step 104 includes forming a plurality of plunger bodies from that sheet metal. A plurality of stamping dies of the stamping machine gradually shapes the blank of sheet metal (or "workpiece" at a given location) into a cylindrical shape in a series of stages. The cylindrical workpieces, now finished plunger bodies, exit the stamping machine and are separated from the metal sheet or previously separated by the stamping machine. In step 106, an operator or robot loads a plurality of plunger bodies onto an injection molding system. In step 108, the molding system injects molten plastic into first and second molds to overmold the plunger bodies to form the head 45 and foot 47 components of onto each plunger body. The overmolded plunger bodies are cooled before being removed from the molding system, finished, and assembled with a drug delivery device, such as the device 10 of FIGS. 1-3B. As used herein, the term "blank of sheet metal" or "sheet metal" refers to a length of metal used in the stamping machine for forming into the plunger bodies. The term may refer to the metal before, during, or after it is inserted and shaped in the stamping machine. Therefore, the blank of sheet metal may have a variety of features, including multiple workpieces at various stages of the stamping process, perforations to facilitate advancement through the machine, and/or bends, dimples, corrugations, embossing, etching, etc.

Figure 6:
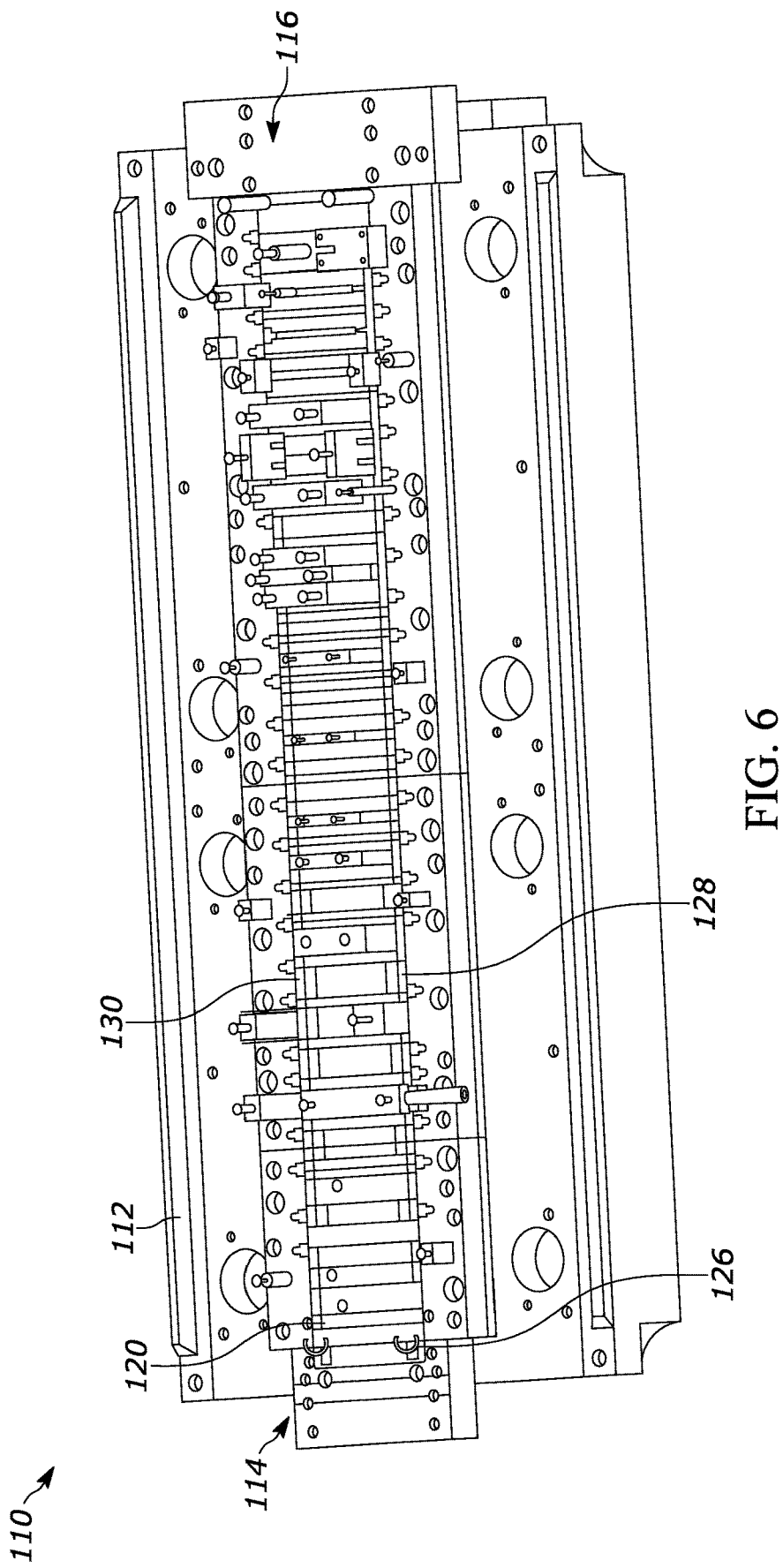
FIG. 6 is a top perspective view of a stamping system constructed in accordance with the teachings of the present disclosure, the stamping system for manufacturing a plurality of plunger rod straws.
Figure 7:
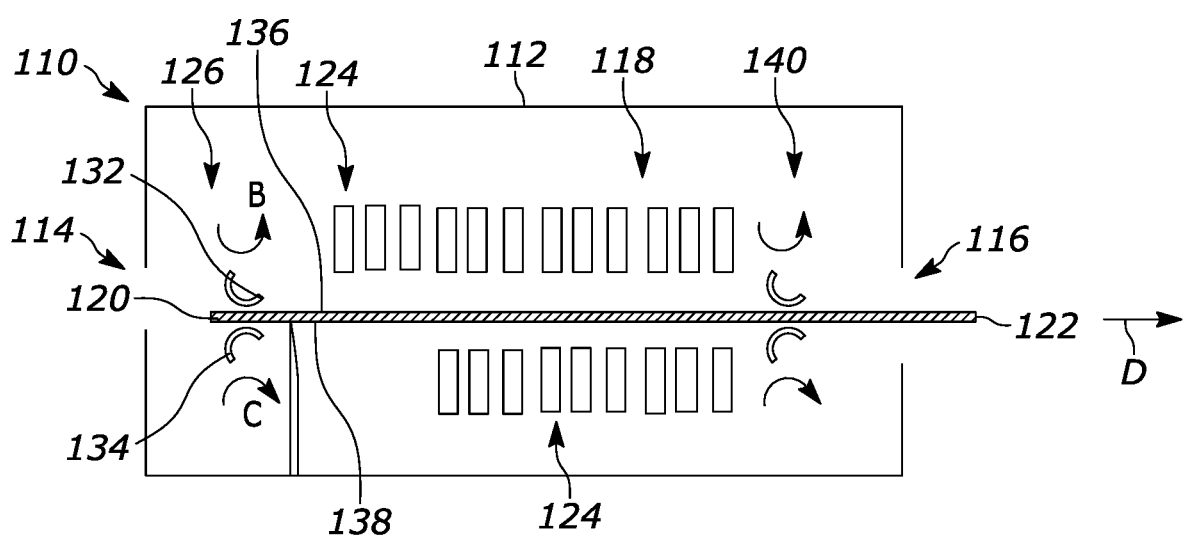
FIG. 7 is a side schematic view of a blank of sheet metal moving through the stamping system of FIG. 6.

In FIGS. 6 and 7, an exemplary stamping machine 110 used to complete the first phase of the manufacturing process 100 is constructed in accordance with the teachings of the present disclosure. The stamping machine 110 includes a housing 112, which is partially hidden in FIG. 6 to illustrate in the stamping machine 110 interior components. The machine 110 includes an inlet 114, an outlet 116, and a travel path 118 that extends between the inlet 114 and the outlet 116. According to step 102 of the method 100, an operator (or robot) inserts a blank of sheet metal 120 in the inlet 114 of the machine 110 to convey the metal sheet 120 along the travel path 118. As the metal sheet 120 travels through machine 110, a plurality of stamping tools or dies perform step 104 and impact a central portion or workpiece of the metal sheet 120 to shape the metal into a plunger body. Before exiting through the outlet 116 of the machine 110, the metal sheet 120 includes a workpiece having a cylindrical plunger body. After separating the workpiece from the metal sheet 120, which the machine 310 may perform before the metal sheet exits the machine 310, and finishing the workpiece (i.e., cleaning, smoothing, etc.), the final product is a plunger body having an inner wall defining an axial chamber, an outer wall, and first and second ends. As will be discussed further below, the plunger body will include a hanger for attaching the plunger body to the molding system, and corrugated edges to strengthen adherence of the molded portions onto the metal plunger body. The machine 110 used in the exemplary method 100 of FIG. 5 is a mechanical stamping press, but may be hydraulic, mechanical servo, or other type of stamping press.

FIG. 7 depicts a schematic of the stamping machine 110 to more clearly illustrate how the stamping machine 110 processes the blank of sheet metal 120 into a plurality of plunger bodies. Initially, a leading edge 122 of the metal sheet 120 is inserted into the stamping machine 110 at the inlet 114 and is processed by a plurality of dies 124 while the metal sheet 120 moves along the travel path 118. A gripper 126 disposed in the housing 112 of the machine 110 conveys the metal sheet 120 along the travel path 118. In particular, a first gripper 126 proximally located relative to the inlet 114 contacts first and second parallel edges or margins 128, 130 (FIG. 6) of the metal sheet 120. The gripper 126 includes first and second wheels 132, 134 positioned to engage opposing surfaces of the metal sheet 120. In the illustrated example, a second set of grippers 140 are proximally located relative to the outlet 116 of the machine 110, and engage the metal sheet 120 to convey the metal sheet 120 through the machine 110. However, in other examples, the machine 110 may include one gripper mechanism at any location of the travel path 118 to convey the metal sheet 120 through the machine 110.

Specifically in FIG. 7, the first wheel 132 disposed above the metal sheet 120 engages a first side or surface 136 of the sheet 120, and the second wheel 134 disposed below the sheet 120 engages a second side or surface 138 of the sheet 120. The first wheel 132 rotates in a first direction B, and the second wheel 134 rotates in a second direction C, opposite the first direction B, thereby gripping the metal sheet 120 between the rotating wheels 132, 134 and causing the sheet 120 to move in a linear direction D. In the illustrated example of FIG. 7, each wheel 132, 134 is semi-circular, thereby allowing incremental movement of the blank of sheet metal 120 while the wheels 132, 134 continuously rotate. However, in another example, the wheels 132, 134 may have complete circular cross-sections such that each part of the wheel always engages the metal sheet 120. In this case, the wheels 132, 134 may be powered to rotate incrementally, rather than continuously. The set of rotating wheels 132, 134 engages one of the margins or parallel edges of the blank of sheet metal 120 to avoid any interference with the plurality of dies and/or the shaping of the metal sheet 120 as it moves along the travel path 118. However, as shown in FIG. 6, each of a first and second set of grippers 126A, 126B is adjacent to one of the parallel margins 128, 130 of the metal sheet 120. In yet another example, the gripper may be an entirely different mechanism that transports the metal sheet 120 through the machine 110.

FIG. 7 generally shows an exemplary layout of the plurality of dies 124 of the stamping machine 110. The plurality of dies 124 moves with respect to the blank of sheet metal 120 and is adjacent to the travel path 118 of the metal sheet 120. The machine 110 operates the plurality of dies 124 to impact the metal sheet 120 at various stages of the machine 110, gradually forming a cylindrical workpiece 125 and into a final cylindrical plunger body. At least one of the plurality of dies 124 is positioned above the travel path 118 and at least one of the plurality of dies 124 is positioned below the travel path 118. Each of the dies 124 is shaped and positioned relative to the travel path 118 to form a particular bend, shape, or cut in the workpiece 125 when the one or more dies 124 impacts and engages the metal sheet 120. The machine 110 activates the dies 124 to move toward the metal sheet 120 and contact the first and second surfaces 136, 138 of the metal sheet 120 when the metal sheet 120 is stationary relative to the travel path 118. At some stages, multiple dies 124 are above and below the travel path 118 to shape both surfaces 136, 138 of the workpiece 125. After the one or more dies 124 contacts and shapes the workpiece 125 at each stage, the one or more dies 124 of each stage returns to its previous position, spaced away from the metal sheet 120. During or shortly after the one or more dies 124 disengages from the metal sheet 120, the metal sheet 120 continues to move incrementally in the D direction (i.e., as the semicircular wheels 132, 134 of the gripper 126 again engage the metal sheet 120). This process repeats continuously such that when the metal sheet 120 pauses in the travel path 118, the dies 124 again move toward the metal sheet 120 to engage and shape each workpiece 125 before the sheet 120 continues along the travel path 118. At some stages, also referred herein as "free" stages, the workpiece 125 may not be shaped or otherwise engaged by any movable dies 124. The dies 124 of the stamping machine 110 may include combination, compound, progressive, or transfer dies.

Figure 8:
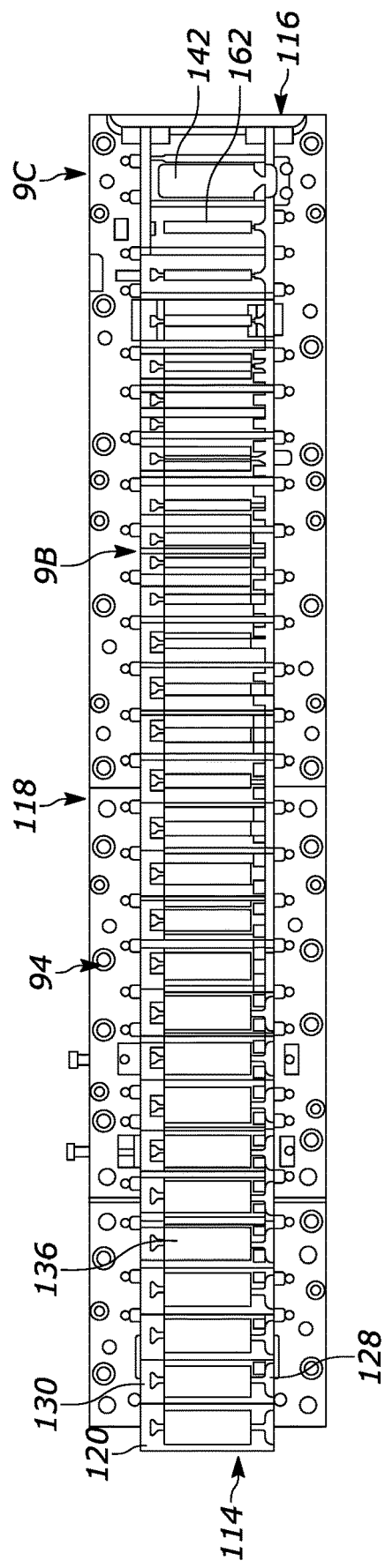
FIG. 8 is a top view of a portion of the stamping system of FIG. 6.

FIG. 8 depicts the metal sheet 120 disposed in the travel path 118 of the machine 110 with a plurality of workpieces 125 each at a different stage of formation. Adjacent the inlet 114, the blank of sheet metal 120 is flat and adjacent the outlet 116, the blank of sheet metal 120 has a rectangular space 142 from which a formed plunger body was shaped and separated from the metal sheet 120. In one exemplary stage 9A, a first die 144 and a second die 148 engage both the first and second surfaces 128, 130 of the metal sheet 120 to bend the workpiece 125 inwardly (relative to the first surface 136) to form a cylindrical body 225.

In the exemplary stage shown in FIG. 9A, the first die 144 has a concave surface 150 and engages the second (or bottom) surface 138 of the workpiece 125. Simultaneously, the second die 148 has a convex surface 152 and engages the first (or top) surface 136 of the workpiece 125. When both dies 144, 148 impact the metal sheet 120, the workpiece 125 bends into a curve according to the contours of the dies 144, 148. At another stage shown in FIG. 9B, a cylindrical body 225 of the workpiece 125 is almost completely formed, and at this stage in the shaping process only one die 154 engages the second surface 138, which is shaped into an outer wall 160 of the plunger body workpiece 125. Finally, FIG. 9C illustrates a finished shaped plunger body 162 in one of the final stages 9C of the stamping machine 110. The plunger body 162 includes a first end 164, a second end 166 opposite the first end 164, an inner wall defining an axial chamber 168, and the outer wall 160. A hanger 170 includes two apertures 172 and is connected to the first end 164 of the plunger body 162. The first end 164 includes a corrugated edge 174 that is bent outwardly relative to the axial chamber 168 and the second end 166 includes a corrugated edge 176 bent inwardly relative to the axial chamber 168.

Figure 10:
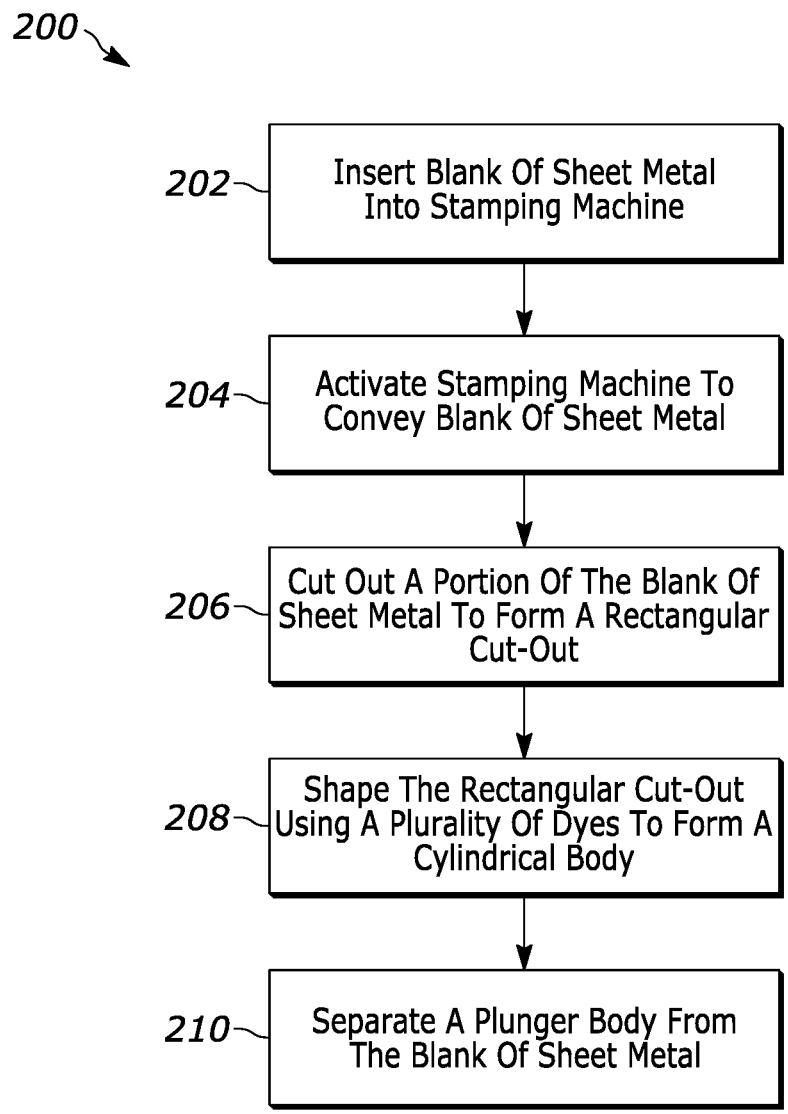
FIG. 10 is a schematic diagram of an exemplary method of manufacturing a straw of the plunger rod of FIG. 4A in accordance with the systems and methods disclosed herein.

FIG. 10 depicts a method 200 of forming the plunger body 162 in more detail and with reference to FIGS. 11A-12D. As previously described, the method 200 of forming the plunger body 162 begins, at step 202, by inserting a blank of sheet metal 120 into the inlet 114 of the stamping machine 110. In a second step 204, the machine 110 is activated or turned on, thereby operating the one or more grippers 126 of the machine 110 to convey the metal sheet 120 along the travel path 118. The movable dies 124 are disposed along the travel path 118 and correspond to a plurality of stages of processing a central portion of the metal sheet 120 (i.e., the workpiece 125) into a plunger body 162. In one of the first stages of the shaping process, a step 206 of cutting out a portion of the metal sheet 120 is performed by one or more of the plurality of dies 124. As will be described in more detail below, the step 204 of cutting (also referred herein as "punching") the metal sheet 120 includes cutting one or more portions out of the metal sheet 120 to form a rectangular cut-out. In subsequent stages of the shaping process, the dies 124 shape the rectangular cut-out by performing step 208 of the method 200. The dies 124 gradually shape a plurality of rectangular cut-outs (or workpieces 125) of the metal sheet 120 into a plurality of cylindrical plunger bodies 162. In a final step 210, the workpiece 125 is separated from the blank of sheet metal 120.

Figure 11C:
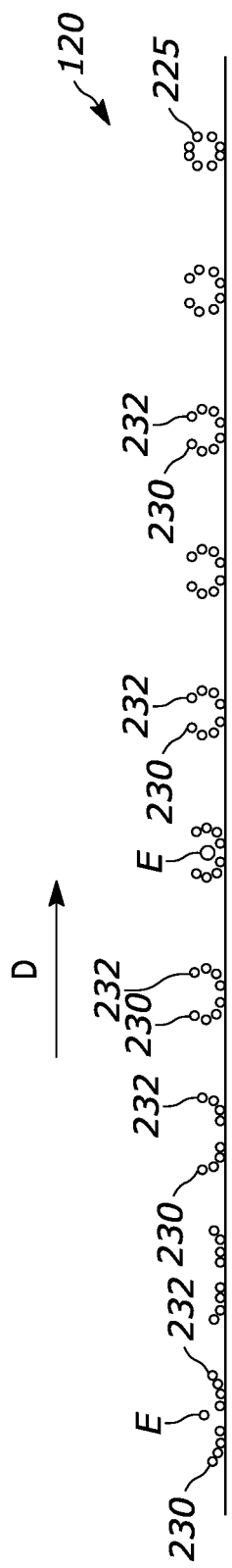
FIG. 11C is a magnified side view of the processed metal sheet of FIG. 11A, showing stages 11-20 of the stamping process.
Figure 11D:
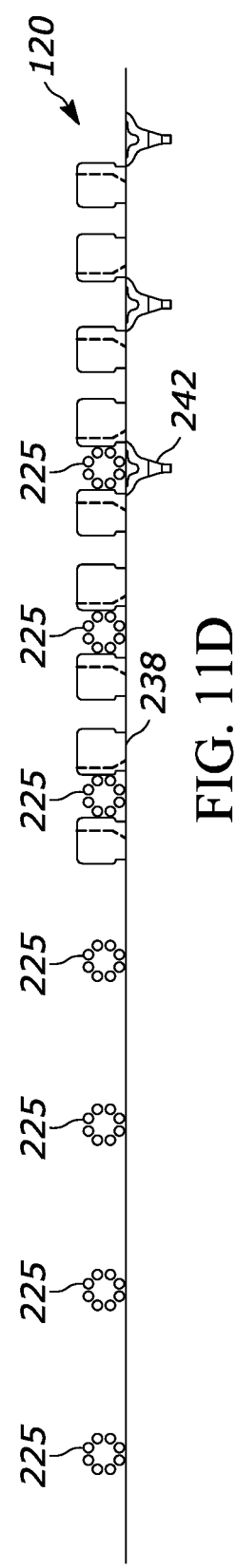
FIG. 11D is a magnified side view of the processed metal sheet of FIG. 11A, showing stages 21-29 of the stamping process.
Figure 12A:
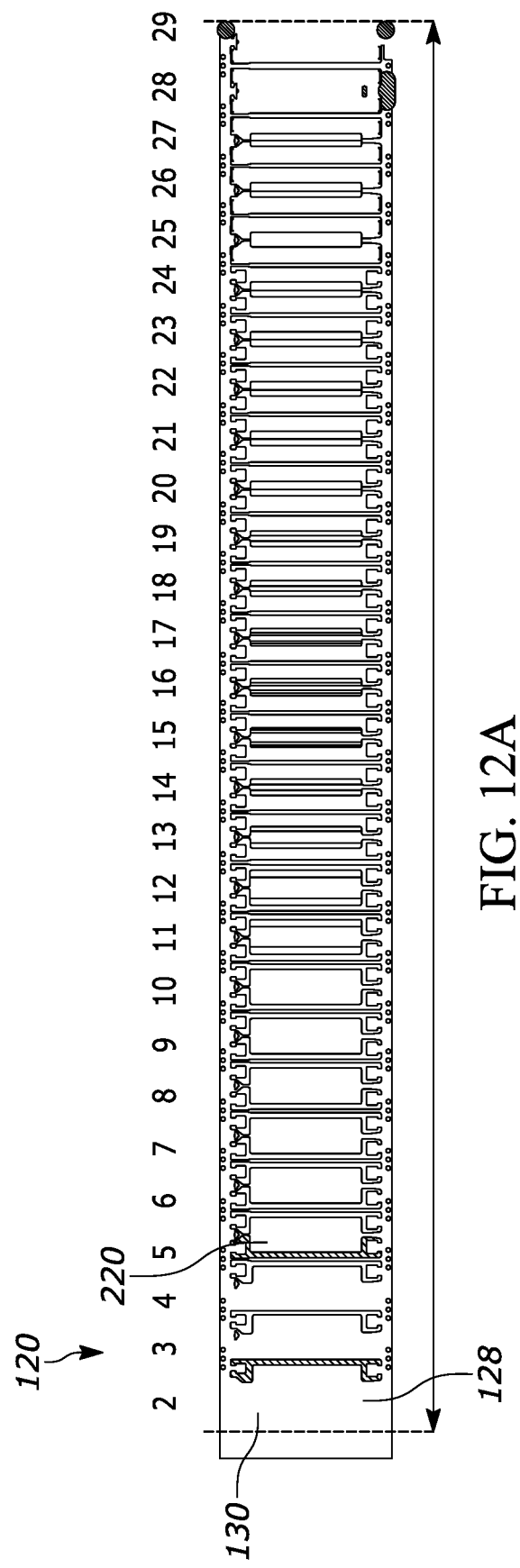
FIG. 12A is a top view of the blank metal sheet being processed in the stamping system of the present disclosure, and corresponding to the side view stages illustrated in FIG. 11A.

Turning now to FIGS. 11A and 12A, the steps 206, 208 of cutting and shaping the blank of sheet metal 120 in stages 1 through 29 of the stamping process 200 (i.e., the method of forming the plunger body) are illustrated. Each of a plurality of exemplary stages of the method 200 is labeled next to the corresponding workpiece 125 or portion of the sheet metal 120 processed at that stage (i.e. illustrating the resulting punch or bend of a particular die). One continuously processed blank of sheet metal 120 includes multiple different workpieces 125, and each workpiece 125 is processed in the stamping machine 110 at each stage (e.g., punching, blanking, embossing, coining, bending, flanging, etc.). In this way, the stamping machine 110 may process 29 different workpieces 125 at any given time. In other words, the number of stages of the method 200 generally corresponds to the number of workpieces 125 being processed. The following 29 stages of the stamping method 200 will be described in three sections of the machine 110: stages 1 through 10 are described and illustrated with reference to FIGS. 11B and 12B; stages 11 through 20 are described and illustrated with reference to FIGS. 11C and 12C, and stages 21 through 29 are described and illustrated with reference to FIGS. 11D and 12D. The exemplary stages 1 through 29 may be modified to reach the formed plunger body 162 by reducing or increasing the number of stages in the machine 110. Depending on the desired size and shape of the resulting plungers, more or fewer than twenty-nine workpieces 125 may be processed simultaneously by the machine 110.

Figure 12B:
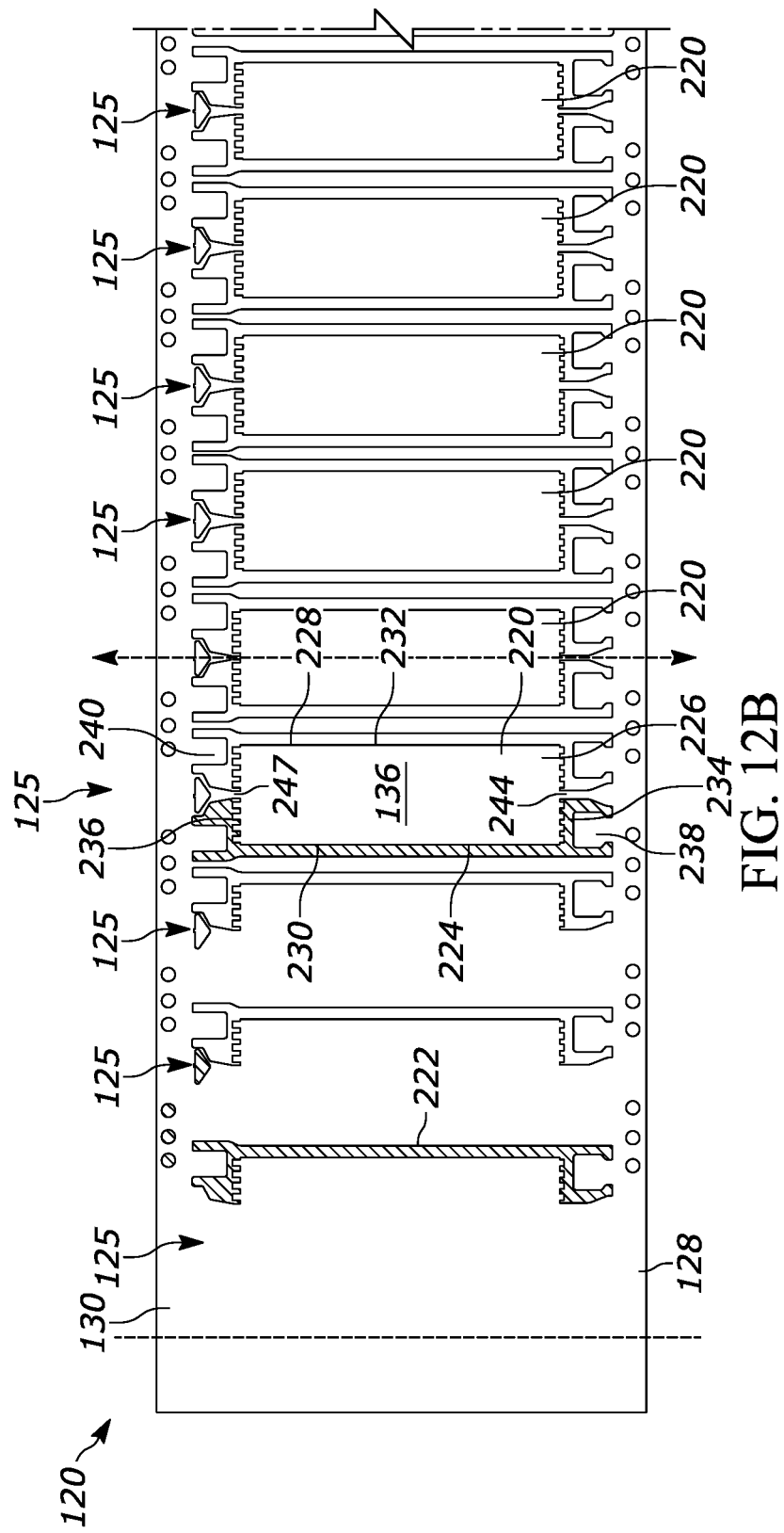
FIG. 12B is a magnified top view of the processed metal sheet of FIG. 12A, and corresponding to the side view stages illustrated in FIG. 11B.

FIGS. 11B and 12B illustrate the first stages of shaping the blank of sheet metal 120. At stage 1, the metal sheet 120 is initially flat when an operator inserts the metal sheet 120 into the stamping machine 110, and activates the machine 110 to convey the metal sheet 120 along the travel path 118. The machine 110 is programmed to operate step 206 of the method 200 of FIG. 10 in stages 2 through 5. Specifically, at stages 2 and 5, one or more dies 124 punches out first and second portions of sheet metal 120 to define a rectangular cut-out 220. In stage 2, a punching die 124 engages the workpiece 125 by punching out a right segment 222 of the flat metal sheet 120, and at stage 5, a different punching die 124 engages the workpiece 125 by punching out a left segment 224. With the first and second portions 222, 224 removed from the workpiece 125, the rectangular cut-out 220 is defined and includes a first end 226, a second end 228 opposite the first end 226, a first side 230, and a second side 232 connecting the first and second ends 226, 228 (as shown at stage 5). The same or different punching dies 124 form first and second corrugated edges 234, 236 of the rectangular cut-out 220 during these stages.

One or more dies 124 of the stamping machine 110 further shapes the corrugated edges 234, 236 of the rectangular cut-out 220 at stages 6 through 10. At stage 7, for example, the method 200 includes bending the second end 228 of the rectangular cut-out 220 toward the first surface 136 of the rectangular cut-out 220 such that the second corrugated edge 236 is substantially perpendicular to the first surface 136 of the workpiece 125. Similarly, at stage 9, the method 200 includes bending the first end 226 of the rectangular cut-out 220 toward the second surface 138 of the workpiece 125 such that the first corrugated edge 234 is substantially perpendicular to the second surface 138 of the workpiece 125. The steps of bending the corrugated edges 234, 236 are illustrated in FIG. 11B at stages 7 and 9. Consequently, as the cylindrical body 225 of the workpiece 125 takes shape, the corrugated ends 234, 236 of the rectangular cut-out 220 define the corrugated edges 174, 176 of the final plunger body 162 (FIG. 9C). Stages 4, 6, 8, and 10 are considered "free" stages to allow for modifications to the method 200 and machine 110.

At stage 3, a punching die 124 punches the workpiece 125 to define a strawfoot 242 connecting the second end 228 to the second margin 130 of the blank of sheet metal 120 (stage 5). Opposite the strawfoot 242 is a connector 244 coupling the first end 226 of the rectangular cut-out 220 to the first margin 128. The strawfoot 242 and the connector 244 keep the workpiece 125 securely positioned relative to the travel path 118 while moving through the stamping machine 110. Later in the method 200, the stamping dies 124 cut and bend the strawfoot 242 away from the workpiece 125 and punch a portion of the first margin 128 to define the hanger 170 of the plunger body 162. The right and left cut-outs 222, 224 also define a first set of tabs 238 and a second set of tabs 240 in each workpiece 125.

Figure 12C:
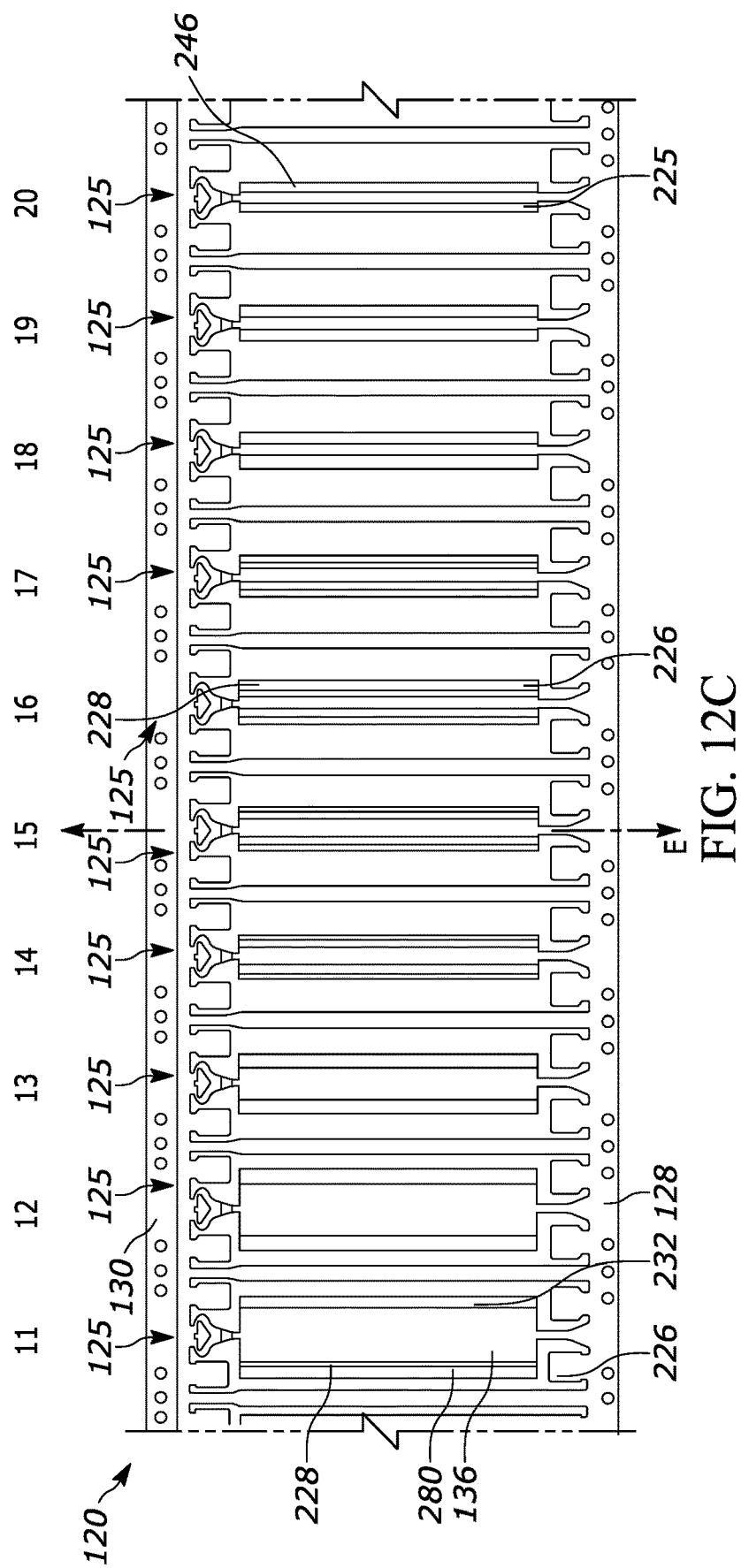
FIG. 12C is a magnified top view of the processed metal sheet of FIG. 12A, and corresponding to the side view stages illustrated in FIG. 11C.

FIGS. 11C and 12C illustrate the workpiece 125 being formed into a cylindrical shape. Step 208 of the method 200 is mostly performed in stages 11 through 20. Shaping the rectangular cut-out 220 includes gradually bending the first and second sides 230, 232 of the workpiece 125 inward (i.e., toward the first surface 136) such that as the blank of sheet metal 120 moves in the direction D toward the outlet 116 of the stamping machine 110, the first surface 136 gradually defines what will be the inner wall of the plunger body 162. In other words, the dies 124 engage the workpiece 125 to bend the first and second sides 230, 232 of the rectangular cut-out 220 toward each other. For example, in FIG. 11C the first and second sides 230, 232 of each cut-out 220 are bent inwardly relative to an axis E of the workpiece 125. At stages 11, 13, 14, 16, 17, 18, and 20, the machine 110 shapes the workpiece 125 further into a cylindrical body 225 by curving the first and second sides 230, 232 closer together. For example, the first and second sides 230, 232 are spaced approximately 16.5 mm apart at stage 11, approximately 11.4 mm at stage 13, approximately 6.8 mm at stage 14, approximately 5.4 mm at stage 16, and approximately 2.1 mm at stage 18.

In the illustrated example, the machine 110 utilizes a progressive tool method with built-in bend and punch dies for high speed stamping to process 2 workpieces per second. At each of these punching, bending, and shaping stages, the dies 124 may shape the metal sheet 120 in one or more of a variety of methods. For example, in some cases, the dies 124 stamp the sheet metal 120 to deform the metal sheet 120 plastically to take the shape of the die geometry. At some stages, the dies 124 allow the workpiece 125 to spring back after impact, while in other stages, the metal sheet 120 is formed so that the workpiece 125 is shaped without permitting the metal sheet 120 to spring back (i.e., shaping beyond the yield stress of the metal sheet 120). Other stamping methods includes, transfer die stamping, four-slide stamping, and fine blanking.

Finally, at stage 20 the cylindrical body 225 of the workpiece 125 is finalized to further close the gap between the two sides 230, 232 of the cut-out 220. In the illustrated example, the first and second sides 230, 232 of the workpiece 125 do not meet or overlap. Rather, a seam or longitudinal gap 246 extends from the first and second ends 226, 228 of each workpiece 125. This gap between the first and second sides 230, 232 has a width of less than approximately 0.05 mm.

Figure 12D:
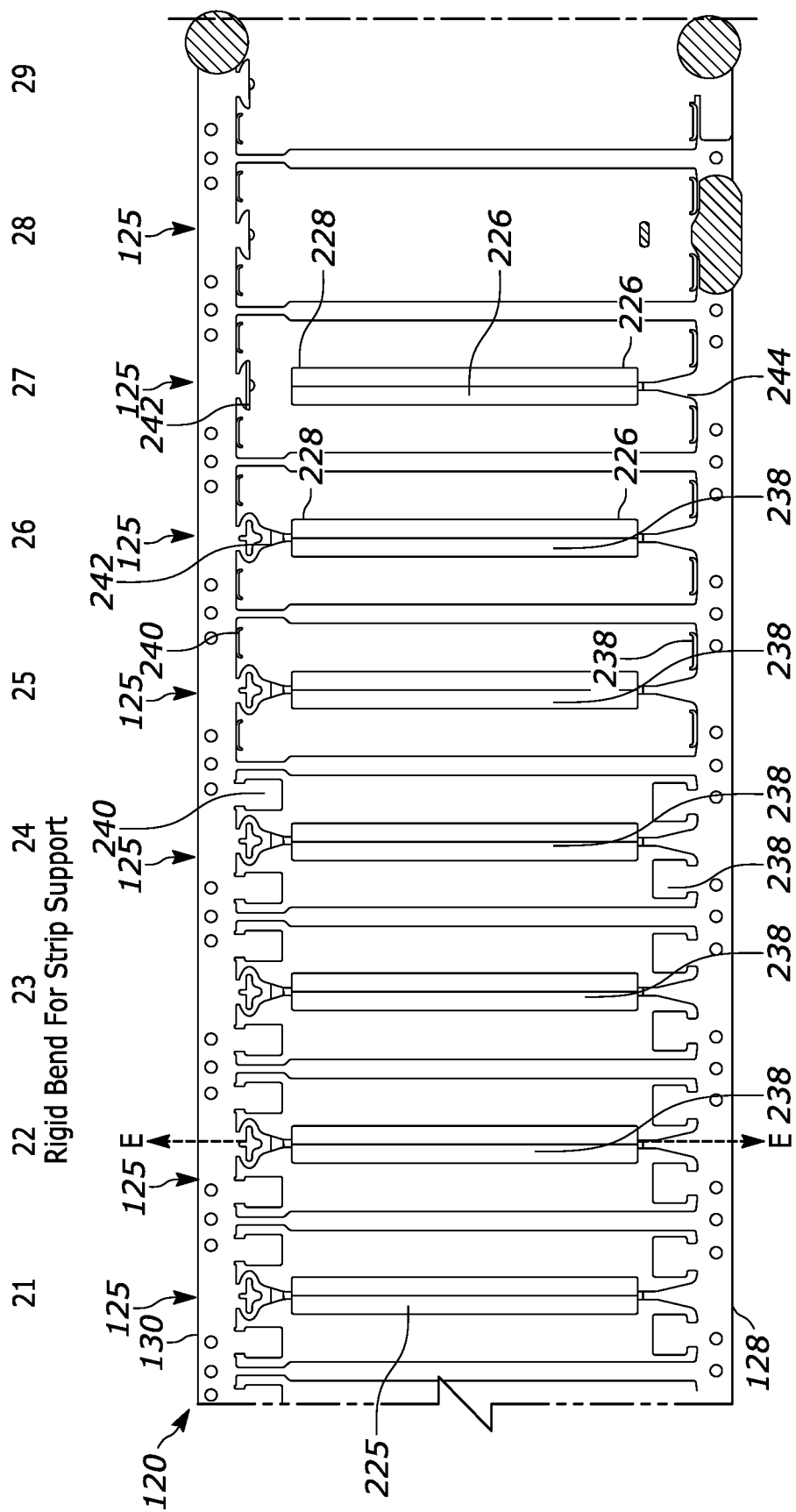
FIG. 12D is a magnified top view of the processed metal sheet of FIG. 12A, and corresponding to the side view stages illustrated in FIG. 11D.

In FIGS. 11D and 12D, the final stages of the stamping method 200 are illustrated. In stages 22 and 24, the system 110 calibrates the cylindrical body 225 of the workpiece 125. During calibration, a die 124 having the same diameter as the die 124 used during the final bending stage (i.e., stage 20) engages the second surface 138 of the workpiece 125, now defining an outer wall 160, of the plunger body 162. At stage 23, first and second set of tabs 238, 240 connected to the first and second margins 128, 130, respectively, are minimally bent for rigidity. At stage 25, the first and second set of tabs 238, 240 are bent so that each tab 238, 240 is perpendicular relative to the first and second margins 128, 130 of the blank of sheet metal 120. These tabs 238, 240 may serve to protect a plurality of workpieces 125 that remain attached to the metal sheet 120 when the metal sheet 120 is rolled up for storage. While the illustrated workpiece 125 is blanked (i.e. separated) from the metal sheet 120 at stages 27 and 28, in some examples, the stamping machine 110 may be programmed so that the workpiece 125 remains connected to the metal sheet 120. The workpieces 125 attached to the first margin 128 of the metal sheet 120 may be stored by rolling or folding the metal sheet 120. The first and second set of tabs 238, 240 extend from each workpiece to maintain space between the plurality workpieces 125 to protect the workpieces 120 in storage.

Finally, step 210 of separating the workpiece-now-plunger body 162 from the blank of sheet metal 120 is performed at stages 27 and 28. First at stage 27, one or more dies 124 of the machine 110 cuts and bends the strawfoot 242 away from the second end 228 of the workpiece 125, leaving the workpiece 125 attached to the metal sheet 120 at the first margin 128. Then at stage 28, the workpiece 125 is completely removed from the metal sheet 120 by punching the first margin 128, thereby forming the hanger 170 of the plunger body 162. Stages 21 and 26 are free stages.

Figure 13:
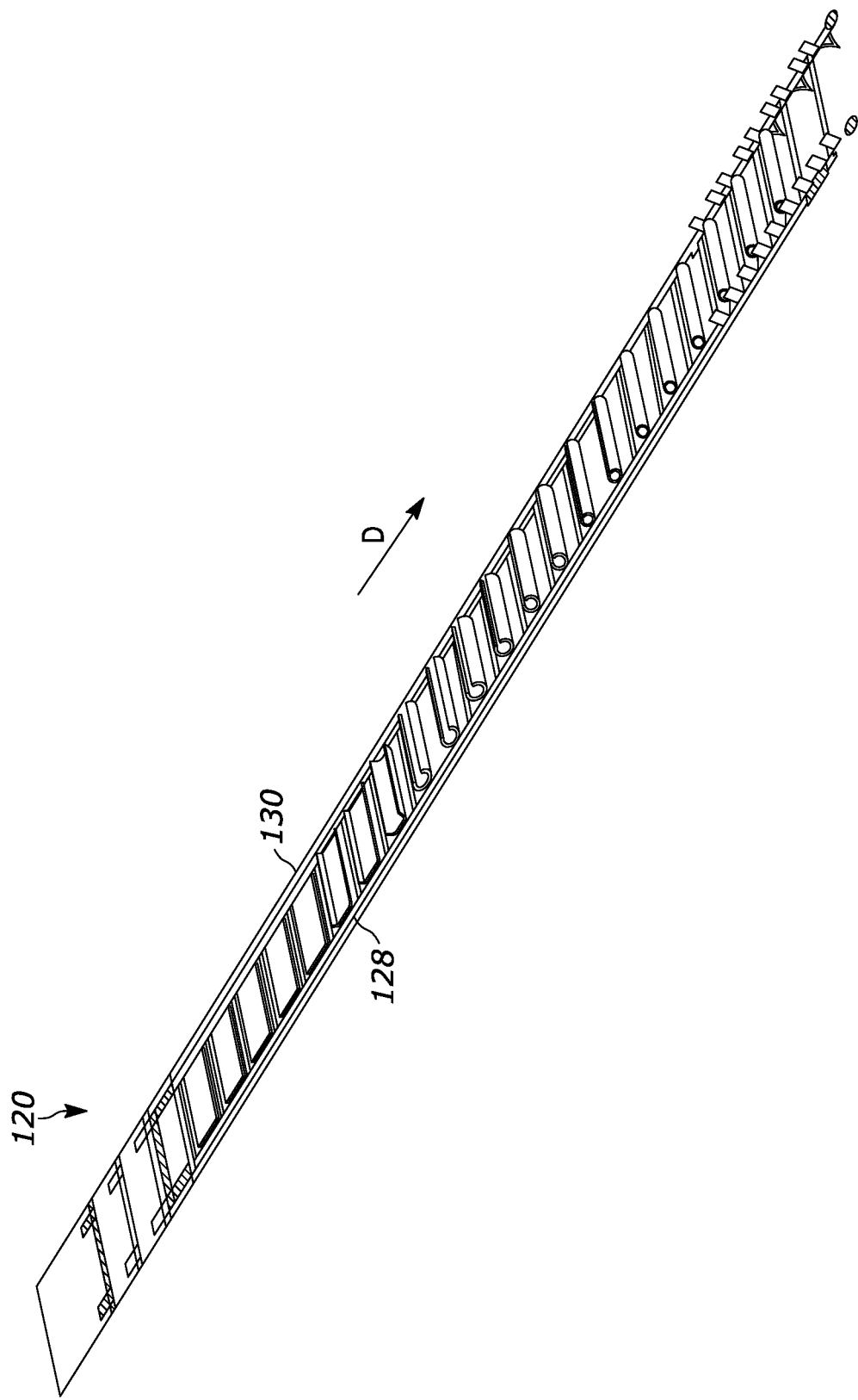
FIG. 13 is a perspective view of the processed metal sheet of FIGS. 11A and 12A, showing a plunger rod straw in various stages of the stamping process.

FIG. 13 illustrates the blank of sheet metal 120 processed by the stamping machine 110 in accordance with the present disclosure. As shown in this figure, the sheet metal 120 includes a plurality of workpieces being processed at different stages of the method 200 to form the plunger body 162 of FIG. 9C. In this way, the stamping machine 110 permits continuous processing of metal sheet 120 into workpieces 125, eventually forming a plurality of plunger bodies 162. Except for the need to load and/or reload the stamping machine 110 with metal sheet 120, the method of forming multiple plunger bodies 200 using the stamping machine 110 is a continuous or semi-continuous process.

Figure 14:
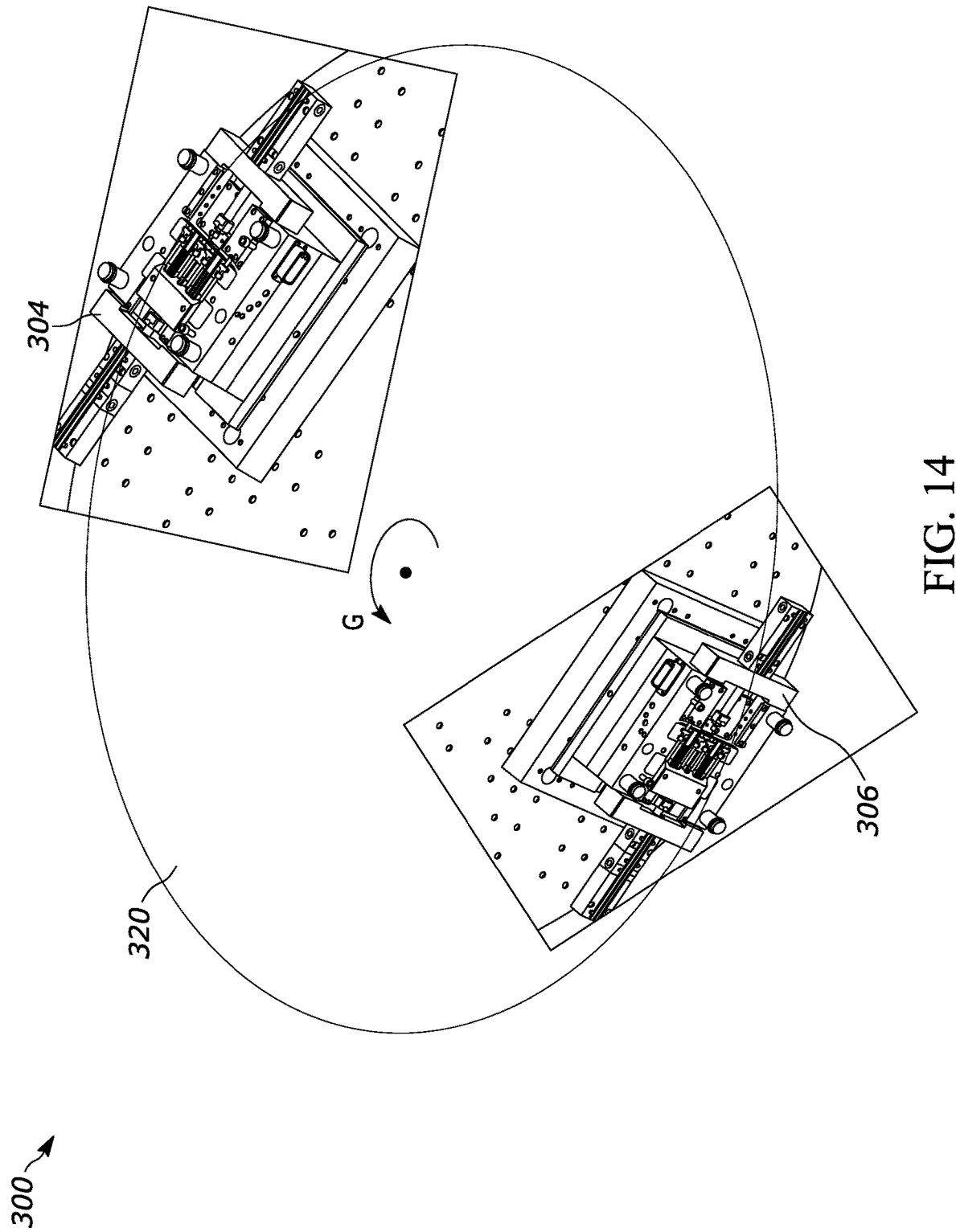
FIG. 14 is a top perspective view of a plunger rod roundtable molding system constructed in accordance with the teachings of the present disclosure.

Turning now to FIG. 14, an exemplary molding system 300 for performing the second phase of the manufacturing process 100 is constructed in accordance with the teachings of the present disclosure. In operation, the molding system 300 forms the head 45 and foot 47 portions of the plunger 26 (FIG. 4A) around a plunger body 162, such as the plunger body 162 formed by the stamping machine 110 of FIGS. 6-9. Generally, the molding system 300 includes a first station, Station I, for loading plunger bodies 162 and unloading overmolded plunger bodies, and a second station, Station II, for injection-molding the head and foot portions 45, 47 onto the plunger body 162. At Station I, an operator loads a first molding tool 304 with one or more plunger bodies 162. At Station II, the first molding tool 304 couples to a second molding tool (disposed directly above an identical first molding tool 306, but hidden in FIG. 14), and the system 300 injects molten plastic into a mold (i.e. the clamped first and second molding tools). When the first and second molding tools couple at Station II, the first molding tool and the second molding tool define a head mold, or negative head space, and a foot mold, or negative foot space, that will define the head and foot 45, 47 portions of the plunger 26. The molten plastic shoots through a series of channels in the mold to fill the head and foot molds. While the system 300 includes two identical first molding tools 304, 306, in other examples, the system 300 may include one first molding tool 304 or more than two first and/or second molding tools.

Figure 15:
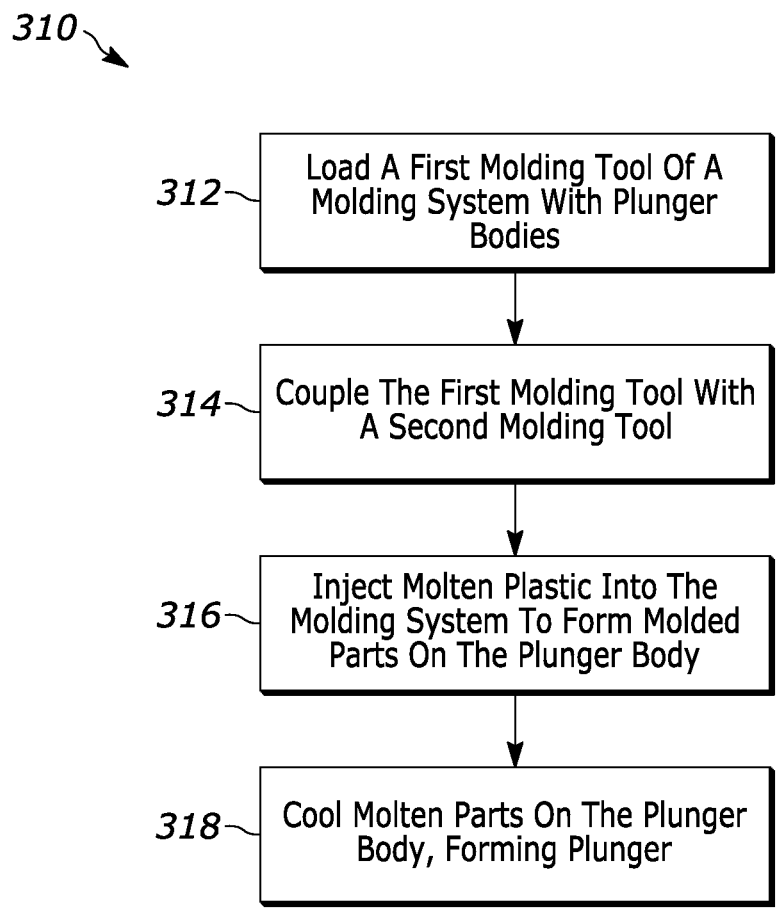
FIG. 15 is a schematic diagram of an exemplary method of manufacturing overmolded pieces onto the straw of the plunger rod of FIG. 4A in accordance with the systems and methods disclosed herein.

FIG. 15 depicts an exemplary method 310 of overmolding one or more plunger bodies 162 in accordance with the teachings of the present disclosure. A first step 312 includes loading the first molding tool 304 of the molding system 300 with one or more plunger bodies 162. The molding system 300 of FIG. 14 may automatically perform one or more of the following steps of the method 310 after an operator or robot performs step 312. A step 314 of the method 310 includes coupling the first molding tool 304, 306 with the second molding tool. When the first and second molding tools are coupled, the system 300 injects molten plastic into the first and second molding tools at a step 316 to form the molded components (i.e., the head and the foot) onto the plunger body 162. Finally, in step 318, the molded components are cooled onto the plunger body 162, and the molded plunger bodies are ejected or otherwise removed from the first molding tool 304, 306 at Station I. As a result of completing each step of the method, a plurality of plungers for the drug delivery device 10 of FIGS. 1-3B are provided.

Returning to FIG. 14, the molding system 300 includes a rotatable table 308 with the first molding tool 304 at Station I, and the other identical first molding tool 306 at Station II. While not illustrated in FIG. 14, the second molding tool 404 (FIG. 21) is disposed at Station II and is arranged to couple to either of the first molding tools 304, 306 to overmold the plunger bodies 162. As such, the second molding tool remains at Station II while the first molding tools 304, 306 spin in and out of Stations I and II. The first molding tool 304 rotates relative to the second molding tool 404, and the second molding tool 404 moves axially relative to the first molding tool 304 to couple to the first molding tool 304 at Station II.

In operation, the table 308 rotates in a direction G to move the first molding tool 304, loaded with one or more plunger bodies 162, from Station I to Station II. Simultaneously, the table 308 also moves the other first molding tool 306 from Station II to Station I. At Station II, the plunger bodies 162 are overmolded by injection molding. After the plunger bodies 162 of the first molding tool 304 are molded and cooled at Station II, the table 308 again rotates the first molding tool 304 back to Station I, where the overmolded plunger bodies are removed from the first molding tool 304 and replaced with additional plunger bodies 162. Of course, each time the table 308 rotates to position the first molding tool 304, the other first molding tool 306 rotates to the opposite station. For example, as an operator loads the first molding tool 304 at Station I, the plunger bodies 162 disposed in the identical molding tool 306 are overmolded at Station II. The table 308 rotates 180 degrees to move each of the first molding tools 304, 306 between Station I and Station II. However, other configurations of the molding system 300 are possible 300 and may include additional first molding tools disposed around the circumference of the table 308. In yet another example, the molding system 300 may include a linear assembly line or only one station where the steps of loading, injection molding, and unloading are performed. While the exemplary system 300 is designed to overmold a plurality of plunger bodies, another exemplary system may only overmold one plunger body at a time.

Figure 16:
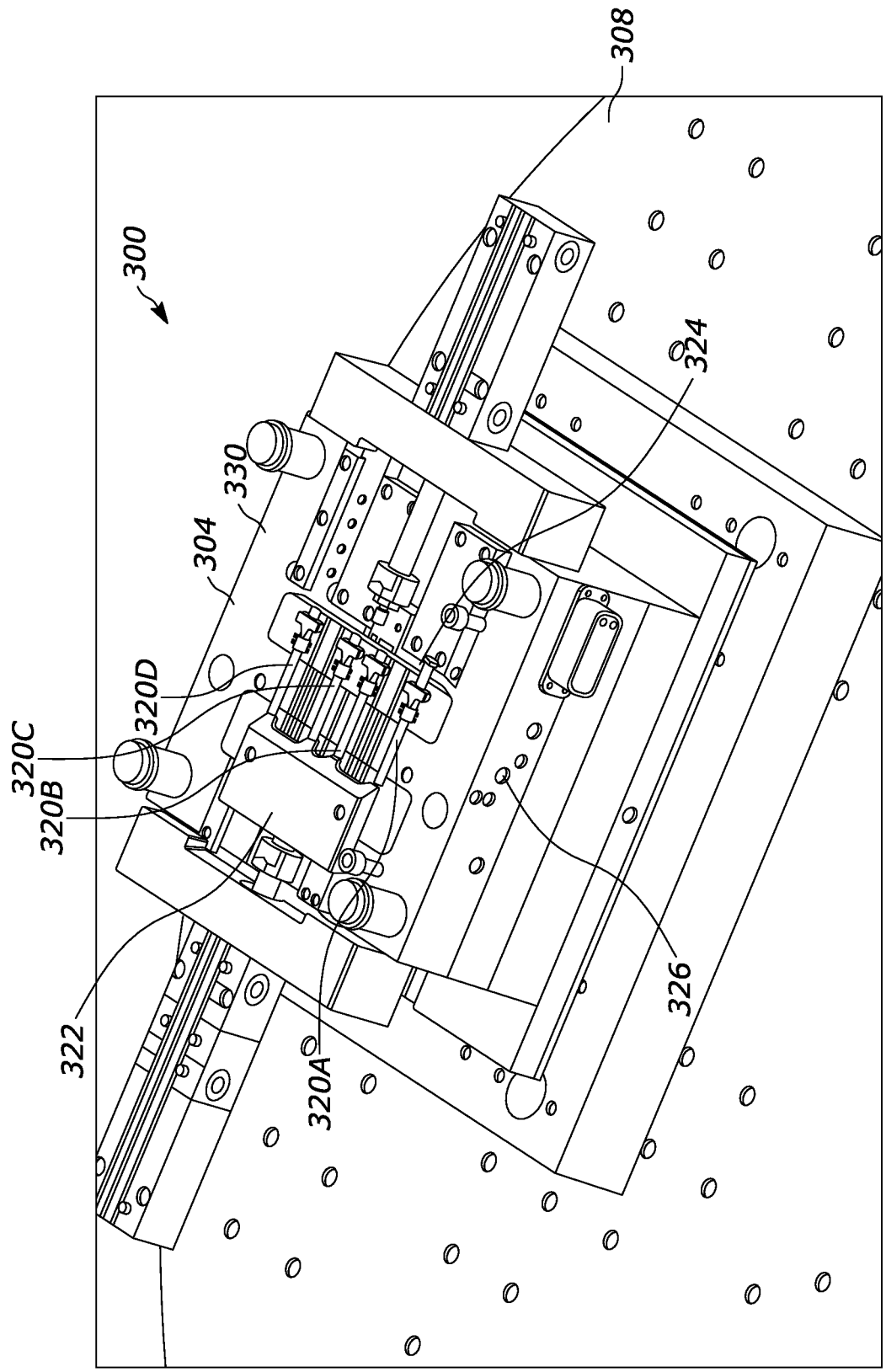
FIG. 16 is a top perspective view of a first molding tool located at a first station of the plunger rod roundtable molding system of FIG. 14.
Figure 22:
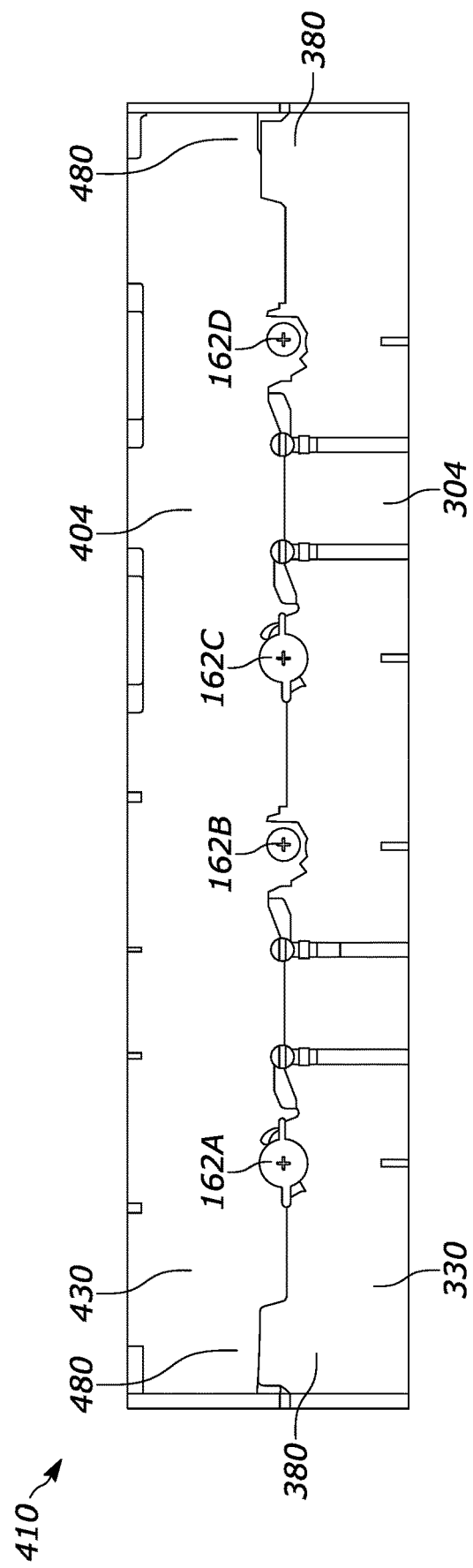
FIG. 22 is a cross-sectional view of a mold, showing the mating surface of the second molding tool coupled to a mating surface of the first molding tool when the first molding tool is at a second station.

The first molding tool 304 is generally shown in FIG. 16, and includes a plurality of cavities 320A-D, an actuated plate 322, and actuated cores 324 all coupled to a top platform 330. The top platform 330 of the first molding tool 304 also includes a plurality of cooling holes 326 arranged to receive heating fluid to warm up the molding tools and cooling fluid to cure the molded portions of the overmolded plunger bodies. As will be discussed in further detail below, the top platform 330 is configured to matingly couple with a corresponding platform 430 of the second molding tool 404 (FIG. 22). Various mating surfaces of the top platform 330 and the corresponding platform 430 of the second molding tool 404 are precisely shaped to achieve a tight clamp when the molding tools 304, 404 couple.

Figure 17:
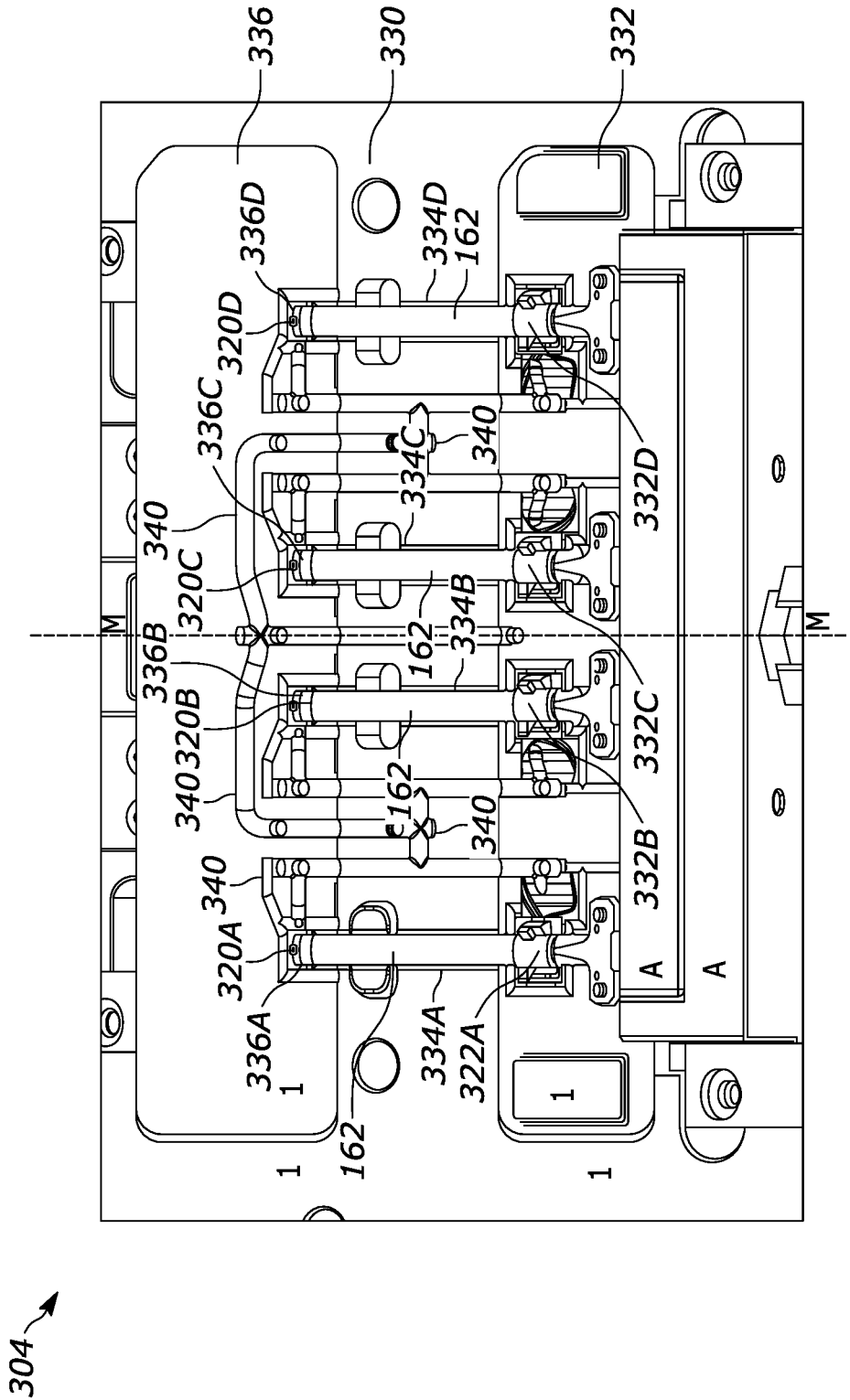
FIG. 17 is a top view of the first molding tool, with a plurality of plunger rod straws loaded onto the first molding tool.

In FIG. 17, the first molding tool 304 of the molding system 300 is at Station I with four plunger bodies 162 loaded into four separate cavities 320A, 320B, 320C, 320D. The second molding tool 404 has the same number of cavities as the first molding tool 304, and each cavity of the second molding tool is shaped to cover the plunger bodies 162 in the first molding tool 304. Each of the cavities 320A-D is defined by a first molding portion 332A-D of a first molding portion plate 332, a middle portion 334A-D of the platform 330, and a second molding portion 336-D of a second molding portion plate 336. Specifically, the first molding portion plate 332 of FIG. 17 defines four separate halves of a head mold 332A-D and the second molding portion plate 336 defines four separate halves of a foot mold 336A-D. The cavities 320A-D in the first molding tool 304 are connected by a network of grooves 340 formed in the top platform 330 and first and second molding portion plates 332, 336 of the first molding tool 304. Similarly, the cavities of the second molding tool 404 are also connected with corresponding grooves such that the plurality of grooves in both the first and second molding tools 304, 404 are arranged to form a plurality of channels in which molten plastic is injected. The mold forms the plurality of channels when the first molding tool 304 aligns with and couples to the second molding tool 404 at Station II. As described in further detail below, the plurality of channels extends between the first molding portion 332A-D and the second molding portion 336A-D of each cavity 320A-D of the first molding tool 304 and between the first molding portion and the second molding portion of each cavity of the second molding tool 404.

The first and second molding portion plates 332, 336 are removably coupled to the platform 330 of the first molding tool 304. First and second molding portion plates 332, 336 are replaceable to modify the molding system 300, and thereby the manufacturing method 100, to achieve different resulting plungers. For example, by simply switching out the molding portion plates 332, 336, the system 300 may be used to overmold plunger bodies of different dimensions and/or form different molded components onto plunger bodies. The molding portion plates 332, 336 are sized to fit within cavities formed in the top platform 330 of the first molding tool. Each plate 332, 336 is arranged to seamlessly fit into the first molding tool 304 and connect with the existing grooves formed in the platform 330 without requiring further adjustments of the system 300 or molding tool 304. Similarly, the second molding tool 404 (FIG. 21) includes replaceable first and second molding portions that correspond to the first and second molding portions 332, 336 of the first molding tool 304. As such, when the first and second molding portions 332, 336 are replaced in the first molding tool 304, the molding portions of the second molding tool are also replaced to match the first molding tool 304. However, in other examples, the cavities 320A-D may be formed entirely or partially in the platform 330 and/or removable plates.

Figure 18A:
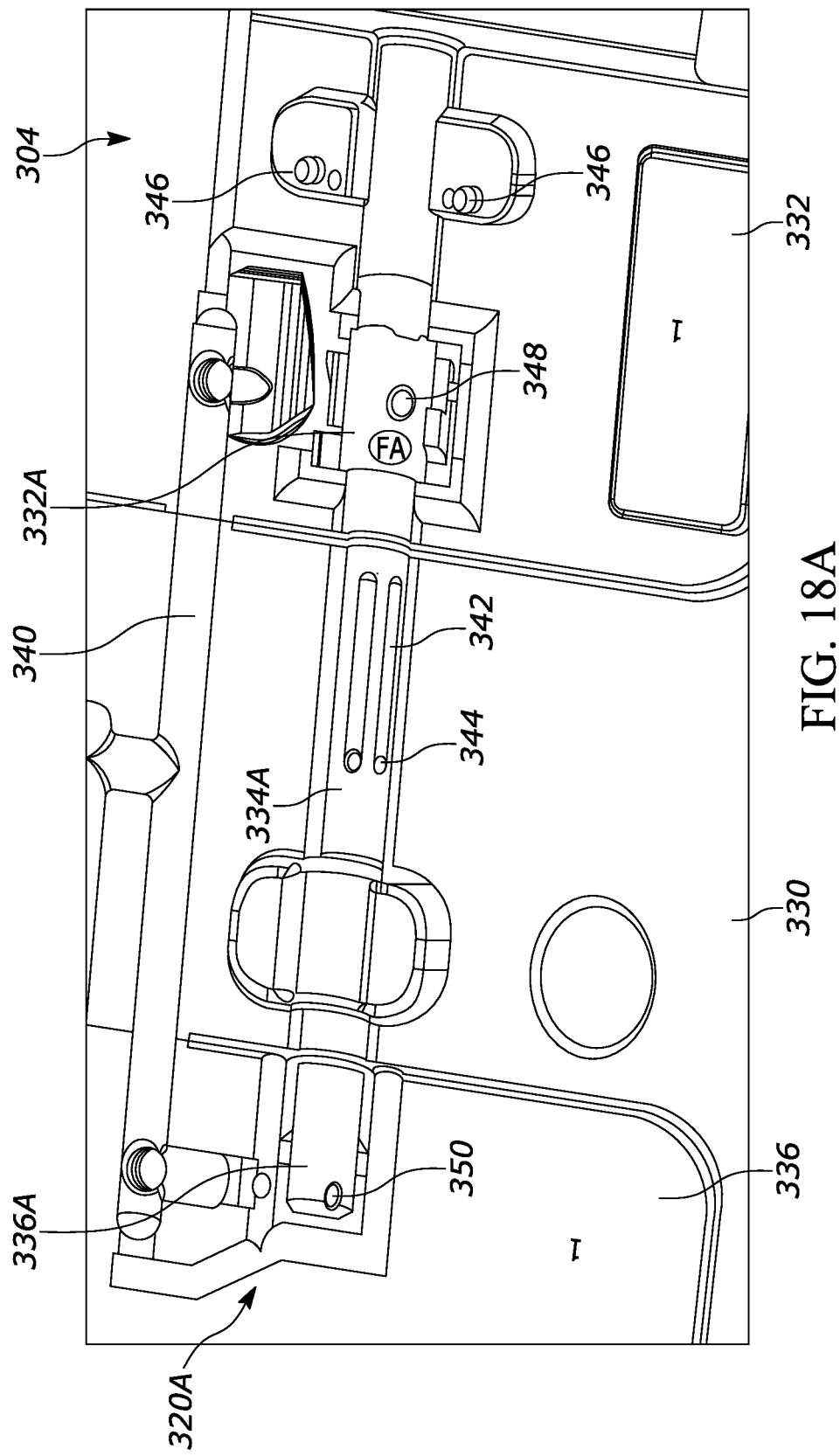
FIG. 18A is a top view of a first cavity of the first molding tool before the first molding tool is loaded.

In FIG. 18A, the first cavity 320A of the first molding tool 304 is more clearly shown. However, it will be appreciated that the first cavity 320A is substantially similar to the other cavities 302B-D, such that any details of the first cavity 320A discussed below apply equally to the other cavities 320B-D. The step 312 of loading the first molding tool 304 includes placing a plunger body 162 into the first cavity 320A of the first molding tool 304. In particular, the first end 164 of the plunger body 162 is placed into the first molding portion 332A and the second end 166 of the plunger body 162 is placed into the second molding portion 336A. The cylindrical plunger body 162 rests in the middle portion 334A of the cavity 320A and over one or more vacuum slots 342 formed in the platform 330. The molding system 300 includes a vacuum mechanism coupled to the vacuum slots 342 of each first molding tool 304, 306 to ensure that the plunger body 162 adheres to the first molding tool 304, 306 when the table 308 rotates. A sensor 344 is disposed in the one or more vacuum slots 342 and is communicatively coupled to a processor of the molding system 300 to monitor and report on the condition of the plunger bodies 162 on the first molding tool 304. The sensor 344 communicates with the processor when the plunger body 162 is not disposed completely over the vacuum slots 342 or when the sensor 344 detects a dent or other imperfection in the plunger body 162. If the sensor detects an imperfection or improper placement of the plunger body 162 onto the cavity 320A, the sensor 344 transmits that data to the processor, signally that a condition has been met. The processor is programmed to trigger an alarm of the system 300 if these conditions are met, which alerts an operator to reload the first molding tool 304. The alarm may also be associated with a lock-down feature of the molding system 300 such that if the alarm is triggered, the table 308 cannot rotate.

Also shown in FIG. 18A, the platform 330 includes mounting pins 346 and ejector pins 348, 350 for respectively securing and ejecting the plunger body 162 from the first molding tool 304. The mounting pins 346 are spaced from the first molding portion 332A and are arranged to receive the hanger 170 of the plunger body 162. To securely couple the plunger body 162 to the cavity 320A, each of the mounting pins 346 extends through one of the apertures 172 formed in the hanger 170. A first ejector pin 348 is in the negative head space 332A of the cavity 320A, and a second ejector pin 350 is in the negative foot space 336A of the cavity 320A. To remove an overmolded plunger body from the cavity 320A, the ejector pins 348, 350 actuate to extend from the platform 330 and into the overmolded plunger body to push the overmolded plunger body out of the cavity 320A. As shown in FIG. 18A, the ejector pins 348, 350 retract into cavity 320A when not in use, and remain in the retracted position until the overmolded plunger bodies are formed, cooled, and ready for removal. At which point, the system 300 may automatically detect that these conditions are met and activate the ejector pins 348, 350.

Figure 18B:
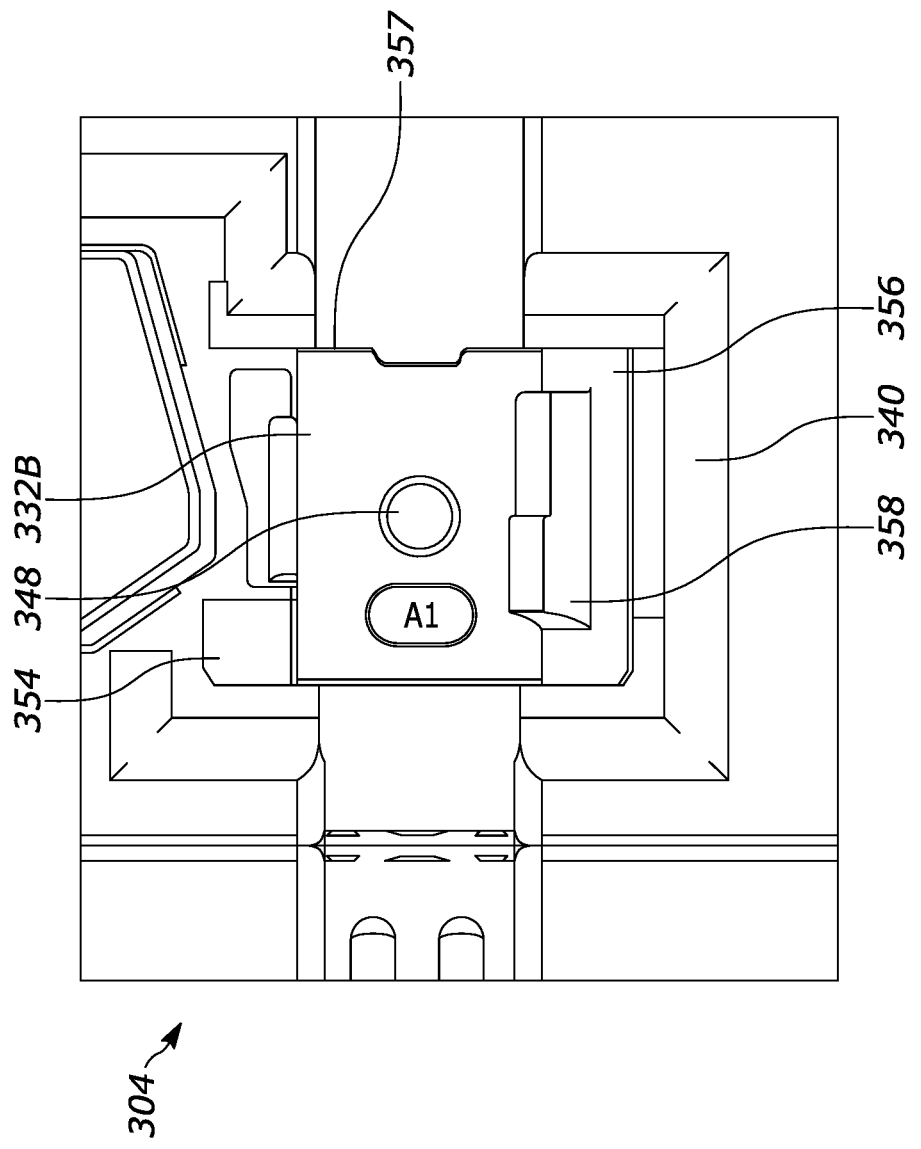
FIG. 18B is a magnified view of a first molding portion of the first molding tool.

FIG. 18B illustrates a magnified view of the first molding portion 332B of the second cavity 320B. The first molding portion 332B is half of the negative head space for the head mold. As previously mentioned, the second molding tool 404 provides corresponding cavities with negative head spaces (and negative foot spaces) that complete the mold 410 of the head portion 45 (and foot portion 47) of a plunger 26. FIG. 18B depicts how the first molding portions of the first and second molding tools 304, 404 provide a head mold 332B having a negative collar space 352 that will define a collar 45A, first and second flange negative spaces 354, 356 that will define the projections 48 or flanges that extend from the collar 45A, and a top end 357 that will define a portion of the head 45 that extends away from the corrugated edge 174 of the first end 164 of the plunger body 162 (FIG. 19C). At least one of the first and second flange negative spaces 354, 356 includes a distally facing sloped surface 358 to form the camming surface 49 on one or more of the projections 48. The mold of the negative foot space is described further below with respect to FIG. 19bC.

Figure 19A:
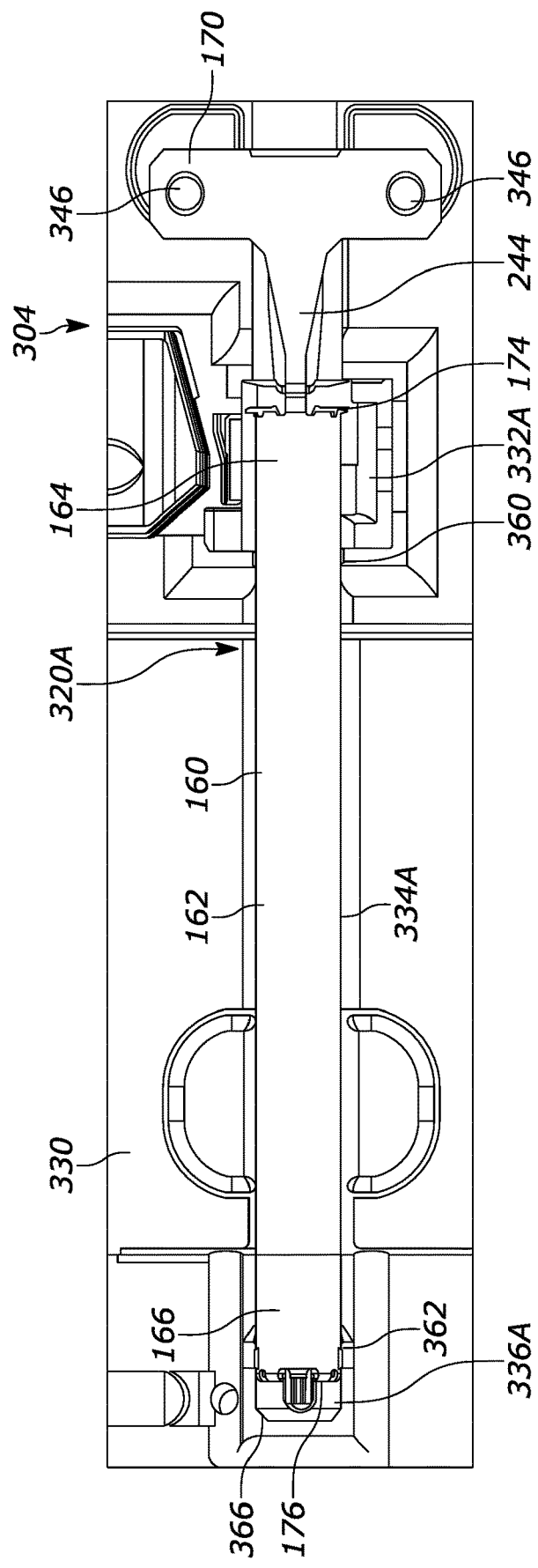
FIG. 19A is top view of the plunger rod straw disposed in the cavity of the first molding tool.

FIGS. 19A-19C illustrate a plunger body 162 disposed in the first cavity 320A of the first molding tool 304. Once again, the step 312 of loading plunger bodies 162 onto the first molding tool 304 includes loading the first end 164 of the plunger body 162 into the first molding portion 332A and the second end 166 into the second molding portion 336A. Loading the plunger body includes coupling the hanger 170 of the plunger body 162 to the mounting pins 346 of the first molding tool 304. The mounting pins 346 help maintain the position of the plunger body 162 relative to the cavity 320A when the system 300 subjects the plunger body 162 to various forces during the molding process (e.g., rotational and axial forces). The middle portion 334A of the cavity 320A receives the cylindrical outer wall 160 of the plunger body 162 and is specifically sized to tightly fit the plunger body 162.

In fact, as shown in FIGS. 19B and 19C, the first molding tool 304 engages the plunger body 162 at at least two locations 360, 362 to avoid plastic flash on the plunger body 162. The tight engagement between the outer wall 160 of the plunger body 162 and the walls 360, 362 of the first molding tool 304 reduces any molten plastic seepage from the first and second molding portions 332A, 336A when the system 300 injects molten plastic into the first and second molding tools 304, 404. In particular, the walls 360, 362 defined by the first and second molding portions 332A, 336A contact a circumference of the first and second ends 164, 166, respectively, of the plunger body 162. The walls 360, 362 of the first molding tool 304 block any molten plastic from seeping into the middle portion 334A of the cavity 320A. As a result, an axial wall 39 of a plunger 26 remains clear of any molded parts.

In FIG. 19B, the second molding portion 336A of the cavity 320A not only provides the tight contact between the wall 362 and the plunger body 162, but also provides half of the negative foot space that will define the foot portion 47 of a plunger 26. The negative foot space 336A extends from the corrugated edge 176 of the plunger body 162 because unlike the negative head space of the first molding portion 332A, the negative foot space of the second molding portion 336A does not surround the outer wall 160 of the plunger body 162. Rather, the second molding portions 336A of the first and second molding tools 304, 404 together provide a chamfered foot mold that surrounds a circumference of the corrugated edge 176 and extends axially away from the plunger body 162. The negative foot mold 336A has a chamfered end 366 to provide a self-centering mechanism for the plunger 26 when assembled within a syringe. In fact, the chamfered end 336 defines a chamfered portion of the foot 47, which acts as a barrier between the metal plunger body 162 and the glass of the syringe. As such, the plunger 26 manufactured according to the methods described herein, does not contact the glass of the syringe as the plunger 26 moves through the medical device 10.

Figure 20:
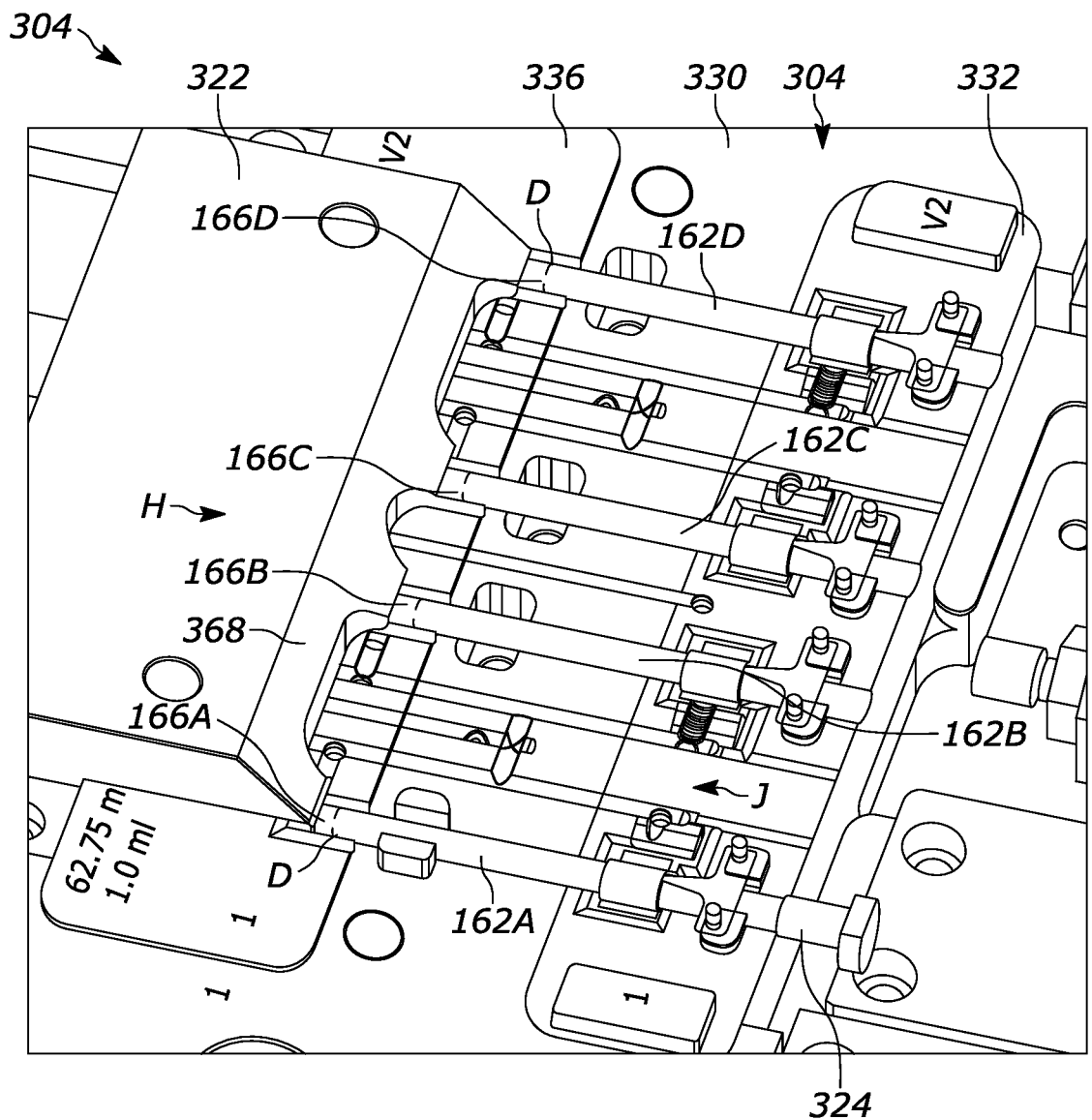
FIG. 20 is a top perspective view of a stop plate aligning the plurality of plunger rod straws in the first molding tool.

FIG. 20 illustrates a step of preparing the plunger bodies 162A-D loaded on the first molding tool 304. This step includes moving the plate 322 and the cores 324 toward the plurality of loaded plunger bodies 162A-D until both the plate 322 and the cores 324 engage each of the plunger bodies 162A-D. The plate 322 includes a ramped leading end 368 that aligns the plunger bodies 162A-D by evenly contacting the distal ends 166A-D of the plunger bodies 162A-D. After the first molding tool 304 is fully and properly loaded (i.e., no alarm triggered), the system 300 actuates the plate 322 to move in an H direction from an initial position, in which the ramped leading end 368 is spaced away from the plunger bodies 162A-D, to an engagement position, in which the ramped leading end 368 engages the plunger bodies 162 A-D.

Either simultaneously or shortly after the plate 322 engages the plunger bodies 162A-D, the system 300 actuates the cores 324 to move in a J direction, opposite the H direction, from an initial position, in which the cores 324 are spaced away from the plunger bodies 162, to an engagement position, in which each core 324 is inserted into an axial chamber 168 of the plunger bodies 162A-D. In the illustrated example, only one core 324 is shown. However, the first molding tool 304 includes a carriage (not shown) carrying four separate cores 324 corresponding to the four separate cavities 320A-D of the first molding tool 304.

When the cores 324 engage the plunger bodies 320A-D, each core 324 extends between the first molding portion 332A of the cavity, into the axial chamber 168 of the plunger body 320A-D, and almost entirely along the length of the plunger body 162A-D. The cores 324 extend to a position D relative to the outer wall 160 of the plunger body 162, and remain in position during the injection molding step 316. This position D also corresponds to a proximal end of the first portion 55 of the foot 47 (FIG. 4D) that is formed during injection molding. In other words, during the injecting step 316, molten plastic flows into the second end 166 and axial chamber 168 of the plunger body 162 until it reaches position D, where the core 124 blocks the molten plastic from flowing further in the axial cavity 168. The cores 324 also prevent unwanted seepage of molten plastic into the top end 164 and into the remaining axial chamber 168 of the plunger body 162.

Figure 21:
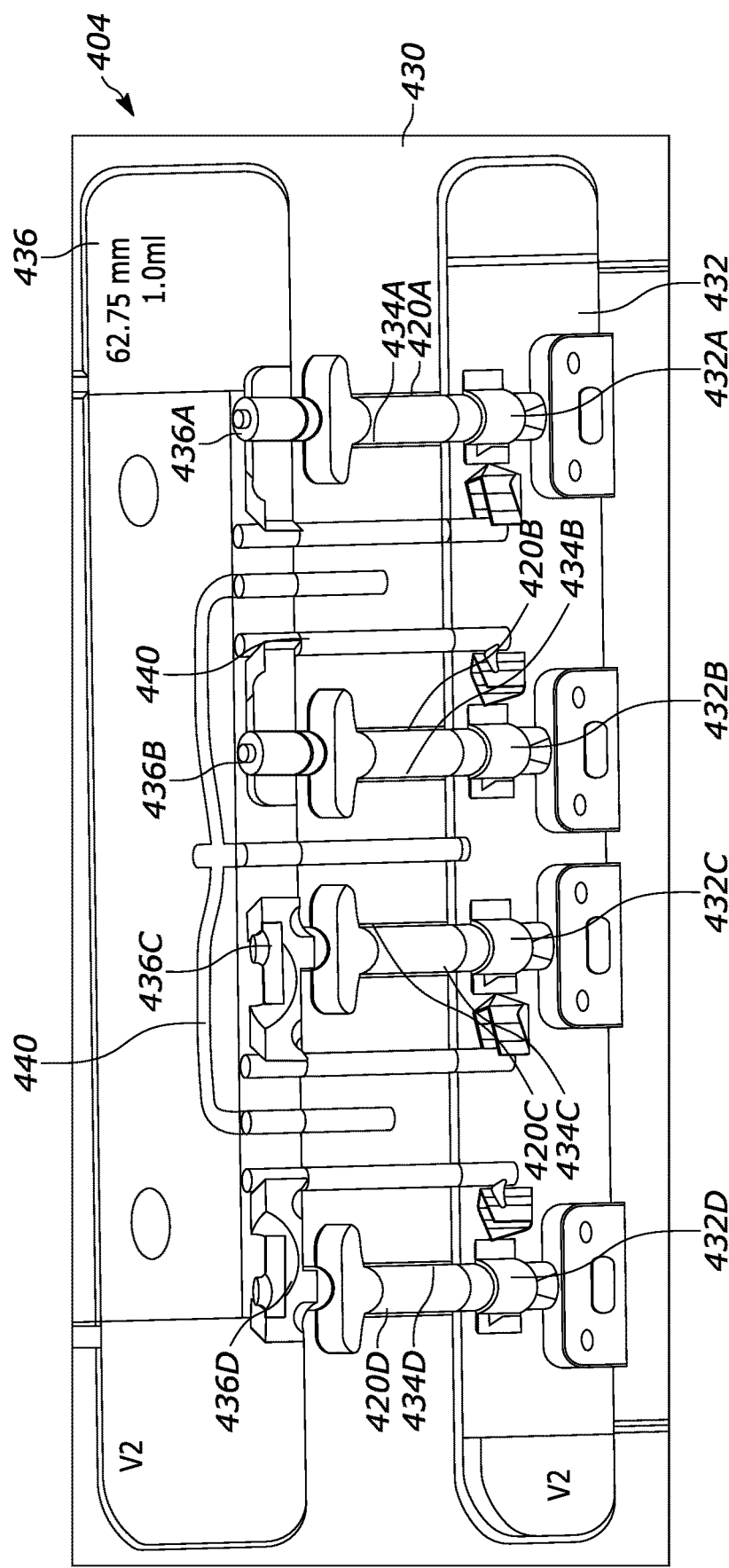
FIG. 21 is a perspective view of a mating surface of a second molding constructed in accordance with the teachings of the present disclosure.

FIG. 21 illustrates a second molding tool 404 constructed in accordance with the teachings of the present disclosure. The second molding tool 404 has similar features as the first molding tool 304 described above, except that the second molding tool 404 remains at Station II and couples with one or more first molding tools 304, 306 to complete the mold 410. Elements of the second molding tool 404 in FIG. 21 which are like the elements of the first molding tool 304 are designated by the same reference numeral, incremented by 100. A description of many of these elements is abbreviated or even eliminated in the interest of brevity. As previously discussed, the second molding tool 404 includes a plurality of cavities 420A-D that corresponds with the cavities 320A-D of the first molding tool 304 and a network of grooves 440 that corresponds with the network of grooves 340 of the first molding tool 304 to form a plurality of channels.

In FIG. 22, a mold 410 is assembled by clamping the first molding tool 304 to the second molding tool 404 in step 314 of the method 310. The platform 330 of the first molding tool 304 and a platform 430 of the second molding tool 404 sealingly mate when the first and second molding tools 304, 404 are clamped together at Station II. Each molding tool 304, 404 includes a centering mechanism or surface 380, 480 that accurately and precisely aligns the first and second molding tools 304, 404 prior to injecting the mold 410. In fact, each surface 380, 480 enables the first and second molding tools 304, 404 to align with less than 0.005 inches of clearance.

Figure 23:
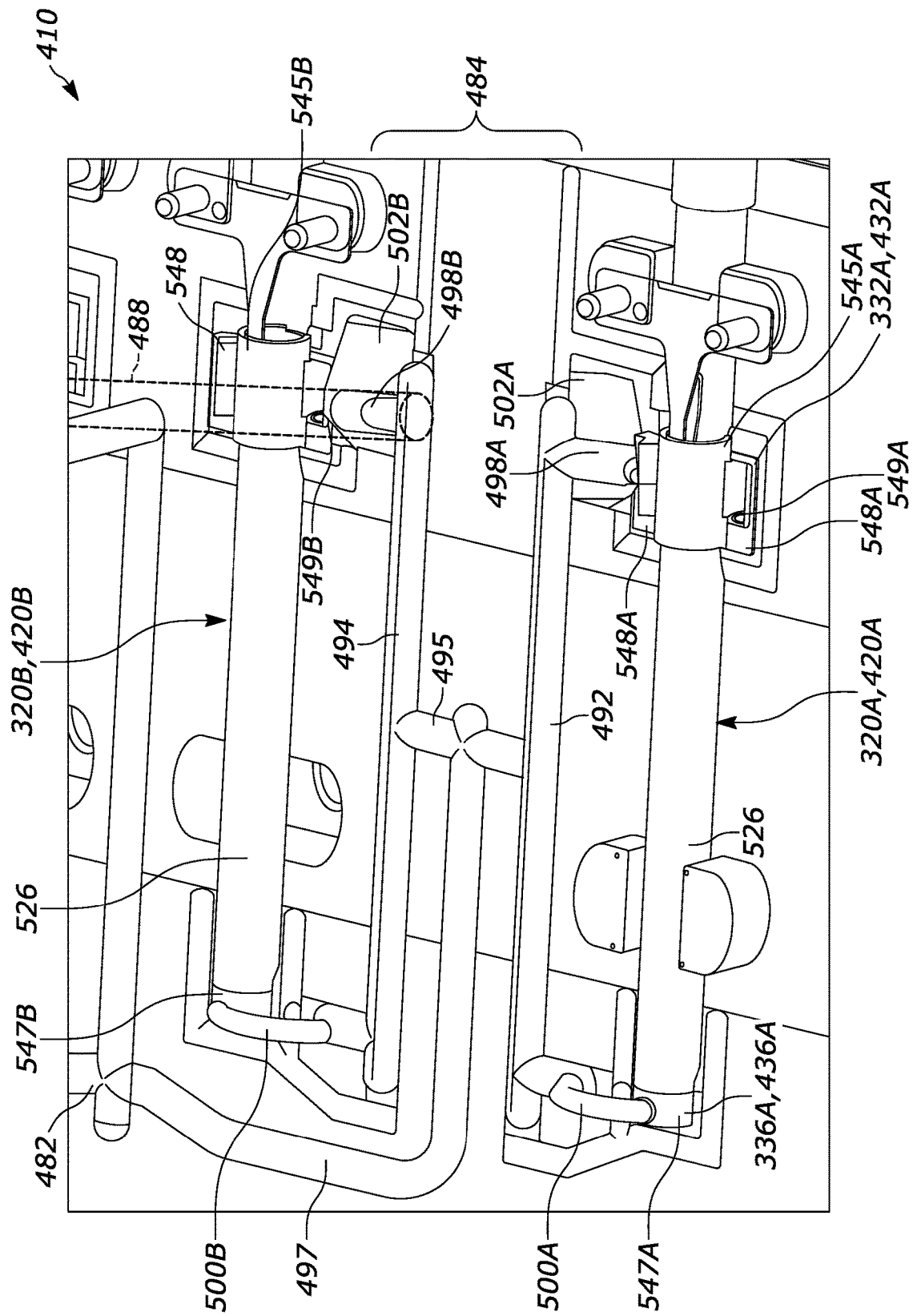
FIG. 23 is a perspective view of overmolded plunger bodies and a first group of channels formed during injection molding of the first and second molding tools.

After the first and second molding tools 304, 404 securely clamp to one another, the system 300 heats the clamped first and second molding tools 304, 404 with hot water (e.g., 120 degrees Celsius). Specifically, hot water flows through the cooling and heating channels 326 of the first molding tool 304. When the mold 410 reaches a desired high temperature, the system 300 injects molten plastic into a plurality of channels 482 of the mold 410 in step 316 to form an overmolded plunger body 526, as shown in FIG. 23. The system 300 injects molten plastic from a molten plastic source into the mold 410 at 800 bars of pressure.

FIG. 23 illustrates the step of injecting molten plastic into the channels of the mold 410 to form the overmolded plunger body. The overmolded plunger body 526 in the first cavity 320A, for example, includes a head 545A surrounding a portion of the first end 164 and a foot 547A extending from the second end 166 of the plunger body 162. The foot 547A is at least partially coupled to the inner wall and the head 545A is coupled to the outer wall 160 of the plunger body 162. The second molding tool 404 is hidden in FIG. 23 to how a network of channels 482 of the mold 410 are formed by mating the grooves 340, 440 of the first and second molding tools 304, 404. The network of channels 482 includes a first group 484 and symmetrical second group 486 of channels 482. FIG. 23 illustrates the first group 484, and FIG. 24A partially illustrates the second group 486 of channels 482. However, FIG. 17 shows how the grooves 340 formed in the first molding tool 304 are symmetrical about a midline M, which corresponds to the symmetry of the first and second groups of channels 482 formed by the mold 410. Each group 484, 486 of channels 382 includes a feed line 488, 492 that traverses through the second molding tool 404 to fluidly connect with to the network of channels 482.

Figure 24A:
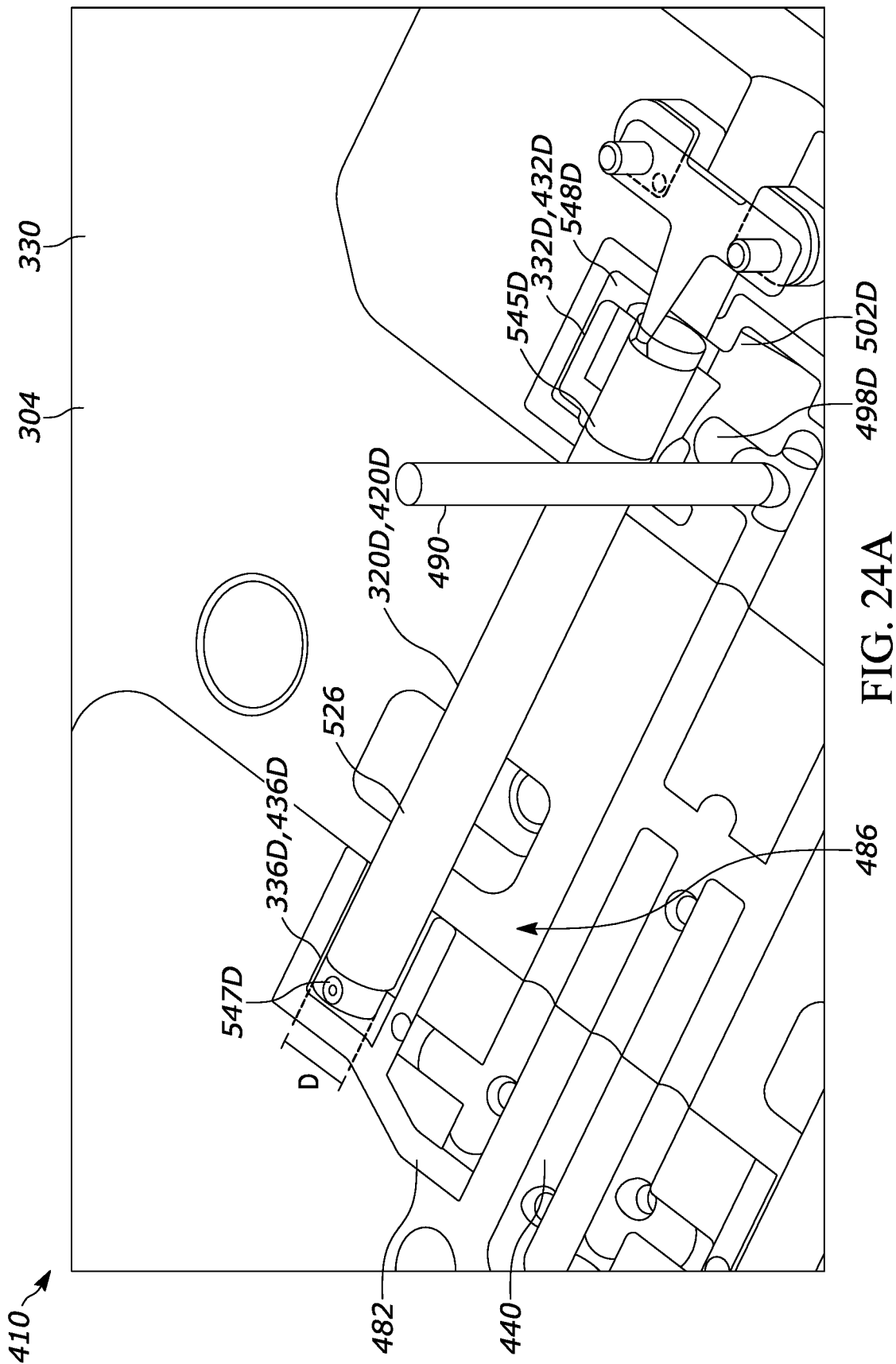
FIG. 24A is a perspective view of an overmolded plunger body and a second group of channels formed during injection molding of the first and second molding tools.

A first feed line 488 (shown in dashed lines in FIG. 23, for clarity) is disposed between the first and second cavities 320A, 320B of the first molding tool 304 and directs injected molten plastic through the first group of channels 484 and into the first and second molding portions 332A-B, 432A-B, 336A-B, 436A-B of the first and second cavities 320A, 420A, 320B, 420B. As shown in FIG. 24A, a second feed line 490 traverses the second molding tool 404 and connects to the second group 486 of channels 382 at a location between the third and fourth cavities 320C, 320D of the first molding tool 304. Similar to the first group of channels 484, the second group of channels 486 directs injected molten plastic into the first and second portions 332C, 432C, 336D, 436D of the third and fourth cavities 320C, 420C, 320D, 420D. While the illustrated example includes two feed lines 488, 490, other exemplary molding systems 300 may include additional feed lines for connecting the source of molten plastic and the first and second molding tools 304, 404. The additional feed lines may extend through one or both first and second molding tools 304, 404.

Each feed line 488, 490 connects the molten plastic source with both groups of channels 484, 486 for an even and efficient injection molding process. The molding system 300 injects plastic with sufficient force (e.g. approximately 800 bars) to simultaneously fill both the negative foot space 336A-D, 436A-D and the negative head space 332A-D, 432A-D of each cavity 320A-D, 420A-D of the mold 410. As shown in FIG. 23, the first and second molding portions 332A, 432A, 336A, 436A of the first cavity 320A, 420A are fluidly connected by a first arm channel 492, and the first and second molding portions 332B, 432B, 336B, 436B of the second cavity 320B, 420B are fluidly connected by a second arm channel 494. The step 316 of injecting molten plastic into the first cavity 320A, 420A, for example, of the mold 410 includes forming a head 545A having flanges 548A extending radially outwardly from the first end 164 of the plunger body 162 and forming a cam follower 549A on one or more of the flanges 548A. The head 545A is molded around a portion of the outer wall 160 of the plunger body 162 and couples to the corrugated edge 174 of the first end 164. The step 316 of injecting molten plastic into the mold 410 also includes forming a foot 547A in the first cavity 320A, 420A. The foot 547A is at least partially adjacent to the inner wall of the plunger body 162 and couples to the corrugated edge 176 of the second end 166 of the plunger body 162. It will be appreciated that similar molds are formed in each of the cavities of the mold 410.

The first and second arms 492, 494 are fluidly coupled together by a bridging channel 496. At opposite ends of each channel, the first and second arms 492, 494 are connected to first and second channels 498A-B, 500A-B that extend perpendicular relative to the arm 492, 494 and connect the arms 492, 494 to the first and second molding portions 332A, 432A, 336A, 436A. For example, the first and second channels 498A, 500A connect the first arm 492 with the first molding portion 332A, 432A and second molding portion 336A, 436A of the first cavity 320A, 420A. The same applies to connecting the first and second molding portions 332B, 432B, 336B, 436B of the second cavity 320B, 420B. The first and second arms 492, 494 are connected to each other by a bridge 495, which also connects the first group 484 and the second group 486 of channels 482 by way of an L channel 497. The second group 486 of channels 482 is similarly organized for injecting the third and fourth cavities 320C-D, 420C-D.

Figure 24B:
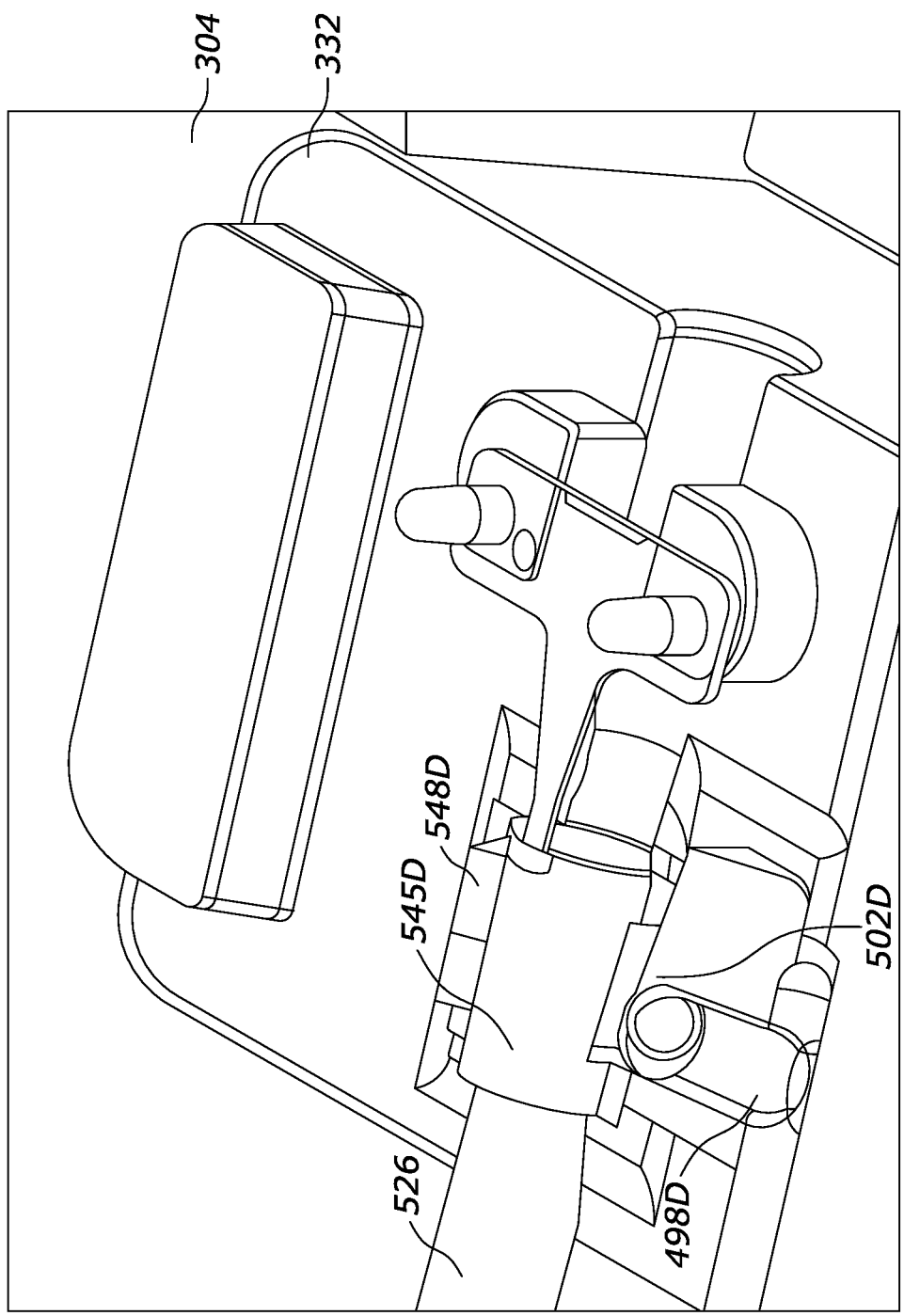
FIG. 24B is a partially magnified view of the overmolded plunger body and an adjacent channel of FIG. 24A.

As shown in FIG. 23, each connecting channel 498A-B, 500A-B is curved such that at least part of the channel 498A-B, 500A-B is formed entirely within the first or second molding tools 304, 404. In FIGS. 23 and 24B, the first connecting channels 498A, 498B, 498D curve beneath the overmolded head 545A, 545B, 545D, and the second connecting channels 500A, 500B, 500D curve above the overmolded foot 547A, 547B, 547D. The first connecting channels 498A-D extend beneath the overmolded heads 545A-D so that a ramped edge 502A-D of the first molding portion 332A-D severs the molded plastic channel when the ejector pins 348, 350 eject the overmolded plunger 526 from the cavity 320A-D. The second connecting channel 500A-D has a diameter D in a range of approximately 0.1 mm to approximately 0.2 mm such that when the overmolded plunger body 526 is ejected from the cavity 320A-D of the first molding tool 304, the molded plastic channels snap or break upon the ejecting force of the ejector pins 348, 350.

After the step of injecting 316 is complete, in step 318, the system 300 flushes the cooling channels 326 (FIG. 16) with cold water to cure the plastic in the mold 410. Subsequently, the system 300 releases the clamp between the first and second molding tools 304, 404, and rotates the table 308 approximately 180 degrees to position the overmolded plunger bodies 526 loaded on the first molding tool 304 at Station I. At Station I, the overmolded plunger bodies 526 are removed from the first molding tool 404. Removing the cured plunger from the first molding tool 304 includes activating the ejector pins 348, 350 in the first molding tool 304. The ejector pins 348, 350 disposed in each cavity 320A-D push against the cured plunger in a direction away from the platform 330 of the first molding tool 304. By ejecting the cured plunger, the molded channels attached to the overmolded head 545A-D and foot 547A-D automatically sever or break and form a connected piece that is removed by an operator. With the molded channels removed, a plurality of plungers 26, like the plunger 26 of FIGS. 4A-4E, may be removed individually from the first molding tool 304. After the plunger 26 is removed from the molding system 300, the hanger 170 is cut from the plunger 26.

The above description describes various devices, assemblies, components, subsystems and methods for use related to a drug delivery device. The devices, assemblies, components, subsystems, methods or drug delivery devices can further comprise or be used with a drug including but not limited to those drugs identified below as well as their generic and biosimilar counterparts. The term drug, as used herein, can be used interchangeably with other similar terms and can be used to refer to any type of medicament or therapeutic material including traditional and non-traditional pharmaceuticals, nutraceuticals, supplements, biologics, biologically active agents and compositions, large molecules, biosimilars, bioequivalents, therapeutic antibodies, polypeptides, proteins, small molecules and generics. Non-therapeutic injectable materials are also encompassed. The drug may be in liquid form, a lyophilized form, or in a reconstituted from lyophilized form. The following example list of drugs should not be considered as all-inclusive or limiting.

The drug will be contained in a reservoir. In some instances, the reservoir is a primary container that is either filled or pre-filled for treatment with the drug. The primary container can be a vial, a cartridge or a pre-filled syringe.

In some embodiments, the reservoir of the drug delivery device may be filled with or the device can be used with colony stimulating factors, such as granulocyte colony-stimulating factor (G-CSF). Such G-CSF agents include but are not limited to Neulasta® (pegfilgrastim, pegylated filgastrim, pegylated G-CSF, pegylated hu-Met-G-CSF) and Neupogen® (filgrastim, G-CSF, hu-MetG-CSF), UDE-NYCA® (pegfilgrastim-cbqv), Ziextenzo® (LA-EP2006; pegfilgrastim-bmez), or FULPHILA (pegfilgrastim-bmez).

In other embodiments, the drug delivery device may contain or be used with an erythropoiesis stimulating agent (ESA), which may be in liquid or lyophilized form. An ESA is any molecule that stimulates erythropoiesis. In some embodiments, an ESA is an erythropoiesis stimulating protein. As used herein, "erythropoiesis stimulating protein" means any protein that directly or indirectly causes activation of the erythropoietin receptor, for example, by binding to and causing dimerization of the receptor. Erythropoiesis stimulating proteins include erythropoietin and variants, analogs, or derivatives thereof that bind to and activate erythropoietin receptor; antibodies that bind to erythropoietin receptor and activate the receptor; or peptides that bind to and activate erythropoietin receptor. Erythropoiesis stimulating proteins include, but are not limited to, Epogen® (epoetin alfa), Aranesp® (darbepoetin alfa), Dynepo® (epoetin delta), Mircera® (methyoxy polyethylene glycol-epoetin beta), Hematide®, MRK-2578, INS-22, Retacrit® (epoetin zeta), Neorecormon® (epoetin beta), Silapo® (epoetin zeta), Binocrit® (epoetin alfa), epoetin alfa Hexal, Abseamed® (epoetin alfa), Ratioepo® (epoetin theta), Eporatio® (epoetin theta), Biopoin® (epoetin theta), epoetin alfa, epoetin beta, epoetin iota, epoetin omega, epoetin delta, epoetin zeta, epoetin theta, and epoetin delta, pegylated erythropoietin, carbamylated erythropoietin, as well as the molecules or variants or analogs thereof.

Among particular illustrative proteins are the specific proteins set forth below, including fusions, fragments, analogs, variants or derivatives thereof: OPGL specific antibodies, peptibodies, related proteins, and the like (also referred to as RANKL specific antibodies, peptibodies and the like), including fully humanized and human OPGL specific antibodies, particularly fully humanized monoclonal antibodies; Myostatin binding proteins, peptibodies, related proteins, and the like, including myostatin specific peptibodies; IL-4 receptor specific antibodies, peptibodies, related proteins, and the like, particularly those that inhibit activities mediated by binding of IL-4 and/or IL-13 to the receptor; Interleukin 1-receptor 1 ("IL1-R1") specific antibodies, peptibodies, related proteins, and the like; Ang2 specific antibodies, peptibodies, related proteins, and the like; NGF specific antibodies, peptibodies, related proteins, and the like; CD22 specific antibodies, peptibodies, related proteins, and the like, particularly human CD22 specific antibodies, such as but not limited to humanized and fully human antibodies, including but not limited to humanized and fully human monoclonal antibodies, particularly including but not limited to human CD22 specific IgG antibodies, such as, a dimer of a human-mouse monoclonal hLL2 gamma-chain disulfide linked to a human-mouse monoclonal hLL2 kappa-chain, for example, the human CD22 specific fully humanized antibody in Epratuzumab, CAS registry number 501423-23-0; IGF-1 receptor specific antibodies, peptibodies, and related proteins, and the like including but not limited to anti-IGF-1R antibodies; B-7 related protein 1 specific antibodies, peptibodies, related proteins and the like ("B7RP-1" and also referring to B7H2, ICOSL, B7h, and CD275), including but not limited to B7RP-specific fully human monoclonal IgG2 antibodies, including but not limited to fully human IgG2 monoclonal antibody that binds an epitope in the first immunoglobulin-like domain of B7RP-1, including but not limited to those that inhibit the interaction of B7RP-1 with its natural receptor, ICOS, on activated T cells; IL-15 specific antibodies, peptibodies, related proteins, and the like, such as, in particular, humanized monoclonal antibodies, including but not limited to HuMax IL-15 antibodies and related proteins, such as, for instance, 145c7; IFN gamma specific antibodies, peptibodies, related proteins and the like, including but not limited to human IFN gamma specific antibodies, and including but not limited to fully human anti-IFN gamma antibodies; TALL-1 specific antibodies, peptibodies, related proteins, and the like, and other TALL specific binding proteins; Parathyroid hormone ("PTH") specific antibodies, peptibodies, related proteins, and the like; Thrombopoietin receptor ("TPO-R") specific antibodies, peptibodies, related proteins, and the like; Hepatocyte growth factor ("HGF") specific antibodies, peptibodies, related proteins, and the like, including those that target the HGF/SF:cMet axis (HGF/SF:c-Met), such as fully human monoclonal antibodies that neutralize hepatocyte growth factor/scatter (HGF/SF); TRAIL-R2 specific antibodies, peptibodies, related proteins and the like; Activin A specific antibodies, peptibodies, proteins, and the like; TGF-beta specific antibodies, peptibodies, related proteins, and the like; Amyloid-beta protein specific antibodies, peptibodies, related proteins, and the like; c-Kit specific antibodies, peptibodies, related proteins, and the like, including but not limited to proteins that bind c-Kit and/or other stem cell factor receptors; OX40L specific antibodies, peptibodies, related proteins, and the like, including but not limited to proteins that bind OX40L and/or other ligands of the OX40 receptor; Activase® (alteplase, tPA); Aranesp® (darbepoetin alfa) Erythropoietin [30-asparagine, 32-threonine, 87-valine, 88-asparagine, 90-threonine], Darbepoetin alfa, novel erythropoiesis stimulating protein (NESP); Epogen® (epoetin alfa, or erythropoietin); GLP-1, Avonex® (interferon beta-1a); Bexxar® (tositumomab, anti-CD22 monoclonal antibody); Betaseron® (interferon-beta); Campath® (alemtuzumab, anti-CD52 monoclonal antibody); Dynepo® (epoetin delta); Velcade® (bortezomib); MLN0002 (anti-α4β7 mAb); MLN1202 (anti-CCR2 chemokine receptor mAb); Enbrel® (etanercept, TNF-receptor/Fc fusion protein, TNF blocker); Eprex® (epoetin alfa); Erbitux® (cetuximab, anti-EGFR/HER1/c-ErbB-1); Genotropin® (somatropin, Human Growth Hormone); Herceptin® (trastuzumab, anti-HER2/neu (erbB2) receptor mAb); Kanjinti™ (trastuzumab-anns) anti-HER2 monoclonal antibody, biosimilar to Herceptin®, or another product containing trastuzumab for the treatment of breast or gastric cancers; Humatrope® (somatropin, Human Growth Hormone); Humira® (adalimumab); Vectibix® (panitumumab), Xgeva® (denosumab), Prolia® (denosumab), Immunoglobulin G2 Human Monoclonal Antibody to RANK Ligand, Enbrel® (etanercept, TNF-receptor/Fc fusion protein, TNF blocker), Nplate® (romiplostim), rilotumumab, ganitumab, conatumumab, brodalumab, insulin in solution; Infergen® (interferon alfacon-1); Natrecor® (nesiritide); recombinant human B-type natriuretic peptide (hBNP); Kineret® (anakinra); Leukine® (sargamostim, rhuGM-CSF); LymphoCide® (epratuzumab, anti-CD22 mAb); Benlysta™ (lymphostat B, belimumab, anti-BlyS mAb); Metalyse® (tenecteplase, t-PA analog); Mircera® (methoxy polyethylene glycol-epoetin beta); Mylotarg® (gemtuzumab ozogamicin); Raptiva® (efalizumab); Cimzia® (certolizumab pegol, CDP 870); Solids™ (eculizumab); pexelizumab (anti-05 complement); Numax® (MEDI-524); Lucentis® (ranibizumab); Panorex® (17-1A, edrecolomab); Trabio® (lerdelimumab); TheraCim hR3 (nimotuzumab); Omnitarg (pertuzumab, 2C4); Osidem® (IDM-1); OvaRex® (B43.13); Nuvion® (visilizumab); cantuzumab mertansine (huC242-DM1); NeoRecormon® (epoetin beta); Neumega® (oprelvekin, human interleukin-11); Orthoclone OKT3® (muromonab-CD3, anti-CD3 monoclonal antibody); Procrit® (epoetin alfa); Remicade® (infliximab, anti-TNFα monoclonal antibody); Reopro® (abciximab, anti-GP IIb/IIIa receptor monoclonal antibody); Actemra® (anti-IL6 Receptor mAb); Avastin® (bevacizumab), HuMax-CD4 (zanolimumab); Mvasi™ (bevacizumab-awwb); Rituxan® (rituximab, anti-CD20 mAb); Tarceva® (erlotinib); Roferon-A®-(interferon alfa-2a); Simulect® (basiliximab); Prexige® (lumiracoxib); Synagis® (palivizumab); 145c7-CHO (anti-IL15 antibody, see U.S. Pat. No. 7,153,507); Tysabri® (natalizumab, anti-α4integrin mAb); Valortim® (MDX-1303, anti-B. anthracis protective antigen mAb); ABthrax™ Xolair® (omalizumab); ETI211 (anti-MRSA mAb); IL-1 trap (the Fc portion of human IgG1 and the extracellular domains of both IL-1 receptor components (the Type I receptor and receptor accessory protein)); VEGF trap (Ig domains of VEGFR1 fused to IgG1 Fc); Zenapax® (daclizumab); Zenapax® (daclizumab, anti-IL-2Rα mAb); Zevalin® (ibritumomab tiuxetan); Zetia® (ezetimibe); Orencia® (atacicept, TACI-Ig); anti-CD80 monoclonal antibody (galiximab); anti-CD23 mAb (lumiliximab); BR2-Fc (huBR3/huFc fusion protein, soluble BAFF antagonist); CNTO 148 (golimumab, anti-TNFα mAb); HGS-ETR1 (mapatumumab; human anti-TRAIL Receptor-1 mAb); HuMax-CD20 (ocrelizumab, anti-CD20 human mAb); HuMax-EGFR (zalutumumab); M200 (volociximab, anti-α5β1 integrin mAb); MDX-010 (ipilimumab, anti-CTLA-4 mAb and VEGFR-1 (IMC-18F1); anti-BR3 mAb; anti-C. difficile Toxin A and Toxin B C mAbs MDX-066 (CDA-1) and MDX-1388); anti-CD22 dsFv-PE38 conjugates (CAT-3888 and CAT-8015); anti-CD25 mAb (HuMax-TAC); anti-CD3 mAb (NI-0401); adecatumumab; anti-CD30 mAb (MDX-060); MDX-1333 (anti-IFNAR); anti-CD38 mAb (HuMax CD38); anti-CD40L mAb; anti-Cripto mAb; anti-CTGF Idiopathic Pulmonary Fibrosis Phase I Fibrogen (FG-3019); anti-CTLA4 mAb; anti-eotaxin1 mAb (CAT-213); anti-FGF8 mAb; anti-ganglioside GD2 mAb; anti-ganglioside GM2 mAb; anti-GDF-8 human mAb (MYO-029); anti-GM-CSF Receptor mAb (CAM-3001); anti-HepC mAb (HuMax HepC); anti-IFNα mAb (MEDI-545, MDX-198); anti-IGF1R mAb; anti-IGF-1R mAb (HuMax-Inflam); anti-IL12 mAb (ABT-874); anti-IL12/1L23 mAb (CNTO 1275); anti-IL13 mAb (CAT-354); anti-IL2Ra mAb (HuMax-TAC); anti-IL5 Receptor mAb; anti-integrin receptors mAb (MDX-018, CNTO 95); anti-IP10 Ulcerative Colitis mAb (MDX-1100); BMS-66513; anti-Mannose Receptor/hCGβ mAb (MDX-1307); anti-mesothelin dsFv-PE38 conjugate (CAT-5001); anti-PD1mAb (MDX-1106 (ONO-4538)); anti-PDGFRα antibody (IMC-3G3); anti-TGFβ mAb (GC-1008); anti-TRAIL Receptor-2 human mAb (HGS-ETR2); anti-TWEAK mAb; anti-VEGFR/Flt-1 mAb; and anti-ZP3 mAb (HuMax-ZP3).

In some embodiments, the drug delivery device may contain or be used with a sclerostin antibody, such as but not limited to romosozumab, blosozumab, BPS 804 (Novartis), Evenity™ (romosozumab-aqqg), another product containing romosozumab for treatment of postmenopausal osteoporosis and/or fracture healing and in other embodiments, a monoclonal antibody (IgG) that binds human Proprotein Convertase Subtilisin/Kexin Type 9 (PCSK9). Such PCSK9 specific antibodies include, but are not limited to, Repatha® (evolocumab) and Praluent® (alirocumab). In other embodiments, the drug delivery device may contain or be used with rilotumumab, bixalomer, trebananib, ganitumab, conatumumab, motesanib diphosphate, brodalumab, vidupiprant or panitumumab. In some embodiments, the reservoir of the drug delivery device may be filled with or the device can be used with IMLYGIC® (talimogene laherparepvec) or another oncolytic HSV for the treatment of melanoma or other cancers including but are not limited to OncoVEXGALV/CD; OrienX010; G207, 1716; NV1020; NV12023; NV1034; and NV1042. In some embodiments, the drug delivery device may contain or be used with endogenous tissue inhibitors of metalloproteinases (TIMPs) such as but not limited to TIMP-3. In some embodiments, the drug delivery device may contain or be used with Aimovig® (erenumab-aooe), anti-human CGRP-R (calcitonin gene-related peptide type 1 receptor) or another product containing erenumab for the treatment of migraine headaches. Antagonistic antibodies for human calcitonin gene-related peptide (CGRP) receptor such as but not limited to erenumab and bispecific antibody molecules that target the CGRP receptor and other headache targets may also be delivered with a drug delivery device of the present disclosure. Additionally, bispecific T cell engager (BITE®) molecules such as but not limited to BLINCYTO® (blinatumomab) can be used in or with the drug delivery device of the present disclosure. In some embodiments, the drug delivery device may contain or be used with an APJ large molecule agonist such as but not limited to apelin or analogues thereof. In some embodiments, a therapeutically effective amount of an anti-thymic stromal lymphopoietin (TSLP) or TSLP receptor antibody is used in or with the drug delivery device of the present disclosure. In some embodiments, the drug delivery device may contain or be used with Avsola™ (infliximab-axxq), anti-TNF a monoclonal antibody, biosimilar to Remicade® (infliximab) (Janssen Biotech, Inc.) or another product containing infliximab for the treatment of autoimmune diseases. In some embodiments, the drug delivery device may contain or be used with Kyprolis® (carfilzomib), (2S)—N—((S)-1-((S)-4-methyl-1-((R)-2-methyloxiran-2-yl)-1-oxopentan-2-ylcarbamoyl)-2-phenylethyl)-2-((S)-2-(2-morpholinoacetamido)-4-phenylbutanamido)-4-methylpentanamide, or another product containing carfilzomib for the treatment of multiple myeloma. In some embodiments, the drug delivery device may contain or be used with Otezla® (apremilast), N-[2-[(1S)-1-(3-ethoxy-4-methoxyphenyl)-2-(methylsulfonyl)ethyl]-2,3-dihydro-1,3-dioxo- 1H-isoindol-4-yl]acetamide, or another product containing apremilast for the treatment of various inflammatory diseases. In some embodiments, the drug delivery device may contain or be used with Parsabiv™ (etelcalcetide HCl, KAI-4169) or another product containing etelcalcetide HCl for the treatment of secondary hyperparathyroidism (sHPT) such as in patients with chronic kidney disease (KD) on hemodialysis. In some embodiments, the drug delivery device may contain or be used with ABP 798 (rituximab), a biosimilar candidate to Rituxan®/MabThera™, or another product containing an anti-CD20 monoclonal antibody. In some embodiments, the drug delivery device may contain or be used with a VEGF antagonist such as a non-antibody VEGF antagonist and/or a VEGF-Trap such as aflibercept (Ig domain 2 from VEGFR1 and Ig domain 3 from VEGFR2, fused to Fc domain of IgG1). In some embodiments, the drug delivery device may contain or be used with ABP 959 (eculizumab), a biosimilar candidate to Soliris®, or another product containing a monoclonal antibody that specifically binds to the complement protein C5. In some embodiments, the drug delivery device may contain or be used with Rozibafusp alfa (formerly AMG 570) is a novel bispecific antibody-peptide conjugate that simultaneously blocks ICOSL and BAFF activity. In some embodiments, the drug delivery device may contain or be used with Omecamtiv mecarbil, a small molecule selective cardiac myosin activator, or myotrope, which directly targets the contractile mechanisms of the heart, or another product containing a small molecule selective cardiac myosin activator. In some embodiments, the drug delivery device may contain or be used with Sotorasib (formerly known as AMG 510), a $KRAS^{G12C}$ small molecule inhibitor, or another product containing a $KRAS^{G12C}$ small molecule inhibitor. In some embodiments, the drug delivery device may contain or be used with Tezepelumab, a human monoclonal antibody that inhibits the action of thymic stromal lymphopoietin (TSLP), or another product containing a human monoclonal antibody that inhibits the action of TSLP. In some embodiments, the drug delivery device may contain or be used with AMG 714, a human monoclonal antibody that binds to Interleukin-15 (IL-15) or another product containing a human monoclonal antibody that binds to Interleukin-15 (IL-15). In some embodiments, the drug delivery device may contain or be used with AMG 890, a small interfering RNA (siRNA) that lowers lipoprotein(a), also known as Lp(a), or another product containing a small interfering RNA (siRNA) that lowers lipoprotein(a). In some embodiments, the drug delivery device may contain or be used with ABP 654 (human IgG1 kappa antibody), a biosimilar candidate to Stelara®, or another product that contains human IgG1 kappa antibody and/or binds to the p40 subunit of human cytokines interleukin (IL)-12 and IL-23. In some embodiments, the drug delivery device may contain or be used with Amjevita™ or Amgevita™ (formerly ABP 501) (mab anti-TNF human IgG1), a biosimilar candidate to Humira®, or another product that contains human mab anti-TNF human IgG1. In some embodiments, the drug delivery device may contain or be used with AMG 160, or another product that contains a half-life extended (HLE) anti-prostate-specific membrane antigen (PSMA) x anti-CD3 BiTE® (bispecific T cell engager) construct. In some embodiments, the drug delivery device may contain or be used with AMG 119, or another product containing a delta-like ligand 3 (DLL3) CART (chimeric antigen receptor T cell) cellular therapy. In some embodiments, the drug delivery device may contain or be used with AMG 119, or another product containing a delta-like ligand 3 (DLL3) CART (chimeric antigen receptor T cell) cellular therapy. In some embodiments, the drug delivery device may contain or be used with AMG 133, or another product containing a gastric inhibitory polypeptide receptor (GIPR) antagonist and GLP-1R agonist. In some embodiments, the drug delivery device may contain or be used with AMG 171 or another product containing a Growth Differential Factor 15 (GDF15) analog. In some embodiments, the drug delivery device may contain or be used with AMG 176 or another product containing a small molecule inhibitor of myeloid cell leukemia 1 (MCL-1). In some embodiments, the drug delivery device may contain or be used with AMG 199 or another product containing a half-life extended (HLE) bispecific T cell engager construct (BITE®). In some embodiments, the drug delivery device may contain or be used with AMG 256 or another product containing an anti-PD-1×IL21 mutein and/or an IL-21 receptor agonist designed to selectively turn on the Interleukin 21 (IL-21) pathway in programmed cell death-1 (PD-1) positive cells. In some embodiments, the drug delivery device may contain or be used with AMG 330 or another product containing an anti-CD33 x anti-CD3 BiTE® (bispecific T cell engager) construct. In some embodiments, the drug delivery device may contain or be used with AMG 404 or another product containing a human anti-programmed cell death-1(PD-1) monoclonal antibody being investigated as a treatment for patients with solid tumors. In some embodiments, the drug delivery device may contain or be used with AMG 427 or another product containing a half-life extended (HLE) anti-fms-like tyrosine kinase 3 (FLT3) x anti-CD3 BiTE® (bispecific T cell engager) construct. In some embodiments, the drug delivery device may contain or be used with AMG 430 or another product containing an anti-Jagged-1 monoclonal antibody. In some embodiments, the drug delivery device may contain or be used with AMG 506 or another product containing a multi-specific FAP×4-1BB-targeting DARPin® biologic under investigation as a treatment for solid tumors. In some embodiments, the drug delivery device may contain or be used with AMG 509 or another product containing a bivalent T-cell engager and is designed using XmAb® 2+1 technology. In some embodiments, the drug delivery device may contain or be used with AMG 562 or another product containing a half-life extended (HLE) CD19×CD3 BiTE® (bispecific T cell engager) construct. In some embodiments, the drug delivery device may contain or be used with Efavaleukin alfa (formerly AMG 592) or another product containing an IL-2 mutein Fc fusion protein. In some embodiments, the drug delivery device may contain or be used with AMG 596 or another product containing a CD3 x epidermal growth factor receptor vIII (EGFRvIII) BiTE® (bispecific T cell engager) molecule. In some embodiments, the drug delivery device may contain or be used with AMG 673 or another product containing a half-life extended (HLE) anti-CD33 x anti-CD3 BiTE® (bispecific T cell engager) construct. In some embodiments, the drug delivery device may contain or be used with AMG 701 or another product containing a half-life extended (HLE) anti-B-cell maturation antigen (BCMA) x anti-CD3 BiTE® (bispecific T cell engager) construct. In some embodiments, the drug delivery device may contain or be used with AMG 757 or another product containing a half-life extended (HLE) anti-delta-like ligand 3 (DLL3)×anti-CD3 BiTE® (bispecific T cell engager) construct. In some embodiments, the drug delivery device may contain or be used with AMG 910 or another product containing a half-life extended (HLE) epithelial cell tight junction protein claudin 18.2×CD3 BiTE® (bispecific T cell engager) construct.

Although the drug delivery devices, assemblies, components, subsystems and methods have been described in terms of exemplary embodiments, they are not limited thereto. The detailed description is to be construed as exemplary only and does not describe every possible embodiment of the present disclosure. Numerous alternative embodiments could be implemented, using either current technology or technology developed after the filing date of this patent that would still fall within the scope of the claims defining the invention(s) disclosed herein.

Those skilled in the art will recognize that a wide variety of modifications, alterations, and combinations can be made with respect to the above described embodiments without departing from the spirit and scope of the invention(s) disclosed herein, and that such modifications, alterations, and combinations are to be viewed as being within the ambit of the inventive concept(s).

What is claimed:

1. A method of manufacturing a plunger of a drug delivery device, the method comprising:
    forming a plunger body having an inner wall defining an axial chamber and an outer wall, the plunger body including a first end and a second end opposite the first end;
    loading the plunger body into a cavity of a first molding tool of a molding system;
    coupling a second molding tool to the first molding tool loaded with the plunger body to form a plurality of channels defined by grooves in the first and second molding tools, the second molding tool including a cavity sized to receive a portion of the plunger body when the plunger body is disposed in the cavity of the first molding tool; and
    injecting molten plastic into the plurality of channels of the coupled first and second molding tools to form an overmolded plunger body, the overmolded plunger body having at least one overmolded portion.

2. The method of claim 1, wherein injecting molten plastic includes injecting molten plastic to form a head coupled to the first end of the plunger body and a foot coupled to the second end of the plunger body, the foot at least partially coupled to the inner wall and the head coupled to the outer wall of the plunger body, and wherein the at least one overmolded portion includes the head and the foot.

3. The method of claim 1, further comprising moving the first molding tool from a first position to a second position before coupling the second molding tool to the first molding tool.

4. The method of claim 1, further comprising inserting a rod into the axial chamber of the plunger body before coupling the first molding tool to the second molding tool.

5. The method of claim 1, injecting the plurality of channels includes injecting a curved channel formed in the second molding tool, the curved channel including a diameter in a range of approximately 0.1 mm to approximately 0.2 mm and fluidly coupled to a second molding portion of at least one of the cavity of the first molding tool or the cavity of the second molding tool, wherein at least one of the cavity of the first molding tool or the cavity of the second molding tool is at least partially defined by a first molding portion, a middle portion, and the second molding portion.

6. The method of claim 1, further comprising:
    curing the plunger body; and
    removing the cured plunger body from the first molding tool by activating an ejector pin in the first molding tool, the ejector pins pushing the cured plunger body away from the cavity formed in the first molding tool.

7. The method of claim 1, wherein loading the plunger body includes loading a plurality of plunger bodies onto the first molding tool of the molding system, the first molding tool including a plurality of cavities.

8. The method of claim 1, wherein loading the plunger body into the cavity includes placing the plunger body over a vacuum slot formed in a wall of the first molding tool, the vacuum configured to adhere the plunger body to the molding tool.

9. The method of claim 1, wherein forming the plunger body includes stamping a plurality of plunger bodies from blank of sheet metal.

10. The method of claim 1, wherein forming the plunger body includes cutting a corrugated edge into a blank of sheet metal and bending the corrugated edge such that the first end of the plunger body includes the corrugated edge bent outwardly relative to the axial chamber.

11. The method of claim 1, wherein forming the plunger body includes cutting a corrugated edge into a blank of sheet metal and bending the corrugated edge such that the second end of the plunger body includes the corrugated edge bent inwardly relative to the axial chamber.

12. A method of molding a plunger of a drug delivery device, the method comprising:
loading a plunger body into a cavity of a first molding tool of a molding system, the plunger body including an inner wall defining an axial chamber, an outer wall, a first end, a second end opposite the first end, wherein the cavity at least partially defines a first molding portion, a middle portion, and a second molding portion;
coupling a second molding tool to the first molding tool loaded with the plunger body to form a plurality of channels defined by grooves in the first and second molding tools; and
injecting molten plastic into the plurality of channels of the coupled first and second molding tools and into the first molding portion and the second molding portion to form an overmolded plunger body, the overmolded plunger body including a head coupled to the outer wall and at least partially surrounding the first end of the plunger body and a foot coupled to the second end of the plunger body.

13. The method of claim 12, further comprising moving the first molding tool from a first position to a second position before coupling the second molding tool to the first molding tool.

14. The method of claim 13, wherein moving the first molding tool includes rotating a movable table at least 180 degrees, the first molding tool attached to a surface of the movable table.

15. The method of claim 12, wherein injecting molten plastic into the plurality of channels includes injecting molten plastic into the second molding tool when first molding tool is coupled to the second molding tool.

16. The method of claim 12, further comprising inserting a rod into the axial chamber of the plunger body before coupling the first molding tool to the second molding tool.

17. The method of claim 12, wherein injecting molten plastic into the plurality of channels includes injecting molten plastic into a curved channel formed in the second molding tool, the curved channel fluidly coupled to at least one of the second molding portion of the cavity of the first molding tool or a second molding portion of a cavity of the second molding tool.

18. The method of claim 12, wherein loading the plunger body includes loading the first end into the first molding portion and loading the second end into the second molding portion of the cavity.

19. The method of claim 12, wherein injecting molten plastic into the plurality of channels includes injecting molten plastic into the first and second molding tools, the plurality of channels extending between the first molding portion and the second molding portion of the first molding tool and between a first molding portion and a second molding portion of the second molding tool.

20. The method of claim 19, wherein injecting molten plastic into the first and second molding tools includes forming the head including at least one flange extending radially outwardly from the plunger body and forming a cam follower on the at least one flange.

* * * * *